(12) United States Patent
Narquizian et al.

(10) Patent No.: US 8,877,744 B2
(45) Date of Patent: Nov. 4, 2014

(54) 1,4-OXAZEPINES AS BACE1 AND/OR BACE2 INHIBITORS

(75) Inventors: Robert Narquizian, Zaessingue (FR); Thomas Woltering, Freiburg (DE); Wolfgang Wostl, Grenzach-Wyhlen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 252 days.

(21) Appl. No.: 13/432,003

(22) Filed: Mar. 28, 2012

(65) Prior Publication Data

US 2012/0253035 A1 Oct. 4, 2012

(30) Foreign Application Priority Data

Apr. 4, 2011 (EP) .................................... 11161044

(51) Int. Cl.
*A61K 31/553* (2006.01)
*C07D 267/10* (2006.01)
*C07D 413/10* (2006.01)
*C07D 413/14* (2006.01)
*C07D 417/10* (2006.01)

(52) U.S. Cl.
CPC ............ *C07D 413/10* (2013.01); *C07D 413/14* (2013.01); *C07D 267/10* (2013.01); *C07D 417/10* (2013.01)
USPC .................. 514/211.01; 514/211.15; 540/544

(58) Field of Classification Search
USPC .......................... 514/211.01, 211.15; 540/544
See application file for complete search history.

(56) References Cited

U.S. PATENT DOCUMENTS

2010/0093999 A1 4/2010 Motoki et al.

FOREIGN PATENT DOCUMENTS

WO 2011/009943 1/2011

OTHER PUBLICATIONS (International Search Report PCT/EP2012/055917 Apr. 2, 2012).
Lagos et al., "Blood" 109(4):1550-1558 (2007).
Woodard-Grice et al., "J. Biol. Chem." 283(39):26364-26373 (2008).
Kuhn et al., "J. Biol. Chem." 282(16):11982-11995 (2007).
Fukui et al., Cell Metab. 2:373-384 (2005).
Akpinar et al., Cell Metab. 2:385-397 (2005).
Finzi et al., "Ultrastruct. Pathol." 32(6):246-251 (2008).
Li et al., "Aging Cell" 5(2):153-165 (2006).
Kiljanski et al., "Thyroid" 15(7):645-652 (2005).
Kim et al., "Neurobiology of Disease" 22(2):346-356 (2006).
Hoffmeister et al., "Journal of the Pancreas" 10(5):501-506 (2009).
Toegel et al., "Osteoarthritis & Cartilage" 18(2)240-248 (2010).
Hodges et al., Hum. Mol. Genet. 15:965-977 (2006).
Talantov et al., Clin. Cancer Res. 11:7234-7242 (2005).
Hussain et al., "Molecular & Cellular Neurosciences" 16:609-619 (2000).
Vassar et al., BACE, Science 286:735 (1999).
Greenberg et al., Ann. Neurol. 57:664-678 (2005).
Sugimoto et al., "J. Biol. Chem." 282(48):34896-34903 (2007).
Roberds et al., Hum. Mol. Genet. 10(12):1317-1324 (2001).
Hedlund et al., Cancer Research 68(2):388-394 (2008).
Luo et al., "Nature Neuroscience" 3:231-232 (2001).
Desnues et al., Clin. Vaccine Immunol. 13:170-178 (2006).
Selkoe et al., "Annual Review Cell Biology" 10:373-403 (1994).
Basset et al., Scand. J. Immunol. 51:307-311 (2000).
Hardy et al., "Science" 297 (5580):353-356 (2002).
Prentki et al., J. Clin. Investig. 116(7):1802-1812 (2006).
Gatchel et al., Proc. Natl. Acad. Sci. USA 105:1291-1296 (2008).
McConlogue et al., "J. Biol. Chem." 282(36):26326-26334 (2007).
Kondoh et al., "Breast Cancer & Research Treatment" 78(1):37-44 (2003).
Zimmet et al., Nature 414:782-787 (2001).
Kihara et al., Proc. Natl. Acad. Sci. USA 106:21807-21812 (2009).
Koistinen et al., "Muscle & Nerve" 34(4):444-450 (2006).
Barbiero et al., Exp. Neurol. 182:335-345 (2003).
Baggio et al., Annu. Rev. Med. 57:265-281 (2006).
Maugeri et al., "Srp Arh Celok Lek—Abstract" 138:50-52 (2010).
Merten et al., "Zeitschrift fur Kardiologie" ((English language Summary is attached to the reference)), 93(11):855-863 (2004).
Grewal et al., Mol. Cell Biol. 26:4970-4981 (2006).
Vattemi et al., "Lancet" ((9297)), 358:1962-1964 (2001).
Wild et al., "Diabetes Care" 27(5):1047-1053 (2004).
Lichtenthaler et al., "J. Biol. Chem." 278(49):48713-48719 (2003).

*Primary Examiner* — Brenda Coleman

(57) ABSTRACT

The present invention relates to 1,4 Oxazepines of formula I

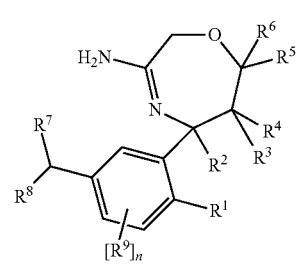

having BACE1 and/or BACE2 inhibitory activity, their manufacture, pharmaceutical compositions containing them and their use as therapeutically active substances. The active compounds of the present invention are useful in the therapeutic and/or prophylactic treatment of e.g. Alzheimer's disease and type 2 diabetes.

31 Claims, No Drawings

1,4-OXAZEPINES AS BACE1 AND/OR BACE2 INHIBITORS

PRIORITY TO RELATED APPLICATION(S)

This application claims the benefit of European Patent Application No. 11161044.0, filed Apr. 4, 2011, which is hereby incorporated by reference in its entirety.

BACKGROUND

Alzheimer's disease (AD) is a neurodegenerative disorder of the central nervous system and the leading cause of a progressive dementia in the elderly population. Its clinical symptoms are impairment of memory, cognition, temporal and local orientation, judgment and reasoning but also severe emotional disturbances. There are currently no treatments available which can prevent the disease or its progression or stably reverse its clinical symptoms. AD has become a major health problem in all societies with high life expectancies and also a significant economic burden for their health systems.

AD is characterized by 2 major pathologies in the central nervous system (CNS), the occurrence of amyloid plaques and neurofibrillar tangles (Hardy et al., The amyloid hypothesis of Alzheimer's disease: progress and problems on the road to therapeutics, Science. 2002 Jul. 19; 297(5580):353-6, Selkoe, Cell biology of the amyloid beta-protein precursor and the mechanism of Alzheimer's disease, Annu Rev Cell Biol. 1994; 10:373-403). Both pathologies are also commonly observed in patients with Down's syndrome (trisomy 21), which also develop AD-like symptoms in early life. Neurofibrillar tangles are intracellular aggregates of the microtubule-associated protein tau (MAPT). Amyloid plaques occur in the extracellular space; their principal components are Aβ-peptides. The latter are a group of proteolytic fragments derived from the β-amyloid precursor protein (APP) by a series of proteolytic cleavage steps. Several forms of APP have been identified of which the most abundant are proteins of 695, 751 and 770 amino acids length. They all arise from a single gene through differential splicing. The Aβ-peptides are derived from the same domain of the APP but differ at their N- and C-termini, the main species are of 40 and 42 amino-acid length. There are several lines of evidence which strongly suggest that aggregated Aβ-peptides are the essential molecules in the pathogenesis of AD: 1) amyloid plaques formed of Aβ-peptides are invariably part of the AD pathology; 2) Aβ-peptides are toxic for neurons; 3) in Familial Alzheimer's Disease (FAD) the mutations in the disease genes APP, PSN1, PSN2 lead to increased levels of Aβ-peptides and early brain amyloidosis; 4) transgenic mice which express such FAD genes develop a pathology which bears many resemblances to the human disease. Aβ-peptides are produced from APP through the sequential action of 2 proteolytic enzymes termed β- and γ-secretase. β-Secretase cleaves first in the extracellular domain of APP approximately 28 amino acids outside of the transmembrane domain (TM) to produce a C-terminal fragment of APP containing the TM- and the cytoplasmatic domain (CTFβ). CTFβ is the substrate for γ-secretase which cleaves at several adjacent positions within the TM to produce the Aβ peptides and the cytoplasmic fragment. The γ-secretase is a complex of at least 4 different proteins, its catalytic subunit is very likely a presenilin protein (PSEN1, PSEN2). The β-secretase (BACE1, Asp2; BACE stands for β-site APP-cleaving enzyme) is an aspartyl protease which is anchored into the membrane by a transmembrane domain (Vassar et al., Beta-secretase cleavage of Alzheimer's amyloid precursor protein by the transmembrane aspartic protease BACE, Science. 1999 Oct. 22; 286(5440):735). It is expressed in many tissues of the human organism but its level is especially high in the CNS. Genetic ablation of the BACE1 gene in mice has clearly shown that its activity is essential for the processing of APP which leads to the generation of Aβ-peptides, in the absence of BACE1 no Aβ-peptides are produced (Luo et al., Mice deficient in BACE1, the Alzheimer's beta-secretase, have normal phenotype and abolished beta-amyloid generation, Nat. Neurosci. 2001 March; 4(3):231-2, Roberds et al., BACE knockout mice are healthy despite lacking the primary beta-secretase activity in brain: implications for Alzheimer's disease therapeutics, Hum Mol. Genet. 2001 Jun. 1; 10(12):1317-24). Mice which have been genetically engineered to express the human APP gene and which form extensive amyloid plaques and Alzheimer's disease like pathologies during aging fail to do so when β-secretase activity is reduced by genetic ablation of one of the BACE1 alleles (McConlogue et al., Partial reduction of BACE1 has dramatic effects on Alzheimer plaque and synaptic pathology in APP Transgenic Mice. J Biol. Chem. 2007 Sep. 7; 282(36):26326). It is thus presumed that inhibitors of BACE1 activity can be useful agents for therapeutic intervention in Alzheimer's disease (AD).

Type 2 diabetes (T2D) is caused by insulin resistance and inadequate insulin secretion from pancreatic β-cells leading to poor blood-glucose control and hyperglycemia (M Prentki & C J Nolan, "Islet beta-cell failure in type 2 diabetes." J. Clin. Investig. 2006, 116(7), 1802-1812). Patients with T2D have an increased risk of microvascular and macrovascular disease and a range of related complications including diabetic nephropathy, retinopathy and cardiovascular disease. In 2000, an estimated 171 million people had the condition with the expectation that this figure will double by 2030 (S Wild, G Roglic, A Green, R. Sicree & H King, "Global prevalence of diabetes", Diabetes Care 2004, 27(5), 1047-1053), making the disease a major healthcare problem. The rise in prevalence of T2D is associated with an increasingly sedentary lifestyle and high-energy food intake of the world's population (P Zimmet, K G M M Alberti & J Shaw, "Global and societal implications of the diabetes epidemic" Nature 2001, 414, 782-787).

β-Cell failure and consequent dramatic decline in insulin secretion and hyperglycemia marks the onset of T2D. Most current treatments do not prevent the loss of β-cell mass characterizing overt T2D. However, recent developments with GLP-1 analogues, gastrin and other agents show that preservation and proliferation of β-cells is possible to achieve, leading to an improved glucose tolerance and slower progression to overt T2D (L L Baggio & D J Drucker, "Therapeutic approaches to preserve islet mass in type 2 diabetes", Annu. Rev. Med. 2006, 57, 265-281).

Tmem27 has been identified as a protein promoting beta-cell proliferation (P Akpinar, S Kuwajima, J Kriitzfeldt, M Stoffel, "Tmem27: A cleaved and shed plasma membrane protein that stimulates pancreatic β cell proliferation", Cell Metab. 2005, 2, 385-397) and insulin secretion (K Fukui, Q Yang, Y Cao, N Takahashi et al., "The HNF-1 target Collectrin controls insulin exocytosis by SNARE complex formation", Cell Metab. 2005, 2, 373-384). Tmem27 is a 42 kDa membrane glycoprotein which is constitutively shed from the surface of β-cells, resulting from a degradation of the full-length cellular Tmem27. Overexpression of Tmem27 in a transgenic mouse increases β-cell mass and improves glucose tolerance in a diet-induced obesity DIO model of diabetes. Furthermore, siRNA knockout of Tmem27 in a rodent β-cell proliferation assay (e.g. using INS1e cells) reduces the proliferation rate, indicating a role for Tmem27 in control of β-cell mass.

In the same proliferation assay, BACE2 inhibitors also increase proliferation. However, BACE2 inhibition combined with Tmem27 siRNA knockdown results in low proliferation rates. Therefore, it is concluded that BACE2 is the protease responsible for the degradation of Tmem27. Furthermore, in vitro, BACE2 cleaves a peptide based on the sequence of Tmem27. The closely related protease BACE1 does not cleave this peptide and selective inhibition of BACE1 alone does not enhance proliferation of β-cells.

The close homolog BACE2 is a membrane-bound aspartyl protease and is co-localized with Tmem27 in human pancreatic β-cells (G Finzi, F Franzi, C Placidi, F Acquati et al., "BACE2 is stored in secretory granules of mouse and rat pancreatic beta cells", Ultrastruct Pathol. 2008, 32(6), 246-251). It is also known to be capable of degrading APP (I Hussain, D Powell, D Howlett, G Chapman et al., "ASP1 (BACE2) cleaves the amyloid precursor protein at the β-secretase site" Mol Cell Neurosci. 2000, 16, 609-619), IL-1R2 (P Kuhn, E Marjaux, A Imhof, B De Strooper et al., "Regulated intramembrane proteolysis of the interleukin-1 receptor II by alpha-, beta-, and gamma-secretase" J. Biol. Chem. 2007, 282(16), 11982-11995) and ACE2. The capability to degrade ACE2 indicates a possible role of BACE2 in the control of hypertension.

Inhibition of BACE2 is therefore proposed as a treatment for T2D with the potential to preserve and restore β-cell mass and stimulate insulin secretion in pre-diabetic and diabetic patients. It is therefore an object of the present invention to provide selective BACE2 inhibitors. Such compounds are useful as therapeutically active substances, particularly in the treatment and/or prevention of diseases which are associated with the inhibition of BACE2.

Furthermore, the formation, or formation and deposition, of β-amyloid peptides in, on or around neurological tissue (e.g., the brain) are inhibited by the present compounds, i.e. inhibition of the Aβ-production from APP or an APP fragment.

Inhibitors of BACE1 and/or BACE2 can in addition be used to treat the following diseases:
IBM (inclusion body myositis) (Vattemi G. et al., Lancet. 2001 Dec. 8; 358(9297):1962-4), Down's Syndrome (Barbiero L. et al, Exp Neurol. 2003 August; 182(2):335-45), Wilson's Disease (Sugimoto I. et al., J Biol Chem. 2007 Nov. 30; 282(48):34896-903), Whipple's disease (Desnues B. et al., Clin Vaccine Immunol. 2006 February; 13(2):170-8), SpinoCerebellar Ataxia 1 and SpinoCerebellar Ataxia 7 (Gatchel J. R. et al., *Proc Natl Acad Sci USA* 2008 Jan. 29; 105(4):1291-6), Dermatomyositis (Greenberg S. A. et al., Ann Neurol. 2005 May; 57(5):664-78 and Greenberg S. A. et al., *Neurol* 2005 May; 57(5):664-78), Kaposi Sarcoma (Lagos D. et al, Blood, 2007 Feb. 15; 109(4):1550-8), Glioblastoma multiforme (E-MEXP-2576, http://www.ebi.ac.uk/microarray-as/aer/result?queryFor=PhysicalArrayDesign&aAccession=A-MEXP-258), Rheumatoid arthritis (Ungethuem U. et al, GSE2053), Amyotrophic lateral sclerosis (Koistinen H. et al., Muscle Nerve. 2006 October; 34(4):444-50 and Li Q. X. et al, Aging Cell. 2006 April; 5(2):153-65), Huntington's Disease (Kim Y. J. et al., Neurobiol Dis. 2006 May; 22(2):346-56. Epub 2006 Jan. 19 and Hodges A. et al., Hum Mol. Genet. 2006 Mar. 15; 15(6):965-77. Epub 2006 Feb. 8), Multiple Mieloma (Kihara Y. et al, Proc Natl Acad Sci USA. 2009 Dec. 22; 106(51):21807-12), Malignant melanoma (Talantov D. et al, Clin Cancer Res. 2005 Oct. 15; 11(20):7234-42), Sjogren syndrome (Basset C. et al., Scand J. Immunol. 2000 March; 51(3):307-11), Lupus erythematosus (Grewal P. K. et al, Mol Cell Biol. 2006, July; 26(13):4970-81), Macrophagic myofasciitis, juvenile idiopathic arthritis, granulomatous arthritis, Breast cancer (Hedlund M. et al, Cancer Res. 2008 Jan. 15; 68(2):388-94 and Kondoh K. et al., Breast Cancer Res Treat. 2003 March; 78(1):37-44), Gastrointestinal diseases (Hoffmeister A. et al, JOP. 2009 Sep. 4; 10(5):501-6), Autoimmune/inflammatory diseases (Woodard-Grice A. V. et al., J Biol. Chem. 2008 Sep. 26; 283(39):26364-73. Epub 2008 Jul. 23), Rheumatoid Arthritis (Toegel S. et al, Osteoarthritis Cartilage. 2010 February; 18(2):240-8. Epub 2009 Sep. 22), Inflammatory reactions (Lichtenthaler S. F. et al., J Biol. Chem. 2003 Dec. 5; 278(49):48713-9. Epub 2003 Sep. 24), Arterial Thrombosis (Merten M. et al., Z Kardiol. 2004 November; 93(11):855-63), Cardiovascular diseases such as Myocardial infarction and stroke (Maugeri N. et al., Srp Arh Celok Lek. 2010 January; 138 Suppl 1:50-2) and Graves disease (Kiljanski J. et al, Thyroid. 2005 July; 15(7):645-52).

FIELD OF THE INVENTION

The present invention relates to 1,4-oxazepines having BACE1 and/or BACE2 inhibitory properties, their manufacture, pharmaceutical compositions containing them and their use as therapeutically active substances.

SUMMARY OF THE INVENTION

The present invention provides novel compounds of formula I, their manufacture, pharmaceutical compositions containing compounds of the invention and their production as well as methods for the control or prevention of illnesses such as Alzheimer's disease and type 2 diabetes. Furthermore, the invention provides methods for the treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease and Wilson's Disease. The novel compounds of formula I have improved pharmacological properties.

The present invention provides a compounds of formula I,

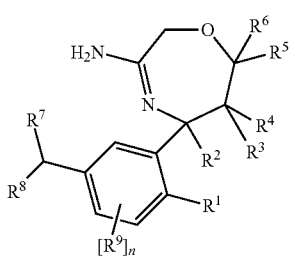

wherein the substituents and variables are as described below and in the claims, or a pharmaceutically acceptable salt thereof.

The present compounds have Asp2 (β-secretase, BACE1 or Memapsin-2) inhibitory activity and may therefore be used in the therapeutic and/or prophylactic treatment of diseases and disorders characterized by elevated β-amyloid levels and/or β-amyloid oligomers and/or β-amyloid plaques and further deposits, particularly Alzheimer's disease. And/or the present compounds have BACE2 inhibitory activity and can therefore be used in the therapeutic and/or prophylactic treatment of diseases and disorders such as type 2 diabetes and other metabolic disorders.

DETAILED DESCRIPTION OF THE INVENTION

The present invention provides a compound of formula I and their pharmaceutically acceptable salts thereof, the preparation of the above mentioned compounds, pharmaceutical compositions containing them and their manufacture as well as methods for the therapeutic and/or prophylactic treatment of diseases and disorders which are associated with inhibition of BACE1 and/or BACE2 activity, such as Alzheimer's disease and type 2 diabetes. Furthermore, the formation, or formation and deposition, of β-amyloid plaques in, on or around neurological tissue (e.g., the brain) are inhibited by the present compounds by inhibiting the Aβ production from APP or an APP fragment.

The following definitions of the general terms used in the present description apply irrespectively of whether the terms in question appear alone or in combination with other groups.

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Optional" or "optionally" means that the subsequently described event or circumstance may, but need not, occur and that the description includes instances where the event or circumstance occurs and instances in which it does not.

The term "$C_{1-6}$-alkyl", alone or in combination with other groups, stands for a hydrocarbon radical which can be linear or branched, with single or multiple branching, wherein the alkyl group in contains 1 to 6 carbon atoms, for example, methyl (Me), ethyl (Et), propyl, isopropyl (i-propyl), n-butyl, i-butyl (isobutyl), 2-butyl (sec-butyl), t-butyl (tert-butyl), isopentyl, 2-ethyl-propyl, 1,2-dimethyl-propyl and the like. Particular "$C_{1-6}$-alkyl" are groups with 1 to 5 carbon atoms. Specific examples are methyl, ethyl and t-butyl—more specifically methyl.

The term "cyano-$C_{1-6}$-alkyl", alone or in combination with other groups, refers to $C_{1-6}$ alkyl as defined herein, which is substituted by one or multiple cyano, in particular 1-5 cyano, more particular 1 cyano. Examples are cyano-methyl and the like.

The term "halogen-$C_{1-6}$-alkyl", alone or in combination with other groups, refers to $C_{1-6}$-alkyl as defined herein, which is substituted by one or multiple halogen atoms, in particular 1-5 halogen atoms, more particular 1-3 halogen atoms ("halogen-$C_{1-3}$-alkyl"), specifically 1 halogen atom or 3 halogen atoms. A particular halogen atom is fluoro. A particular "halogen-$C_{1-6}$-alkyl" is fluoro-$C_{1-6}$-alkyl. Examples are difluoromethyl, chloromethyl, fluoromethyl and the like—specifically trifluoromethyl.

The term "$C_{1-6}$-alkoxy-$C_{1-6}$-alkyl", alone or in combination with other groups, refers to $C_{1-6}$-alkyl, which is substituted by one or multiple $C_{1-6}$-alkoxy as defined herein. Examples are MeO-Me, 1MeO-Et, 2MeO-Et, 1MeO-2EtO-propyl and the like.

The term "$C_{1-6}$-alkyl-NH—SO$_2$—", alone or in combination with other groups, refers to a $C_{1-6}$-alkyl as defined herein linked via —NH—SO$_2$—.

The term "$C_{1-6}$-alkyl-SO$_2$—", alone or in combination with other groups, refers to a $C_{1-6}$-alkyl as defined herein linked via —SO$_2$—.

The term "cyano", alone or in combination with other groups, refers to N≡C—.

The term "benzyl", alone or in combination with other groups, refers to phenyl-CH$_2$—.

The term "halogen", alone or in combination with other groups, denotes chloro (Cl), iodo (I), fluoro (F) and bromo (Br). Particular "halogen" atoms are Cl and F—specifically F.

The term "aryl", alone or in combination with other groups, refers to an aromatic carbocyclic group containing 6 to 14, particularly 6 to 10, carbon atoms and having at least one aromatic ring or multiple condensed rings in which at least one ring is aromatic. Examples of "aryl" include benzyl, biphenyl, indanyl, naphthyl, phenyl (Ph) and the like. A particular "aryl" is phenyl.

The term "halogen-aryl", alone or in combination with other groups, refers to an "aryl" as defined herein substituted by 1, 2 or 3 "halogen" as defined herein. Particular "halogen-aryl" is halogen-phenyl. Specific examples are 2-chloro-phenyl, 3-chloro-phenyl, 2,5-dichloro-phenyl, 3,5-dichloro-phenyl, 3-chloro-4-fluoro-phenyl, 4-fluoro-phenyl, 2,4-difluoro-phenyl, 3,5-difluoro-phenyl and 2,3,5-trichloro-phenyl.

The term "halogen-$C_{1-6}$-alkyl-heteroaryl", alone or in combination with other groups, refers to "heteroaryl" as defined herein substituted by 1 or 2 "halogen-$C_{1-6}$-alkyl" as defined herein. Particular "halogen-$C_{1-6}$-alkyl-heteroaryl" are trifluoromethyl-pyridyl- and trifluoromethyl-benzooxazolyl. Specific examples are 5-trifluoromethyl-pyridin-2-yl- and 6-trifluoromethyl-benzooxazol-2-yl.

The term "heteroaryl", alone or in combination with other groups, refers to an aromatic ring having a single 4 to 8 membered ring or multiple condensed rings containing 6 to 14, in particular 6 to 10, ring atoms and containing 1, 2 or 3 heteroatoms individually selected from N, O and S, in particular N and O, in which group at least one heterocyclic ring is aromatic. Examples of "heteroaryl" include benzofuryl, benzoimidazolyl, 1H-benzoimidazolyl, benzooxazinyl, benzoxazolyl, benzothiazinyl, benzothiazolyl, benzothienyl, benzotriazolyl, furyl, imidazolyl, indazolyl, 1H-indazolyl, indolyl, isoquinolinyl, isothiazolyl, isoxazolyl, oxazolyl, pyrazinyl, pyrazolyl (pyrazyl), 1H-pyrazolyl, pyrazolo[1,5-a]pyridinyl, pyridazinyl, pyridinyl, pyrimidinyl, pyrrolyl, quinolinyl, tetrazolyl, thiazolyl, thienyl, triazolyl, 6,7-dihydro-5H-[1]pyrindinyl and the like. Particular "heteroaryl" are pyrimidinyl-, 1H-pyrazolyl, pyridyl, 1H-imidazolyl, 2H-pyrazolyl, thiazolyl, benzooxazolyl and benzothiazolyl. Specific examples are pyrimidin-5-yl-, 1H-pyrazol-4-yl, pyridin-2-yl-, 1H-imidazol-4-yl, 2H-pyrazol-3-yl, thiazol-4-yl, pyridin-3-yl, pyrimidin-2-yl, benzooxazol-2-yl and benzothiazol-2-yl.

The term "cyano-heteroaryl", alone or in combination with other groups, refers to "heteroaryl" as defined herein substituted by 1 or 2 "cyano" as defined herein. Particular "cyano-heteroaryl" are cyano-pyridinyl and cyano-pyridinyl. Specific examples are-5-cyano-pyridin-2-yl and 4-cyano-pyridin-2-yl.

The term "halogen-heteroaryl", alone or in combination with other groups, refers to "heteroaryl" as defined herein substituted by 1 or 2 "halogen" as defined herein. Particular "halogen-heteroaryl" are chloro-benzooxazolyl, fluoro-benzooxazolyl, chloro-pyrimidinyl, chloro-pyridinyl, chloro-pyridazinyl and halogen-pyridinyl, specific are 5-chloro-benzooxazol-2-yl, 5,6-difluoro-benzooxazol-2-yl, 5-chloro-pyrimidin-2-yl, 2-chloro-pyridin-4-yl, 6-chloro-pyridazin-3-yl and 5-chloro-pyridin-3-yl.

The term "$C_{1-6}$-alkyl-heteroaryl", alone or in combination with other groups, refers to "heteroaryl" as defined herein substituted by 1 or 2 "$C_{1-6}$-alkyl" as defined herein.

The term "$C_{1-6}$-alkoxy-heteroaryl", alone or in combination with other groups, refers to "heteroaryl" as defined herein substituted by 1 or 2 "$C_{1-6}$-alkoxy" as defined herein. Particular "$C_{1-6}$-alkoxy-heteroaryl" is methoxy-pyrazinyl. A specific example is 5-methoxy-pyrazin-2-yl.

The term "heterocyclyl", alone or in combination with other groups, denotes a monovalent saturated or partly unsaturated mono- or bicyclic ring system of 4 to 9 ring atoms, containing 1, 2, or 3 ring heteroatoms selected from N, O and S, the remaining ring atoms being carbon. Bicyclic means consisting of two rings having two ring atoms in common, i.e. the bridge separating the two rings is either a single bond or a chain of one or two ring atoms. Examples for mono cyclic saturated heterocyclyl are azetidinyl, pyrrolidinyl (pyrrolidyl), tetrahydrofuranyl, tetrahydro-thienyl, pyrazolidinyl, imidazolidinyl, oxazolidinyl, isoxazolidinyl, thiazolidinyl, piperidinyl (piperidyl), tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, and oxazepanyl. Examples for bicyclic saturated heterocyclyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, and 3-thia-9-aza-bicyclo[3.3.1]nonyl. Examples for partly unsaturated heterocyclyl are dihydrofuryl, imidazolinyl, dihydro-oxazolyl, tetrahydro-pyridinyl, and dihydropyranyl. Particular "heterocyclyl" are dihydropyranyl and tetrahydropyranyl. Specific examples are 3,6-dihydro-2H-pyran-4-yl and tetrahydro-pyran-4-yl.

The term "$C_{1-6}$-alkoxy", alone or in combination with other groups, stands for an —O—$C_{1-6}$-alkyl radical which can be linear or branched, with single or multiple branching, wherein the alkyl group contains 1 to 6 carbon atoms, for example, methoxy (OMe), ethoxy (OEt), propoxy, isopropoxy (1-propoxy), n-butoxy, i-butoxy (iso-butoxy), 2-butoxy (sec-butoxy), t-butoxy (tert-butoxy), isopentyloxy (i-pentyloxy) and the like. Particular "$C_{1-6}$-alkoxy" are groups with 1 to 4 carbon atoms—specifically methoxy.

The term "halogen-$C_{1-6}$-alkoxy", alone or in combination with other groups, refers to $C_{1-6}$-alkoxy as defined herein, which is substituted by one or multiple halogens, in particular fluoro. Particular "halogen-$C_{1-6}$-alkoxy" is fluoro-$C_{1-6}$-alkoxy. Specific examples are difluoromethoxy and trifluoromethoxy.

The term "$C_{1-6}$-alkoxy-$SO_2$—", alone or in combination with other groups, refers to a $C_{1-6}$-alkoxy as defined herein linked via —$SO_2$—.

The term "$C_{2-6}$-alkynyl", alone or in combination with other groups, denotes a monovalent linear or branched hydrocarbon group of 2 to 6 carbon atoms, in particular from 2 to 4 carbon atoms, and containing one, two or three triple bonds. Examples of $C_{2-6}$-alkynyl include ethynyl, propynyl, prop-2-ynyl and n-butynyl—specifically ethynyl.

The term "pharmaceutically acceptable salts" refers to salts that are suitable for use in contact with the tissues of humans and animals. Examples of suitable salts with inorganic and organic acids are, but are not limited to acetic acid, citric acid, formic acid, fumaric acid, hydrochloric acid, lactic acid, maleic acid, malic acid, methane-sulfonic acid, nitric acid, phosphoric acid, p-toluenesulphonic acid, succinic acid, sulfuric acid, sulphuric acid, tartaric acid, trifluoroacetic acid and the like. Particular are formic acid, trifluoroacetic acid and hydrochloric acid. Particular are hydrochloric acid, trifluoroacetic acid and fumaric acid.

The terms "pharmaceutically acceptable carrier" and "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. Particularly it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

The term "inhibitor" denotes a compound which competes with, reduces or prevents the binding of a particular ligand to particular receptor or which reduces or prevents the inhibition of the function of a particular protein.

The term "half maximal inhibitory concentration" ($IC_{50}$) denotes the concentration of a particular compound required for obtaining 50% inhibition of a biological process in vitro. $IC_{50}$ values can be converted logarithmically to $pIC_{50}$ values (−log $IC_{50}$), in which higher values indicate exponentially greater potency. The $IC_{50}$ value is not an absolute value but depends on experimental conditions e.g. concentrations employed. The $IC_{50}$ value can be converted to an absolute inhibition constant (Ki) using the Cheng-Prusoff equation (Biochem. Pharmacol. (1973) 22:3099). The term "inhibition constant" (Ki) denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values (−log Ki), in which higher values indicate exponentially greater potency.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The term "as defined herein" and "as described herein" when referring to a variable incorporates by reference the broad definition of the variable as well as particularly, more particularly and most particularly definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there can be one or more intermediates which are produced in the mixture which ultimately leads to the formation of the indicated and/or the desired product.

The term "protecting group" denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. The term "amino-protecting group" denotes groups intended to protect an amino group and includes benzyl, benzyloxycarbonyl (carbobenzyloxy, CBZ),9-Fluorenylmethyloxycarbonyl (FMOC), p-methoxybenzyloxycarbonyl, p-nitrobenzyloxycarbonyl, tert-butoxycarbonyl (BOC), and trifluoroacetyl. Further examples of these groups are found in T. W. Greene and P. G. M. Wuts, "Protective Groups in Organic Synthesis", 2nd ed., John Wiley & Sons, Inc., New York, N.Y., 1991, chapter 7; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected amino group" refers to an amino group substituted by an amino-protecting groups. Particular amino-protecting groups are tert-butoxycarbonyl group, a bis(dimethoxyphenyl)-phenylmethyl and dimethoxytrityl.

The term "leaving group" denotes the group with the meaning conventionally associated with it in synthetic organic chemistry, i.e., an atom or group displaceable under substitution reaction conditions. Examples of leaving groups include halogen, in particular bromo, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, and acyloxy.

The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

Whenever a chiral carbon is present in a chemical structure, it is intended that all stereoisomers associated with that chiral carbon are encompassed by the structure.

The invention also provides pharmaceutical compositions, methods of using, and methods of preparing the aforementioned compounds.

All separate embodiments can be combined.

One embodiment of the invention is a compound of formula I,

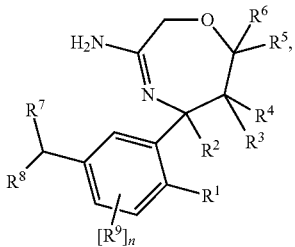

I wherein
$R^1$ is selected from the groups consisting of
hydrogen and
halogen;
$R^2$ is selected from the groups consisting of
$C_{1-6}$-alkyl and
halogen-$C_{1-3}$-alkyl;
$R^3$ is selected from the groups consisting of
hydrogen,
halogen, and
$C_{1-6}$-alkyl;
$R^4$ is selected from the groups consisting of
hydrogen,
halogen, and
$C_{1-6}$-alkyl;
$R^5$ is selected from the groups consisting of
hydrogen and
$C_{1-6}$-alkyl;
$R^6$ is selected from the groups consisting of
hydrogen and
$C_{1-6}$-alkyl;
$R^7$ and $R^8$ together with the C atom to which they are attached form a group selected from the group consisting of
aryl,
aryl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{1-6}$-alkyl-NH—$SO_2$—, $C_{1-6}$-alkyl-$SO_2$—, $C_{1-6}$-alkoxy-$SO_2$— and $C_{1-6}$-alkyl,
heteroaryl,
heteroaryl substituted by 1-4 substituents individually selected from aryl, cyano, cyano-$C_{1-6}$-alkyl, halogen, halogen-$C_{1-6}$-alkoxy, halogen-$C_{1-6}$-alkyl, halogen-$C_{1-6}$-alkyl-heteroaryl, halogen-aryl, heteroaryl, $C_{1-6}$-alkoxy, $C_{1-6}$-alkoxy-$C_{1-6}$-alkyl, $C_{1-6}$-alkyl-NH—$SO_2$— and $C_{1-6}$-alkyl,
$C_{2-6}$-alkynyl,
$C_{2-6}$-alkynyl substituted by 1-5 substituents individually selected from aryl, cyano, halogen-aryl, halogen, $C_{1-6}$-alkyl, $C_{1-6}$-alkyl-aryl, cyano-heteroaryl, halogen-heteroaryl, $C_{1-6}$-alkyl-heteroaryl, heteroaryl, $C_{1-6}$-alkoxy-heteroaryl and $C_{1-6}$-alkoxy;
heterocyclyl, and
heterocyclyl substituted by 1-4 substituents individually selected from halogen, halogen-$C_{1-6}$-alkoxy, halogen-$C_{1-6}$-alkyl, $C_{1-6}$-alkoxy, $C_{1-6}$-alkoxy-$C_{1-6}$-alkyl and $C_{1-6}$-alkyl;
$R^9$ is selected from the group consisting of
halogen, and
$C_{1-6}$-alkyl; and
n is 0 or 1;
or pharmaceutically acceptable salts thereof.

A certain embodiment of the invention is a compound of formula I wherein
$R^1$ is selected from the groups consisting of
hydrogen and
halogen;
$R^2$ is selected from the groups consisting of
$C_{1-6}$-alkyl and
halogen-$C_{1-3}$-alkyl;
$R^3$ is selected from the groups consisting of
hydrogen,
halogen, and
$C_{1-6}$-alkyl;
$R^4$ is selected from the groups consisting of
hydrogen,
halogen, and
$C_{1-6}$-alkyl;
$R^5$ is selected from the groups consisting of
hydrogen and
$C_{1-6}$-alkyl;
$R^6$ is selected from the groups consisting of hydrogen and
$C_{1-6}$-alkyl;
$R^7$ and $R^8$ together with the C atom to which they are attached form a group selected from the group consisting of
aryl,
aryl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{1-6}$-alkyl-NH—$SO_2$—, $C_{1-6}$-alkyl-$SO_2$—, $C_{1-6}$-alkoxy-$SO_2$— and $C_{1-6}$-alkyl,
heteroaryl,
heteroaryl substituted by 1-4 substituents individually selected from aryl, cyano, cyano-$C_{1-6}$-alkyl, halogen, halogen-$C_{1-6}$-alkoxy, halogen-$C_{1-6}$-alkyl, halogen-$C_{1-6}$-alkyl-heteroaryl, halogen-aryl, heteroaryl, $C_{1-6}$-alkoxy, $C_{1-6}$-alkoxy-$C_{1-6}$-alkyl, $C_{1-6}$-alkyl-NH—$SO_2$— and $C_{1-6}$-alkyl,
$C_{2-6}$-alkynyl,
$C_{2-6}$-alkynyl substituted by 1-5 substituents individually selected from aryl, cyano, halogen-aryl, halogen, $C_{1-6}$-alkyl, $C_{1-6}$-alkyl-aryl, $C_{1-6}$-alkyl-heteroaryl and $C_{1-6}$-alkoxy;
heterocyclyl, and
heterocyclyl substituted by 1-4 substituents individually selected from halogen, halogen-$C_{1-6}$-alkoxy, halogen-$C_{1-6}$-alkyl, $C_{1-6}$-alkoxy, $C_{1-6}$-alkoxy-$C_{1-6}$-alkyl and $C_{1-6}$-alkyl;
$R^9$ is selected from the group consisting of
halogen and
$C_{1-6}$-alkyl; and
n is 0 or 1;
or pharmaceutically acceptable salts thereof.

A certain embodiment of the invention provides a compound as defined herein, wherein
$R^1$ is halogen;
$R^2$ is $C_{1-6}$-alkyl;
$R^3$ is halogen;
$R^4$ is halogen;
$R^5$ is selected from the groups consisting of
Hydrogen and
$C_{1-6}$-alkyl;
$R^6$ is selected from the groups consisting of
hydrogen and
$C_{1-6}$-alkyl;
$R^7$ and $R^8$ together with the C atom to which they are attached form a group selected from the group consisting of
aryl substituted by 1-2 substituents individually selected from cyano, halogen, $C_{1-6}$-alkyl-NH—$SO_2$—, and $C_{1-6}$-alkoxy-$SO_2$,
heteroaryl,
heteroaryl substituted by 1-2 substituents individually selected from halogen, halogen-$C_{1-6}$-alkyl-heteroaryl, halogen-aryl, heteroaryl, $C_{1-6}$-alkoxy and $C_{1-6}$-alkyl,
$C_{2-6}$-alkynyl substituted by 1-2 substituents individually selected from halogen-aryl and $C_{1-6}$-alkyl-heteroaryl; and
Heterocyclyl;
$R^9$ is halogen; and
n is 0 or 1.

A certain embodiment of the invention provides a compound as defined herein, wherein $R^1$ is halogen.

A certain embodiment of the invention provides a compound as defined herein, wherein $R^1$ is F.

A certain embodiment of the invention provides a compound as defined herein, wherein $R^2$ is $C_{1-6}$-alkyl.

A certain embodiment of the invention provides a compound as defined herein, wherein $R^2$ is methyl.

A certain embodiment of the invention provides a compound as defined herein, wherein $R^3$ is halogen.

A certain embodiment of the invention provides a compound as defined herein, wherein $R^3$ is F.

A certain embodiment of the invention provides a compound as defined herein, wherein $R^4$ is halogen.

A certain embodiment of the invention provides a compound as defined herein, wherein $R^4$ is F.

A certain embodiment of the invention provides a compound as defined herein, wherein $R^3$ and $R^4$ are halogen.

A certain embodiment of the invention provides a compound as defined herein, wherein $R^3$ and $R^4$ are F.

A certain embodiment of the invention provides a compound as defined herein, wherein $R^5$ is $C_{1-6}$-alkyl.

A certain embodiment of the invention provides a compound as defined herein, wherein $R^5$ is methyl.

A certain embodiment of the invention provides a compound as defined herein, wherein $R^5$ is hydrogen.

A certain embodiment of the invention provides a compound as defined herein, wherein $R^6$ is $C_{1-6}$-alkyl.

A certain embodiment of the invention provides a compound as defined herein, wherein $R^6$ is methyl.

A certain embodiment of the invention provides a compound as defined herein, wherein $R^6$ is hydrogen.

A certain embodiment of the invention provides a compound as defined herein, wherein $R^5$ and $R^6$ are hydrogen.

A certain embodiment of the invention provides a compound as defined herein, wherein $R^5$ and $R^6$ are $C_{1-6}$-alkyl.

A certain embodiment of the invention provides a compound as defined herein, wherein $R^5$ and $R^6$ are methyl.

A certain embodiment of the invention provides a compound as defined herein, wherein $R^3$ and $R^4$ are halogen and $R^5$ and $R^6$ are hydrogen.

A certain embodiment of the invention provides a compound as defined herein, wherein $R^3$ and $R^4$ are F and $R^5$ and $R^6$ are hydrogen.

A certain embodiment of the invention provides a compound as defined herein, wherein $R^1$ is halogen, $R^2$ is $C_{1-6}$-alkyl, $R^3$ and $R^4$ are halogen and $R^5$ and $R^6$ are hydrogen.

A certain embodiment of the invention provides a compound as defined herein, wherein $R^1$ is F, $R^2$ is methyl, $R^3$ and $R^4$ are F and $R^5$ and $R^6$ are hydrogen.

A certain embodiment of the invention provides a compound as defined herein, wherein $R^3$ and $R^4$ are halogen $R^5$ and $R^6$ are $C_{1-6}$-alkyl.

A certain embodiment of the invention provides a compound as defined herein, wherein $R^3$ and $R^4$ are F $R^5$ and $R^6$ are methyl.

A certain embodiment of the invention provides a compound as defined herein, wherein $R^1$ is halogen, $R^2$ is $C_{1-6}$-alkyl, $R^3$ and $R^4$ are halogen and $R^5$ and $R^6$ are $C_{1-6}$-alkyl.

A certain embodiment of the invention provides a compound as defined herein, wherein $R^1$ is F, $R^2$ is methyl, $R^3$ and $R^4$ are F and $R^5$ and $R^6$ are methyl.

A certain embodiment of the invention provides a compound as defined herein, wherein $R^9$ is halogen and n is 1.

A certain embodiment of the invention provides a compound as defined herein, wherein $R^9$ is F and n is 1

A certain embodiment of the invention provides a compound as defined herein, wherein n is 0.

A certain embodiment of the invention provides a compound as defined herein, wherein $R^7$ and $R^8$ form together with the C to which they are attached a group selected from the groups consisting of 1-(4-fluoro-phenyl)-1H-pyrazol-4-yl, 1-(3-chloro-phenyl)-1H-pyrazol-4-yl, 1-pyridin-2-yl-1H-imidazol-4-yl, 2-methyl-2H-pyrazol-3-yl, 2-isopentoxy-$SO_2$-phenyl, 2-fluoro-5-cyano-phenyl, 2-t-butyl-NH$SO_2$-phenyl, 2-t-butyl-NH$SO_2$-pyridin-3-yl, 2-methyl-thiazol-4-ylethynyl, 2-methoxy-pyrimidin-5-yl, 2-chloro-pyridin-4-ylethynyl, 3-chloro-phenylethynyl, 3-fluoro-5-chloro-phenyl, 3-cyano-phenyl, 3-chloro-phenylethynyl, 3,5- difluoro-phenyl, 3,5-dichloro-phenyl, 3,6-dihydro-2H-pyran-4-yl, 4-cyano-phenyl, 4-cyano-pyridin-2-ylethynyl, 5-trifluoromethyl-pyridin-2-yl-1H-imidazol-4-yl, 5-chloro-pyridin-3-yl, 5-chloro-pyrimidin-2-yl, 5-cyano-pyridin-2-ylethynyl, 5-chloro-pyrimidin-2-ylethynyl, 5-chloro-pyridin-3-ylethynyl, 5-pyridin-2-ylethynyl, 5-methoxy-pyrazin-2-ylethynyl, 5,6-difluoro-benzo oxazol-2-yl, 6-chloro-benzothiazol-2-yl, 6-chloro-benzooxazol-2-yl, 6-chloro-pyridazin-3-ylethynyl, 6-trifluoromethyl-benzooxazol-2-yl, pyrimidin-5-yl- and tetrahydro-pyran-4-yl.

A certain embodiment of the invention provides a compound as defined herein, wherein $R^7$ and $R^8$ form together with the C to which they are attached a group selected from the groups consisting of
aryl substituted by 1-2 substituents individually selected from cyano and halogen, heteroaryl, and
heteroaryl substituted by 1-2 substituents individually selected from halogen.

A certain embodiment of the invention provides a compound as defined herein, wherein $R^7$ and $R^8$ form together with the C to which they are attached an aryl substituted by 1-2 substituents individually selected from cyano and halogen.

A certain embodiment of the invention provides a compound as defined herein, wherein $R^7$ and $R^8$ form together with the C to which they are attached an heteroaryl.

A certain embodiment of the invention provides a compound as defined herein, wherein $R^7$ and $R^8$ form together with the C to which they are attached an heteroaryl substituted by 1-2 substituents individually selected from halogen.

A certain embodiment of the invention provides a compound as defined herein, wherein $R^7$ and $R^8$ form together with the C to which they are attached a group selected from the groups consisting of phenyl substituted by halogen and cyano, pyrimidyl and pyridinyl substituted by halogen.

A certain embodiment of the invention provides a compound as defined herein, wherein $R^7$ and $R^8$ form together with the C to which they are attached a group selected from the groups consisting of pyrimidin-5-yl, 2-fluoro-5-cyano-phenyl and 5-chloro-pyridin-3-yl.

A certain embodiment of the invention provides a compound as defined herein, wherein $R^7$ and $R^8$ together with the C atom to which they are attached form a group selected from the groups consisting of
phenyl substituted by 1-2 substituents individually selected from halogen, $C_{1-6}$-alkoxy-$SO_2$—, $C_{1-6}$-alkyl-NH—$SO_2$— and cyano, pyrimidinyl, pyrimidinyl substituted by 1-2 substituents individually selected from halogen and $C_{1-6}$-alkoxy, pyridinyl substituted by 1-2 substituents individually selected from halogen, 3,6-dihydro-2H-pyranyl,
1H-pyrazolyl substituted by 1-2 substituents individually selected from halogen-phenyl and $C_{1-6}$-alkyl, tetrahydro-pyranyl, ethynyl substituted by 1-2 substituents individually selected from halogen-phenyl and halogen-thiazolyl, benzooxazolyl substituted by 1-2 substituents individually selected from halogen, benzothiazolyl substituted by 1-2 substituents individually selected from halogen, and 1H-imidazolyl substituted by 1-2 substituents individually selected from pyridinyl and halogen-$C_{1-6}$-alkyl-pyridinyl.

A certain embodiment of the invention provides a compound as defined herein, wherein $R^7$ and $R^8$ together with the C atom to which they are attached form a phenyl substituted by 1-2 substituents individually selected from halogen, $C_{1-6}$-alkoxy-$SO_2$—, $C_{1-6}$-alkyl-NH—$SO_2$— and cyano.

A certain embodiment of the invention provides a compound as defined herein, wherein $R^7$ and $R^8$ together with the C atom to which they are attached form a pyrimidinyl.

A certain embodiment of the invention provides a compound as defined herein, wherein $R^7$ and $R^8$ together with the C atom to which they are attached form a pyrimidinyl substituted by 1-2 substituents individually selected from halogen and $C_{1-6}$-alkoxy.

A certain embodiment of the invention provides a compound as defined herein, wherein $R^7$ and $R^8$ together with the C atom to which they are attached form a pyridinyl substituted by 1-2 substituents individually selected from halogen.

A certain embodiment of the invention provides a compound as defined herein, wherein $R^7$ and $R^8$ form together with the C to which they are attached a 3,6-dihydro-2H-pyranyl.

A certain embodiment of the invention provides a compound as defined herein, wherein $R^7$ and $R^8$ form together with the C to which they are attached a 1H-pyrazolyl substituted by 1-2 substituents individually selected from halogen-phenyl and $C_{1-6}$-alkyl.

A certain embodiment of the invention provides a compound as defined herein, wherein $R^7$ and $R^8$ together with the C atom to which they are attached form a tetrahydro-pyranyl.

A certain embodiment of the invention provides a compound as defined herein, wherein $R^7$ and $R^8$ together with the C atom to which they are attached form a ethynyl substituted by 1-2 substituents individually selected from halogen-phenyl and halogen-thiazolyl.

A certain embodiment of the invention provides a compound as defined herein, wherein $R^7$ and $R^8$ together with the C atom to which they are attached form a ethynyl substituted by 1-2 substituents individually selected from cyano-pyridinyl, halogen-pyridinyl, halogen-pyrimidinyl, halogen-pyridazinyl, $C_{1-6}$-alkoxy-pyridazinyl and pyridinyl.

A certain embodiment of the invention provides a compound as defined herein, wherein $R^7$ and $R^8$ together with the C atom to which they are attached form a benzooxazolyl substituted by 1-2 substituents individually selected from halogen.

A certain embodiment of the invention provides a compound as defined herein, wherein $R^7$ and $R^8$ together with the C atom to which they are attached form a benzooxazolyl substituted by 1-2 substituents individually selected from halogen-$C_{1-6}$-alkyl.

A certain embodiment of the invention provides a compound as defined herein, wherein $R^7$ and $R^8$ together with the C atom to which they are attached form a benzothiazolyl substituted by 1-2 substituents individually selected from halogen.

A certain embodiment of the invention provides a compound as defined herein, wherein $R^7$ and $R^8$ together with the C atom to which they are attached form a 1H-imidazolyl substituted by 1-2 substituents individually selected from pyridinyl and halogen-$C_{1-6}$-alkyl-pyridinyl.

A certain embodiment of the invention provides a compound as defined herein, wherein $R^7$ and $R^8$ together with the C atom to which they are attached form a group selected from the groups consisting of pyrimidin-5-yl, 1-(3-chloro-phenyl)-1H-pyrazol-4-yl, 1-(4-fluoro-phenyl)-1H-pyrazol-4-yl, 1-pyridin-2-yl-1H-imidazol-4-yl, 2-fluoro-5-cyano-phenyl, 2-isopentoxy-$SO_2$-phenyl, 2-methoxy-pyrimidin-5-yl, 2-methyl-2H-pyrazol-3-yl, 2-methyl-thiazol-4-yl-ethynyl, 2-t-butyl-NH$SO_2$-phenyl, 2-t-butyl-NH$SO_2$-pyridin-3-yl, 3,5-dichloro-phenyl, 3,5-di-fluoro-phenyl, 3,6-dihydro-2H-pyran-4-yl, 3-chloro-phenyl-ethynyl, 3-cyano-phenyl, 3-fluoro-5-chloro-phenyl, 4-cyano-phenyl, 5-chloro-pyridin-3-yl, 5-chloro-pyrimidin-2-yl, 5-trifluoro methyl-pyridin-2-yl- 1H-imidazol-4-yl, 6-chloro-benzooxazol-2-yl, 6-chloro-benzothiazol-2-yl, pyrimidin-5-yl- and tetrahydro-pyran-4-yl.

A certain embodiment of the invention provides a compound as defined herein, wherein $R^7$ and $R^8$ together with the C atom to which they are attached form pyrimidin-5-yl.

A certain embodiment of the invention provides a compound as defined herein, wherein $R^7$ and $R^8$ together with the C atom to which they are attached form 1-(3-chloro-phenyl)-1H-pyrazol-4-yl.

A certain embodiment of the invention provides a compound as defined herein, wherein $R^7$ and $R^8$ together with the C atom to which they are attached form 1-(4-fluoro-phenyl)-1H-pyrazol-4-yl.

A certain embodiment of the invention provides a compound as defined herein, wherein $R^7$ and $R^8$ together with the C atom to which they are attached form 1-pyridin-2-yl-1H-imidazol-4-yl.

A certain embodiment of the invention provides a compound as defined herein, wherein $R^7$ and $R^8$ together with the C atom to which they are attached form 2-fluoro-5-cyano-phenyl.

A certain embodiment of the invention provides a compound as defined herein, wherein $R^7$ and $R^8$ together with the C atom to which they are attached form 2-isopentoxy-$SO_2$-phenyl.

A certain embodiment of the invention provides a compound as defined herein, wherein $R^7$ and $R^8$ together with the C atom to which they are attached form 2-methoxy-pyrimidin-5-yl.

A certain embodiment of the invention provides a compound as defined herein, wherein $R^7$ and $R^8$ together with the C atom to which they are attached form 2-methyl-2H-pyrazol-3-yl.

A certain embodiment of the invention provides a compound as defined herein, wherein $R^7$ and $R^8$ together with the C atom to which they are attached form 2-methyl-thiazol-4-yl-ethynyl.

A certain embodiment of the invention provides a compound as defined herein, wherein $R^7$ and $R^8$ together with the C atom to which they are attached form 2-t-butyl-$NHSO_2$-phenyl.

A certain embodiment of the invention provides a compound as defined herein, wherein $R^7$ and $R^8$ together with the C atom to which they are attached form 2-t-butyl-$NHSO_2$-pyridin-3-yl.

A certain embodiment of the invention provides a compound as defined herein, wherein $R^7$ and $R^8$ together with the C atom to which they are attached form 3,5-di-chloro-phenyl.

A certain embodiment of the invention provides a compound as defined herein, wherein $R^7$ and $R^8$ together with the C atom to which they are attached form 3,5-di-fluoro-phenyl.

A certain embodiment of the invention provides a compound as defined herein, wherein $R^7$ and $R^8$ together with the C atom to which they are attached form 3,6-dihydro-2H-pyran-4-yl.

A certain embodiment of the invention provides a compound as defined herein, wherein $R^7$ and $R^8$ together with the C atom to which they are attached form 3-chloro-phenyl-ethynyl.

A certain embodiment of the invention provides a compound as defined herein, wherein $R^7$ and $R^8$ together with the C atom to which they are attached form 3-cyano-phenyl.

A certain embodiment of the invention provides a compound as defined herein, wherein $R^7$ and $R^8$ together with the C atom to which they are attached form 3-fluoro-5-chloro-phenyl.

A certain embodiment of the invention provides a compound as defined herein, wherein $R^7$ and $R^8$ together with the C atom to which they are attached form 4-cyano-phenyl.

A certain embodiment of the invention provides a compound as defined herein, wherein $R^7$ and $R^8$ together with the C atom to which they are attached form 5-chloro-pyridin-3-yl.

A certain embodiment of the invention provides a compound as defined herein, wherein $R^7$ and $R^8$ together with the C atom to which they are attached form 5-chloro-pyrimidin-2-yl.

A certain embodiment of the invention provides a compound as defined herein, wherein $R^7$ and $R^8$ together with the C atom to which they are attached form 5-trifluoromethyl-pyridin-2-yl-1H-imidazol-4-yl.

A certain embodiment of the invention provides a compound as defined herein, wherein $R^7$ and $R^8$ together with the C atom to which they are attached form 6-chloro-benzooxazol-2-yl.

A certain embodiment of the invention provides a compound as defined herein, wherein $R^7$ and $R^8$ together with the C atom to which they are attached form 6-chloro-benzothiazol-2-yl.

A certain embodiment of the invention provides a compound as defined herein, wherein $R^7$ and $R^8$ together with the C atom to which they are attached form pyrimidin-5-yl.

A certain embodiment of the invention provides a compound as defined herein, wherein $R^7$ and $R^8$ together with the C atom to which they are attached form tetrahydro-pyran-4-yl.

A certain embodiment of the invention provides a compound as defined herein, wherein $R^7$ and $R^8$ together with the C atom to which they are attached form 2-chloro-pyridin-4-ylethynyl.

A certain embodiment of the invention provides a compound as defined herein, wherein $R^7$ and $R^8$ together with the C atom to which they are attached form 4-cyano-pyridin-2-ylethynyl.

A certain embodiment of the invention provides a compound as defined herein, wherein $R^7$ and $R^8$ together with the C atom to which they are attached form 5-cyano-pyridin-2-ylethynyl.

A certain embodiment of the invention provides a compound as defined herein, wherein $R^7$ and $R^8$ together with the C atom to which they are attached form 5-chloro-pyrimidin-2-ylethynyl.

A certain embodiment of the invention provides a compound as defined herein, wherein $R^7$ and $R^8$ together with the C atom to which they are attached form 5-chloro-pyridin-3-ylethynyl.

A certain embodiment of the invention provides a compound as defined herein, wherein $R^7$ and $R^8$ together with the C atom to which they are attached form 5-pyridin-2-ylethynyl.

A certain embodiment of the invention provides a compound as defined herein, wherein $R^7$ and $R^8$ together with the C atom to which they are attached form 5-methoxy-pyrazin-2-ylethynyl.

A certain embodiment of the invention provides a compound as defined herein, wherein $R^7$ and $R^8$ together with the C atom to which they are attached form 5-chloro-benzooxazol-2-yl.

A certain embodiment of the invention provides a compound as defined herein, wherein $R^7$ and $R^8$ together with the C atom to which they are attached form 6-chloro-pyridazin-3-ylethynyl.

A certain embodiment of the invention provides a compound as defined herein, wherein $R^7$ and $R^8$ together with the C atom to which they are attached form 6-trifluoromethyl-benzooxazol-2-yl.

A certain embodiment of the invention provides a compound as defined herein, wherein $R^7$ and $R^8$ together with the C atom to which they are attached form 5,6-difluoro-benzooxazol-2-yl.

A certain embodiment of the invention provides a compound as defined herein, selected from the group consisting of
(R)-6,6-Difluoro-5-(2-fluoro-5-pyrimidin-5-yl-phenyl)-5-methyl-2,5,6,7-tetrahydro-[1,4]oxazepin-3-ylamine,
(R)-5-{5-[1-(3-Chloro-phenyl)-1H-pyrazol-4-yl]-2-fluoro-phenyl}-6,6-difluoro-5,7,7-trimethyl-2,5,6,7-tetrahydro-[1,4]oxazepin-3-ylamine,
3'-((R)-3-Amino-6,6-difluoro-5,7,7-trimethyl-2,5,6,7-tetrahydro-[1,4]oxazepin-5-yl)-4'-fluoro-biphenyl-3-sulfonic acid 2,2-dimethyl-propyl ester,
3'-((R)-3-Amino-6,6-difluoro-5,7,7-trimethyl-2,5,6,7-tetrahydro-[1,4]oxazepin-5-yl)-6,4'-difluoro-biphenyl-3-carbonitrile,
3'-((R)-3-Amino-6,6-difluoro-5,7,7-trimethyl-2,5,6,7-tetrahydro-[1,4]oxazepin-5-yl)-4'-fluoro-biphenyl-3-carbonitrile,
3'-((R)-3-Amino-6,6-difluoro-5,7,7-trimethyl-2,5,6,7-tetrahydro-[1,4]oxazepin-5-yl)-4'-fluoro-biphenyl-3-sulfonic acid tert-butylamide,
5-[3-((R)-3-Amino-6,6-difluoro-5,7,7-trimethyl-2,5,6,7-tetrahydro-[1,4]oxazepin-5-yl)-4-fluoro-phenyl]-pyridine-3-sulfonic acid tert-butylamide,
3'-((R)-3-Amino-6,6-difluoro-5,7,7-trimethyl-2,5,6,7-tetrahydro-[1,4]oxazepin-5-yl)-4'-fluoro-biphenyl-4-carbonitrile,
5'-((R)-3-Amino-6,6-difluoro-5,7,7-trimethyl-2,5,6,7-tetrahydro-[1,4]oxazepin-5-yl)-2',4'-difluoro-biphenyl-4-carbonitrile,
5'-((R)-3-Amino-6,6-difluoro-5,7,7-trimethyl-2,5,6,7-tetrahydro-[1,4]oxazepin-5-yl)-2',4'-difluoro-biphenyl-3-carbonitrile,
6-[3-((R)-3-Amino-6,6-difluoro-5,7,7-trimethyl-2,5,6,7-tetrahydro-[1,4]oxazepin-5-yl)-4-fluoro-phenylethynyl]-nicotinonitrile,
2-[3-((R)-3-Amino-6,6-difluoro-5,7,7-trimethyl-2,5,6,7-tetrahydro-[1,4]oxazepin-5-O-4-fluoro-phenylethynyl]-isonicotinonitrile,
(R)-6,6-Difluoro-5-(2-fluoro-5-pyrimidin-5-yl-phenyl)-5,7,7-trimethyl-2,5,6,7-tetrahydro-[1,4]oxazepin-3-ylamine,
(R)-5-(3',5'-Dichloro-4-fluoro-biphenyl-3-yl)-6,6-difluoro-5,7,7-trimethyl-2,5,6,7-tetrahydro-[1,4]oxazepin-3-ylamine,
(R)-5-(5'-Chloro-4,3'-difluoro-biphenyl-3-yl)-6,6-difluoro-5,7,7-trimethyl-2,5,6,7-tetrahydro-[1,4]oxazepin-3-ylamine,
(R)-5-(2,4-Difluoro-5-pyrimidin-5-yl-phenyl)-6,6-difluoro-5,7,7-trimethyl-2,5,6,7-tetrahydro-[1,4]oxazepin-3-ylamine,
(R)-6,6-Difluoro-5-(2-fluoro-5-pyridin-2-ylethynyl-phenyl)-5,7,7-trimethyl-2,5,6,7-tetrahydro-[1,4]oxazepin-3-ylamine,
(R)-6,6-Difluoro-5,7,7-trimethyl-5-(4,3',5'-trifluoro-biphenyl-3-yl)-2,5,6,7-tetrahydro-[1,4]oxazepin-3-ylamine,
(R)-5-{2,4-Difluoro-5-[1-(4-fluoro-phenyl)-1H-pyrazol-4-yl]-phenyl}-6,6-difluoro-5,7,7-trimethyl-2,5,6,7-tetrahydro-[1,4]oxazepin-3-ylamine,
(R)-5-[2,4-Difluoro-5-(6-trifluoromethyl-benzooxazol-2-yl)-phenyl]-6,6-difluoro-5,7,7-trimethyl-2,5,6,7-tetrahydro-[1,4]oxazepin-3-ylamine,
(R)-5-[5-(5-Chloro-pyridin-3-yl)-2-fluoro-phenyl]-6,6-difluoro-5,7,7-trimethyl-2,5,6,7-tetrahydro-[1,4]oxazepin-3-ylamine,
(R)-6,6-Difluoro-5-{2-fluoro-5-[1-(4-fluoro-phenyl)-1H-pyrazol-4-yl]-phenyl}-5,7,7-trimethyl-2,5,6,7-tetrahydro-[1,4]oxazepin-3-ylamine,
(R)-6,6-Difluoro-5-[2-fluoro-5-(2-methyl-2H-pyrazol-3-yl)-phenyl]-5,7,7-trimethyl-2,5,6,7-tetrahydro-[1,4]oxazepin-3-ylamine,
(R)-6,6-Difluoro-5-[2-fluoro-5-(tetrahydro-pyran-4-yl)-phenyl]-5,7,7-trimethyl-2,5,6,7-tetrahydro-[1,4]oxazepin-3-ylamine,
(R)-5-[5-(3-Chloro-phenylethynyl)-2-fluoro-phenyl]-6,6-difluoro-5,7,7-trimethyl-2,5,6,7-tetrahydro-[1,4]oxazepin-3-ylamine,
(R)-6,6-Difluoro-5-[2-fluoro-5-(2-methyl-thiazol-4-ylethynyl)-phenyl]-5,7,7-trimethyl-2,5,6,7-tetrahydro-[1,4]oxazepin-3-ylamine,
(R)-5-[5-(6-Chloro-benzooxazol-2-yl)-2-fluoro-phenyl]-6,6-difluoro-5,7,7-trimethyl-2,5,6,7-tetrahydro-[1,4]oxazepin-3-ylamine,
(R)-5-[5-(6-Chloro-benzothiazol-2-yl)-2-fluoro-phenyl]-6,6-difluoro-5,7,7-trimethyl-2,5,6,7-tetrahydro-[1,4]oxazepin-3-ylamine,
(R)-6,6-Difluoro-5-[2-fluoro-5-(1-pyridin-2-yl-1H-imidazol-4-yl)-phenyl]-5,7,7-trimethyl-2,5,6,7-tetrahydro-[1,4]oxazepin-3-ylamine,
(R)-6,6-Difluoro-5-{2-fluoro-5-[1-(5-trifluoromethyl-pyridin-2-yl)-1H-imidazol-4-yl]-phenyl}-5,7,7-trimethyl-2,5,6,7-tetrahydro-[1,4]oxazepin-3-ylamine,
(R)-5-[5-(3-Chloro-phenylethynyl)-2,4-difluoro-phenyl]-6,6-difluoro-5,7,7-trimethyl-2,5,6,7-tetrahydro-[1,4]oxazepin-3-ylamine,
(R)-5-[5-(5-Chloro-pyridin-3-yl)-2,4-difluoro-phenyl]-6,6-difluoro-5,7,7-trimethyl-2,5,6,7-tetrahydro-[1,4]oxazepin-3-ylamine,
(R)-5-[5-(6-Chloro-benzooxazol-2-yl)-2,4-difluoro-phenyl]-6,6-difluoro-5,7,7-trimethyl-2,5,6,7-tetrahydro-[1,4]oxazepin-3-ylamine,
(R)-5-[5-(5-Chloro-pyrimidin-2-yl)-2,4-difluoro-phenyl]-6,6-difluoro-5,7,7-trimethyl-2,5,6,7-tetrahydro-[1,4]oxazepin-3-ylamine,
(R)-5-[5-(5-Chloro-pyrimidin-2-ylethynyl)-2-fluoro-phenyl]-6,6-difluoro-5,7,7-trimethyl-2,5,6,7-tetrahydro-[1,4]oxazepin-3-ylamine,
(R)-5-[5-(2-Chloro-pyridin-4-ylethynyl)-2-fluoro-phenyl]-6,6-difluoro-5,7,7-trimethyl-2,5,6,7-tetrahydro-[1,4]oxazepin-3-ylamine,
(R)-5-[5-(6-Chloro-pyridazin-3-ylethynyl)-2-fluoro-phenyl]-6,6-difluoro-5,7,7-trimethyl-2,5,6,7-tetrahydro-[1,4]oxazepin-3-ylamine,
(R)-5-[5-(5-Chloro-pyridin-3-ylethynyl)-2-fluoro-phenyl]-6,6-difluoro-5,7,7-trimethyl-2,5,6,7-tetrahydro-[1,4]oxazepin-3-ylamine,
(R)-6,6-Difluoro-5-[2-fluoro-5-(5-methoxy-pyrazin-2-ylethynyl)-phenyl]-5,7,7-trimethyl-2,5,6,7-tetrahydro-[1,4]oxazepin-3-ylamine,
(R)-5-[5-(5-Chloro-benzooxazol-2-yl)-2,4-difluoro-phenyl]-6,6-difluoro-5,7,7-trimethyl-2,5,6,7-tetrahydro-[1,4]oxazepin-3-ylamine,
(R)-5-[2,4-Difluoro-5-(2-methoxy-pyrimidin-5-yl)-phenyl]-6,6-difluoro-5,7,7-trimethyl-2,5,6,7-tetrahydro-[1,4]oxazepin-3-ylamine,
(R)-5-[5-(3,6-Dihydro-2H-pyran-4-yl)-2-fluoro-phenyl]-6,6-difluoro-5,7,7-trimethyl-2,5,6,7-tetrahydro-[1,4]oxazepin-3-ylamine, and (R)-5-[5-(5,6-Difluoro-benzooxazol-2-yl)-2,4-difluoro-phenyl]-6,6-difluoro-5,7,7-trimethyl-2,5,6,7-tetrahydro-[1,4] oxazepin-3-ylamine, or pharmaceutically acceptable salts thereof.

A certain embodiment of the invention provides a compound as defined herein, selected from the group consisting of (R)-6,6-Difluoro-5-(2-fluoro-5-pyrimidin-5-yl-phenyl)-5-methyl-2,5,6,7-tetrahydro-[1,4]oxazepin-3-ylamine, (R)-5-(2,4-Difluoro-5-pyrimidin-5-yl-phenyl)-6,6-difluoro-5,7,7-trimethyl-2,5,6,7-tetrahydro-[1,4]oxazepin-3-ylamine, (R)-5-(3',5'-Dichloro-4-fluoro-biphenyl-3-yl)-6,6-difluoro-5,7,7-trimethyl-2,5,6,7-tetrahydro-[1,4]oxazepin-3-ylamine, (R)-5-(5'-Chloro-4,3'-difluoro-biphenyl-3-yl)-6,6-difluoro-5,7,7-trimethyl-2,5,6,7-tetrahydro-[1,4]oxazepin-3-ylamine, (R)-5-[2,4-Difluoro-5-(2-methoxy-pyrimidin-5-yl)-phenyl]-6,6-difluoro-5,7,7-trimethyl-2,5,6,7-tetrahydro-[1,4]oxazepin-3-ylamine, (R)-5-[5-(3,6-Dihydro-2H-pyran-4-yl)-2-fluoro-phenyl]-6,6-difluoro-5,7,7-trimethyl-2,5,6,7-tetrahydro-[1,4]oxazepin-3-ylamine, (R)-5-[5-(3-Chloro-phenylethynyl)-2,4-difluoro-phenyl]-6,6-difluoro-5,7,7-trimethyl-2,5,6,7-tetrahydro-[1,4]oxazepin-3-ylamine, (R)-5-[5-(3-Chloro-phenylethynyl)-2-fluoro-phenyl]-6,6-difluoro-5,7,7-trimethyl-2,5,6,7-tetrahydro-[1,4]oxazepin-3-ylamine, (R)-5-[5-(5-Chloro-pyridin-3-yl)-2,4-difluoro-phenyl]-6,6-difluoro-5,7,7-trimethyl-2,5,6,7-tetrahydro-[1,4]oxazepin-3-ylamine, (R)-5-[5-(5-Chloro-pyridin-3-yl)-2-fluoro-phenyl]-6,6-difluoro-5,7,7-trimethyl-2,5,6,7-tetrahydro-[1,4]oxazepin-3-ylamine, (R)-5-[5-(5-Chloro-pyrimidin-2-yl)-2,4-difluoro-phenyl]-6,6-difluoro-5,7,7-trimethyl-2,5,6,7-tetrahydro-[1,4]oxazepin-3-ylamine, (R)-5-[5-(6-Chloro-benzooxazol-2-yl)-2,4-difluoro-phenyl]-6,6-difluoro-5,7,7-trimethyl-2,5,6,7-tetrahydro-[1,4] oxazepin-3-ylamine, (R)-5-[5-(6-Chloro-benzooxazol-2-yl)-2-fluoro-phenyl]-6,6-difluoro-5,7,7-trimethyl-2,5,6,7-tetrahydro-[1,4]oxazepin-3-ylamine, (R)-5-[5-(6-Chloro-benzothiazol-2-yl)-2-fluoro-phenyl]-6,6-difluoro-5,7,7-trimethyl-2,5,6,7-tetrahydro-[1,4]oxazepin-3-ylamine, (R)-5-{2,4-Difluoro-5-[1-(4-fluoro-phenyl)-1H-pyrazol-4-yl]-phenyl}-6,6-difluoro-5,7,7-trimethyl-2,5,6,7-tetrahydro-[1,4]oxazepin-3-ylamine, (R)-5-{5-[1-(3-Chloro-phenyl)-1H-pyrazol-4-yl]-2-fluoro-phenyl}-6,6-difluoro-5,7,7-trimethyl-2,5,6,7-tetrahydro-[1,4]oxazepin-3-ylamine, (R)-6,6-Difluoro-5-(2-fluoro-5-pyrimidin-5-yl-phenyl)-5,7,7-trimethyl-2,5,6,7-tetrahydro-[1,4]oxazepin-3-ylamine, (R)-6,6-Difluoro-5,7,7-trimethyl-5-(4,3',5'-trifluoro-biphenyl-3-yl)-2,5,6,7-tetrahydro-[1,4]oxazepin-3-ylamine, (R)-6,6-Difluoro-5-[2-fluoro-5-(1-pyridin-2-yl-1H-imidazol-4-yl)-phenyl]-5,7,7-trimethyl-2,5,6,7-tetrahydro-[1,4] oxazepin-3-ylamine, (R)-6,6-Difluoro-5-[2-fluoro-5-(2-methyl-2H-pyrazol-3-yl)-phenyl]-5,7,7-trimethyl-2,5,6,7-tetrahydro-[1,4]oxazepin-3-ylamine, (R)-6,6-Difluoro-5-[2-fluoro-5-(2-methyl-thiazol-4-ylethynyl)-phenyl]-5,7,7-trimethyl-2,5,6,7-tetrahydro-[1,4]oxazepin-3-ylamine, (R)-6,6-Difluoro-5-[2-fluoro-5-(tetrahydro-pyran-4-yl)-phenyl]-5,7,7-trimethyl-2,5,6,7-tetrahydro-[1,4]oxazepin-3-ylamine, (R)-6,6-Difluoro-5-{2-fluoro-5-[1-(4-fluoro-phenyl)-1H-pyrazol-4-yl]-phenyl}-5,7,7-trimethyl-2,5,6,7-tetrahydro-[1,4]oxazepin-3-ylamine, (R)-6,6-Difluoro-5-{2-fluoro-5-[1-(5-trifluoromethyl-pyridin-2-yl)-1H-imidazol-4-yl]-phenyl}-5,7,7-trimethyl-2,5,6,7-tetrahydro-[1,4]oxazepin-3-ylamine, 3'-((R)-3-Amino-6,6-difluoro-5,7,7-trimethyl-2,5,6,7-tetrahydro-[1,4]oxazepin-5-yl)-4'-fluoro-biphenyl-3-sulfonic acid tert-butylamide, 3'-((R)-3-Amino-6,6-difluoro-5,7,7-trimethyl-2,5,6,7-tetrahydro-[1,4]oxazepin-5-yl)-4'-fluoro-biphenyl-3-sulfonic acid 2,2-dimethyl-propyl ester, 3'-((R)-3-Amino-6,6-difluoro-5,7,7-trimethyl-2,5,6,7-tetrahydro-[1,4]oxazepin-5-yl)-6,4'-difluoro-biphenyl-3-carbonitrile, 3'-((R)-3-Amino-6,6-difluoro-5,7,7-trimethyl-2,5,6,7-tetrahydro-[1,4]oxazepin-5-yl)-4'-fluoro-biphenyl-3-carbonitrile, 3'-((R)-3-Amino-6,6-difluoro-5,7,7-trimethyl-2,5,6,7-tetrahydro-[1,4]oxazepin-5-yl)-4'-fluoro-biphenyl-4-carbonitrile, 5'-((R)-3-Amino-6,6-difluoro-5,7,7-trimethyl-2,5,6,7-tetrahydro-[1,4]oxazepin-5-yl)-2',4'-difluoro-biphenyl-4-carbonitrile, 5'-((R)-3-Amino-6,6-difluoro-5,7,7-trimethyl-2,5,6,7-tetrahydro-[1,4]oxazepin-5-yl)-2',4'-difluoro-biphenyl-3-carbonitrile, and 5-[3-((R)-3-Amino-6,6-difluoro-5,7,7-trimethyl-2,5,6,7-tetrahydro-[1,4]oxazepin-5-yl)-4-fluoro-phenyl]-pyridine-3-sulfonic acid tert-butylamide, or pharmaceutically acceptable salts thereof.

A certain embodiment of the invention provides a compound as defined herein, selected from the group consisting of (R)-6,6-Difluoro-5-(2-fluoro-5-pyrimidin-5-yl-phenyl)-5-methyl-2,5,6,7-tetrahydro-[1,4]oxazepin-3-ylamine formate, (R)-5-(2,4-Difluoro-5-pyrimidin-5-yl-phenyl)-6,6-difluoro-5,7,7-trimethyl-2,5,6,7-tetrahydro-[1,4]oxazepin-3-ylamine, (R)-5-[5-(5-Chloro-pyridin-3-yl)-2,4-difluoro-phenyl]-6,6-difluoro-5,7,7-trimethyl-2,5,6,7-tetrahydro-[1,4]oxazepin-3-ylamine, (R)-6,6-Difluoro-5-(2-fluoro-5-pyrimidin-5-yl-phenyl)-5,7,7-trimethyl-2,5,6,7-tetrahydro-[1,4]oxazepin-3-ylamine, and 3'-((R)-3-Amino-6,6-difluoro-5,7,7-trimethyl-2,5,6,7-tetrahydro-[1,4]oxazepin-5-yl)-6,4'-difluoro-biphenyl-3-carbonitrile.

A certain embodiment of the invention provides a compound as defined herein, which is (R)-6,6-Difluoro-5-(2-fluoro-5-pyrimidin-5-yl-phenyl)-5-methyl-2,5,6,7-tetrahydro-[1,4]oxazepin-3-ylamine formate.

A certain embodiment of the invention provides a compound as defined herein, which is (R)-5-(2,4-Difluoro-5-pyrimidin-5-yl-phenyl)-6,6-difluoro-5,7,7-trimethyl-2,5,6,7-tetrahydro-[1,4]oxazepin-3-ylamine.

A certain embodiment of the invention provides a compound as defined herein, which is (R)-5-[5-(5-Chloro-pyridin-3-yl)-2,4-difluoro-phenyl]-6,6-difluoro-5,7,7-trimethyl-2,5,6,7-tetrahydro-[1,4]oxazepin-3-ylamine A certain embodiment of the invention provides a compound as defined herein, which is
(R)-6,6-Difluoro-5-(2-fluoro-5-pyrimidin-5-yl-phenyl)-5,7,7-trimethyl-2,5,6,7-tetrahydro-[1,4]oxazepin-3-ylamine.

A certain embodiment of the invention provides a compound as defined herein, which is 3'-((R)-3-Amino-6,6-difluoro-5,7,7-trimethyl-2,5,6,7-tetrahydro-[1,4]oxazepin-5-yl)-6,4'-difluoro-biphenyl-3-carbonitrile.

A certain embodiment of the invention provides a process to synthesize a compound of formula I as described herein, which process comprises reacting a compound of formula A10 to a compound of formula I

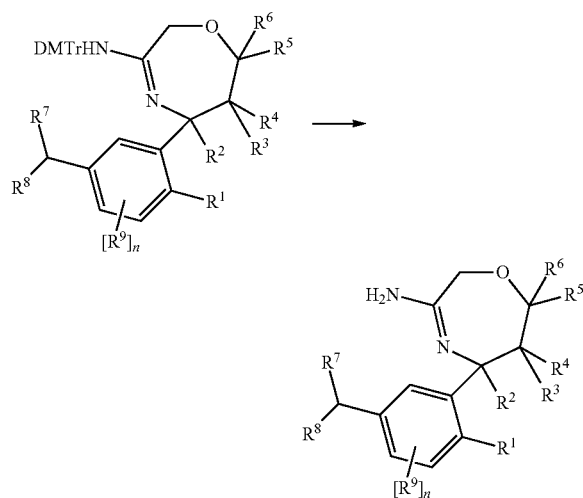

wherein $R^1$, $R^2$, $R^3$, $R^4$, $R^5$, $R^6$, $R^7$, $R^8$, $R^9$ and n are as defined herein.

A certain embodiment of the invention provides a compound of formula I as described herein, whenever prepared by a process as defined above.

A certain embodiment of the invention provides a compound of formula I as described herein for use as therapeutically active substance.

A certain embodiment of the invention provides a compound of formula I as described herein for the use as inhibitor of BACE1 and/or BACE2 activity.

A certain embodiment of the invention provides a compound of formula I as described herein for the use as inhibitor of BACE1 activity.

A certain embodiment of the invention provides a compound of formula I as described herein for the use as inhibitor of BACE2 activity.

A certain embodiment of the invention provides a compound of formula I as described herein for the use as inhibitor of BACE1 and BACE2 activity.

A certain embodiment of the invention provides a compound of formula I as described herein for the use as therapeutically active substance for the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides a compound of formula I as described herein for the use as therapeutically active substance for the therapeutic and/or prophylactic treatment of Alzheimer's disease.

A certain embodiment of the invention provides a compound of formula I as described herein for the use as therapeutically active substance for the therapeutic and/or prophylactic treatment of diabetes or type 2 diabetes.

A certain embodiment of the invention provides a compound of formula I as described herein for the use as therapeutically active substance for the therapeutic and/or prophylactic treatment of diabetes.

A certain embodiment of the invention provides a compound of formula I as described herein for the use as therapeutically active substance for the therapeutic and/or prophylactic treatment of Alzheimer's disease, diabetes or type 2 diabetes.

A certain embodiment of the invention provides a compound of formula I as described herein for the use as therapeutically active substance for the therapeutic and/or prophylactic treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease.

A certain embodiment of the invention provides a pharmaceutical composition comprising a compound of formula I as described herein and a pharmaceutically acceptable carrier and/or a pharmaceutically acceptable auxiliary substance.

A certain embodiment of the invention provides the use of a compound of formula I as described herein for the manufacture of a medicament for the use in inhibition of BACE1 and/or BACE2 activity.

A certain embodiment of the invention provides the use of a compound of formula I as described herein for the manufacture of a medicament for the use in inhibition of BACE1 activity.

A certain embodiment of the invention provides the use of a compound of formula I as described herein for the manufacture of a medicament for the use in inhibition of BACE2 activity.

A certain embodiment of the invention provides the use of a compound of formula I as described herein for the manufacture of a medicament for the use in inhibition of BACE1 and BACE2 activity.

A certain embodiment of the invention provides the use of a compound of formula I as described herein for the manufacture of a medicament for the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides the use of a compound of formula I as described herein for the manufacture of a medicament for the therapeutic and/or prophylactic treatment of Alzheimer's disease.

A certain embodiment of the invention provides the use of a compound of formula I as described herein for the manufacture of a medicament for the therapeutic and/or prophylactic treatment of diabetes or type 2 diabetes.

A certain embodiment of the invention provides the use of a compound of formula I as described herein for the manufacture of a medicament for the therapeutic and/or prophylactic treatment of diabetes.

A certain embodiment of the invention provides the use of a compound of formula I as described herein for the manufacture of a medicament for the therapeutic and/or prophylactic treatment of Alzheimer's disease, diabetes or type 2 diabetes.

A certain embodiment of the invention provides the use of a compound of formula I as described herein for the manufacture of a medicament for the therapeutic and/or prophylactic treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease.

A certain embodiment of the invention provides a compound of formula I as described herein for the use in inhibition of BACE1 and/or BACE2 activity.

A certain embodiment of the invention provides a compound of formula I as described herein for the use in inhibition of BACE1 activity.

A certain embodiment of the invention provides a compound of formula I as described herein for the use in inhibition of BACE2 activity.

A certain embodiment of the invention provides a compound of formula I as described herein for the use in inhibition of BACE1 and BACE2 activity.

A certain embodiment of the invention provides a compound of formula I as described herein for the use in the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides a compound of formula I as described herein for the use in the therapeutic and/or prophylactic treatment of Alzheimer's disease.

A certain embodiment of the invention provides a compound of formula I as described herein for the use in the therapeutic and/or prophylactic treatment of diabetes or type 2 diabetes.

A certain embodiment of the invention provides provides a compound of formula I as described herein for the use in the therapeutic and/or prophylactic treatment of diabetes.

A certain embodiment of the invention provides a compound of formula I as described herein for the use in the therapeutic and/or prophylactic treatment of Alzheimer's disease, diabetes or type 2 diabetes.

A certain embodiment of the invention provides a method for the use in inhibition of BACE1 and/or BACE2 activity or for the therapeutic and/or prophylactic treatment of diseases and disorders characterized by elevated β-amyloid levels and/or β-amyloid oligomers and/or β-amyloid plaques and further deposits, Alzheimer's disease, diabetes or type 2 diabetes, which method comprises administering compound of formula I as described herein to a human being or animal.

A certain embodiment of the invention provides a method for the use in the therapeutic and/or prophylactic treatment of Alzheimer's disease, diabetes or type 2 diabetes, which method comprises administering a compound of formula I as described herein to a human being or animal.

A certain embodiment of the invention provides a method for the use in the therapeutic and/or prophylactic treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease, which method comprises administering a compound of formula I as described herein to a human being or animal.

Furthermore, the invention includes all optical isomers, i.e. diastereoisomers, diastereomeric mixtures, racemic mixtures, all their corresponding enantiomers and/or tautomers as well as their solvates of the compounds of formula I.

The skilled person in the art will recognize that the compounds of formula I can exist in tautomeric forms, e.g. in the following tautomeric form:

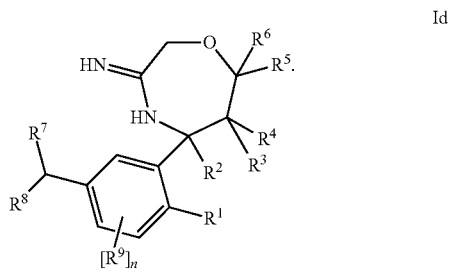

Id

All tautomeric forms are encompassed in the present invention.

The compounds of formula I can contain one or more asymmetric centers and can therefore occur as racemates, racemic mixtures, single enantiomers, diastereomeric mixtures and individual diastereomers. Additional asymmetric centers can be present depending upon the nature of the various substituents on the molecule. Each such asymmetric center will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations can be achieved as known in the art by appropriate modification of the methodology disclosed herein. Their absolute stereochemistry can be determined by the x-ray crystallography of crystalline products or crystalline intermediates which are derivatized, if necessary, with a reagent containing an asymmetric center of known absolute configuration. If desired, racemic mixtures of the compounds can be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. Particular examples of isomers of a compound of formula I are a compound of formula Ia or a compound of formula Ib, in particular Ia, wherein the residues have the meaning as described in any of the embodiments.

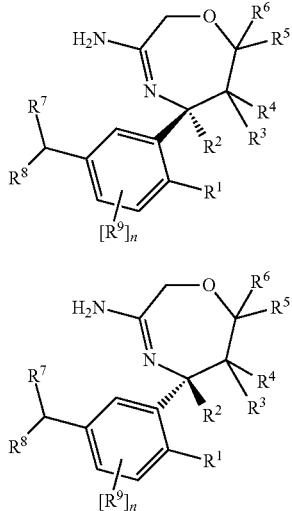

Ia

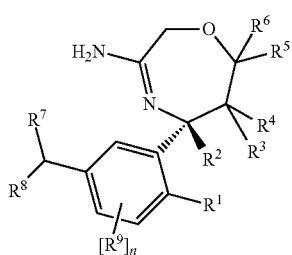

Ib

In the embodiments, where optically pure enantiomers are provided, optically pure enantiomer means that the compound contains >90% of the desired isomer by weight, particularly >95% of the desired isomer by weight, or more particularly >99% of the desired isomer by weight, said weight percent based upon the total weight of the isomer(s) of the compound. Chirally pure or chirally enriched compounds can be prepared by chirally selective synthesis or by separation of enantiomers. The separation of enantiomers can be carried out on the final product or alternatively on a suitable intermediate.

The compounds of formula I can be prepared in accordance with the following schemes. The starting material is commercially available or can be prepared in accordance with known methods. Any previously defined residues and variables will continue to have the previously defined meaning unless otherwise indicated.

The compounds of formula I can be prepared through a number of synthetic routes for example as illustrated in below schemes. The preparation of compounds of formula I of the present invention can be carried out in sequential or convergent synthetic routes. Syntheses of the compounds of the invention are shown in the following schemes. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in schemes described below, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

In more detail, compounds of formula I according to the present invention can be prepared by the methods and procedures given below. Some typical procedures for the preparation of compounds of formula I are illustrated in Schemes A-D.

Sulfinyl imines of formula A2 can be prepared in analogy to T. P. Tang & J. A. Ellman, J. Org. Chem. 1999, 64, 12, by condensation of an aryl ketone and a sulfinamide, e.g. an alkyl sulfinamide, most particularly (R)-(+)-tert-butylsulfinamide in the presence of a Lewis acid such as e.g. a titanium(IV) alkoxide, more particularly titanium(IV)ethoxide in a solvent such as an ether, e.g. diethyl ether or more particularly tetrahydrofuran.

The conversion of the sulfinyl imine A2 to the sulfinamide ester A3 proceeds stereoselectively by the chiral directing group as described by Tang & Ellman. The sulfinyl imine A2 can be reacted with a titanium enolate generated from e.g. an alkyl acetate, particularly ethyl acetate, LDA and chlorotriisopropoxytitanium at low temperature, particularly at −78° C. in a solvent such as an ether, e.g. diethyl ether or more particularly tetrahydrofuran. Alternatively sulfinamide ester A3 can be produced from sulfinyl imine A2 by Reformatsky reaction of a bromoacetic ester derivative and zinc dust, optionally in the presence of copper(I) chloride, in a solvent such as an ether, e.g. diethyl ether or more particularly tetrahydrofuran, at temperatures from 0 to 70° C., particularly at 23° C.

Sulfinamide ester A3 can be reduced to the alcohol A4 by the reduction of the ethylester with an alkali hydride, particularly lithium borohydride or lithium aluminium hydride in a solvent such as an ether, e.g. diethyl ether or more particularly tetrahydrofuran.

Alkylation of the alcohol A4 to the nitrile A5 can be accomplished with a suitable mild base particularly silver(I) oxide in a solvent such as tetrahydrofuran or dichloromethane, more a xyleneably dichloromethane in the presence of an alkylating catalyst such as tetra butyl ammonium iodide.

Hydrolysis of the chiral directing group in the nitrile A5 to give the amino nitrile A6 can be accomplished with a mineral acid, e.g. sulfuric acid or in particular hydrochloric acid in a solvent such as an ether, e.g. diethyl ether or more particular 1,4-dioxane.

Aminooxazepine A7 can be prepared by the reaction of amino nitrile A6 and trimethyl aluminium in a solvent such as a xylene, particularly toluene.

Palladium-catalyzed cross coupling between organoboronic acids or esters thereof and aminooxazepine A7 under conditions (Suzuki-Miyaura-coupling) known to those skilled in the art yields the final compound of formula I.

The protection of the aminooxazepine A7 to give A8 can be accomplished with a triphenylmethyl protecting group, a xyleneeably 4,4'-dimethoxytrityl and a base, e.g. an alkyl amine, a xyleneably triethyl amine in an inert solvent such as dichloromethane.

Palladium-catalyzed cross coupling between organoboronic acids or esters thereof and the aminooxazepine A8 under conditions (Suzuki-Miyaura-coupling) known to those skilled in the art yields A10.

Deprotection of the dimethoxytrityl protected amine A10 to the target amine of formula I can be accomplished involving a strong carbonic acid, e.g. trifluoroacetic acid, in a halogenated solvent, e.g. dichloromethane, at temperatures between 0° C. and 23° C.

Alternatively, the conversion of A8 to the N-protected aminooxazepine of formula A10 can be accomplished via the boronic acid derivative of formula A9. Boronic acid derivatives A9 can be obtained by reaction of an aryl halogenide of formula A8 with alkyl borates or tetraalkoxydiboranes, a xyleneably with bis(pinacolato)diborane or 5,5,5',5'-tetramethyl-[2,2']bi[[1,3,2]dioxaborinanyl], in presence of a metal catalyst like e.g. bis(triphenylphosphino)palladium(II) dichloride or [1,1'-bis(diphenylphosphino) ferrocen]-palladium(II) dichloride, and a base like e.g. potassium acetate in an inert solvent like dioxane at temperatures between room temperature and 130° C.

Further palladium-catalyzed cross coupling between organoboronic esters of formula A9 and derivatives of formula $(R^7R^8)C$—Y, wherein Y has the meaning of a leaving group, under conditions (Suzuki-Miyaura-coupling) known to those skilled in the art yields compounds of formula A10.

Scheme A: Synthesis of compounds of formula I-1
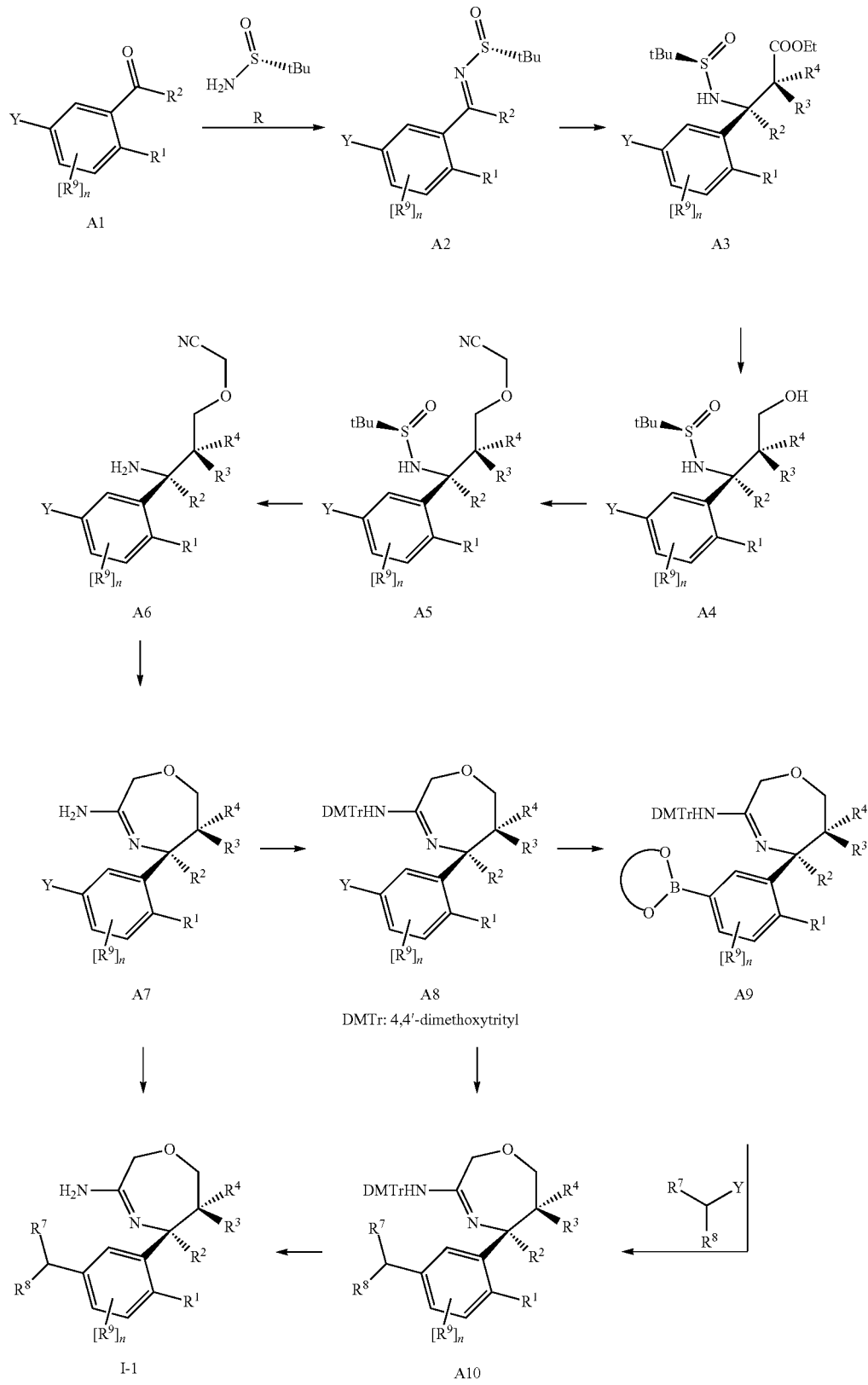
Y = leaving group, in particular Br Sulfinamide ester A3 can be transformed into alcohol B1 by the reaction of the ethylester with an excess of a Grignard or an organolithium reagent, e.g. methyl- or ethylmagnesium halide, methyllithium etc., in a solvent such as an ether, e.g. diethyl ether or more a xyleneably tetrahydrofuran, at temperatures between −78 and 70° C., a xyleneably at 0 to 23° C.

Scheme B: Synthesis of compounds of formula I.

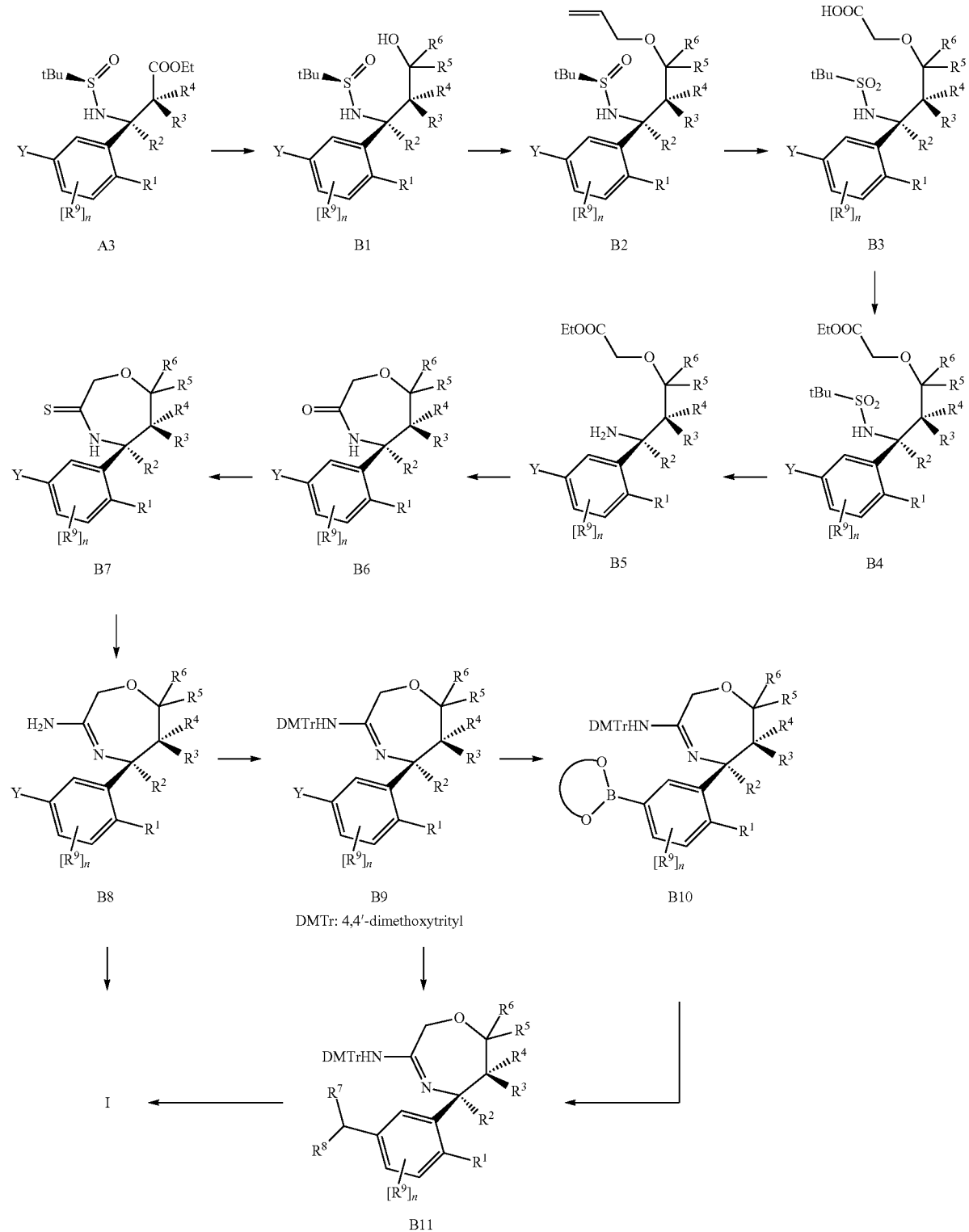

DMTr: 4,4′-dimethoxytrityl

Y = leaving group, in particular Br

Compounds of formula B2 can be prepared by selective O-allylation by reacting the alcohol of the formula B1 with allyl tert-butyl carbonate [CAS no. 70122-89-3] in the presence of catalytic amounts of a palladium(II) salt, like e.g. palladium(II) acetate, and a phosphine ligand, like e.g. triphenylphosphine, or with a palladium(0) catalyst, like e.g. tetrakistriphenylphosphinepalladium(0), in a solvent such as e.g. tetrahydrofuran or dioxane at temperatures between 23 and 100° C., a xyleneably at 50 to 80° C. as described by Haight, A. R.; Stoner, E. J.; Peterson, M. J.; Grover, V. K.; in *J. Org. Chem.* 2003, 68 (21), 8092 (DOI: 10.1021/jo0301907). The acids of formula B3 can be prepared by oxidation of the O-allyl ethers of formula B2 by reacting it with a periodate salt, such as sodium or potassium periodate, in the presence of a catalytic amount of a ruthenium salt, such as e.g. ruthenium(III) chloride, in a solvent mixture consisting of ethyl acetate or tetrachloromethane, acetonitrile and water at temperatures between 0 and 40° C., a xyleneably 20 to 30° C. These reaction conditions will cause concomitant oxidation of the tert-butylsulfinic acid amide into the corresponding tert-butylsulfonic acid amide. The acids of formula B3 can be converted into the ethyl esters of formula B4 by treatment with thionyl chloride in ethanol at temperatures between 23 and 80° C.

The amino esters of formula B5 can be prepared by cleavage of the tert-butylsulfonic acid amide in compounds of formula B4 by treatment with a strong acid, a xyleneably trifluoromethanesulfonic acid, in a chlorinated solvent, such as e.g. dichloromethane, at temperatures between 0 and 30° C., a xyleneably at 23° C. This method has been described by Sun P., Weinreb S. M., Shang M. in *J. Org. Chem.* 1997, 62(24), 8604.

Cyclization of the amino esters of formula B5 to the lactams of formula B6 can be achieved by the reaction with trimethyl aluminium in a solvent such as a xylene, particularly toluene, at temperatures between 0 and 100° C., in particular 23° C.

The lactam B6 can be converted into the thiolactam B7 by reaction with 2,4-bis-(4-methoxy-phenyl)-[1,3,2,4]dithiadipho sphetane 2,4-disulfide (Lawesson's reagent) or phosphorous pentasulfide in an ether solvent such as tetrahydrofuran, 1,2-dimethoxyethane or 1,4-dioxane, particularly 1,4-dioxane, at temperatures between 23 and 100° C., particularly between 50 and 80° C.

Aminooxazepines of formula B8 can be prepared from the thiolactams B7 by reaction with a solution of ammonia in a protic solvent such as methanol, ethanol or water, particularly methanol, with or without presence of a mild oxidant such as tert-butylhydroperoxide at temperatures between 0 and 60° C., particularly at 23° C. in the presence of an oxidant or at 50 to 60° C. in the absence of an oxidant.

Palladium-catalyzed cross coupling between organoboronic acids or esters thereof and the aminooxazepine B8 under conditions (Suzuki-Miyaura-coupling) known to those skilled in the art yields the target compounds of formula I.

Alternatively, compounds of formula B8 can be used in their protected form. The protection of aminooxazepines of formula B8 to give B9 can be accomplished with a triphenylmethyl protecting group, particularly 4,4'-dimethoxytrityl and a base, e.g. an alkyl amine, particularly triethyl amine in an inert solvent such as dichloromethane.

Palladium-catalyzed cross coupling between organoboronic acids or esters thereof and the aminooxazepine B9 under conditions (Suzuki-Miyaura-coupling) known to those skilled in the art yields compounds of formula B11.

Deprotection of the dimethoxytrityl protected amine B11 to the target amine of formula I can be accomplished involving a strong carbonic acid, e.g. trifluoroacetic acid, in a halogenated solvent, e.g. dichloromethane, at temperatures between o and 23° C.

The conversion of B9 to the N-protected aminooxazepine of formula B11 can be accomplished via the boronic acid derivative of formula B10. Boronic acid derivatives B10 can be obtained by reaction of an aryl halogenide of formula B9 with alkyl borates or tetraalkoxydiboranes, in particularly with bis(pinacolato)diborane or 5,5,5',5'-tetramethyl-[2,2]bi[[1,3,2]dioxaborinanyl], in presence of a metal catalyst like e.g. bis(triphenylphosphino)palladium(II) dichloride or [1,1'-bis(diphenylphosphino)ferrocen]-palladium(II) dichloride, and a base like e.g. potassium acetate in an inert solvent like dioxane at temperatures between room temperature and 130° C.

Further palladium-catalyzed cross coupling between organoboronic esters of formula B10 and derivatives of formula $(R^7R^8)C$—Y, wherein Y has the meaning of a leaving group, under conditions (Suzuki-Miyaura-coupling) known to those skilled in the art yields compounds of formula B11.

Deprotection of the dimethoxytrityl protected amine B11 to the target amine of formula I can be accomplished involving a strong carbonic acid, e.g. trifluoroacetic acid, in a halogenated solvent, e.g. dichloromethane, at temperatures between o and 23° C.

Compounds of formula I, wherein $R^3$ and $R^4$ together with the carbon atom to which they are attached form an alkyne, can be prepared as depicted in Scheme C. The Sonogashira coupling of terminal alkynes with aryl bromides of formula B6', iodides of formula B6" or of formula B8' is performed with a palladium catalyst, e.g. bis(triphenyphosphine) palladium(II)chloride, a copper(I) co-catalyst, e.g. copper(I)iodide, and an amine base, e.g. triethylamine, conditions known to those skilled in the art. In some cases the use of iodides is a xylenered over the use of bromides. The conversion of arylbromides of formula B6' into the corresponding iodides of formula B6" can be accomplished utilizing a catalyst system comprising copper(I)iodide and a 1,2- or 1,3-diamine ligand as described by A. Klapars and S. L. Buchwald in JACS 2002, 124(50), 14844.

Scheme C: Syntheses of compounds of formula I; particularly of derivatives where $R^7$ and $R^8$ together with the C to which they are attached form an alkyne.

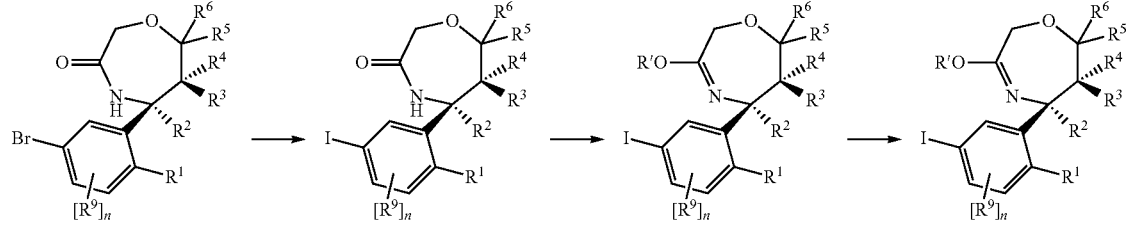

R' = lower alkyl

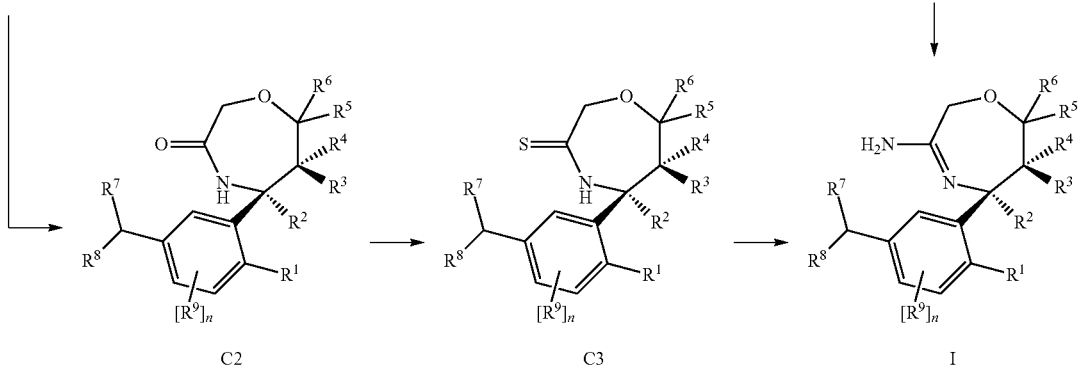

The further transformations leading to the target compound of formula I can be accomplished via the thiolactams of formula C3 as already described before.

The iminoether of formula C1 can be synthesized by treatment of the lactam of formula B6" with alkyl oxonium salts, e.g. trimethyloxonium tetrafluoroborate or triethyloxonium tetrafluoroborate.

Treatment of the iminoether of formula C1 with ammonium salts, such as ammonium chloride, in polar solvents like alcohols, e.g. methanol, yields the intermediate amine of formula B8.

Scheme D: Alternative synthesis of lactame intermediate C2.

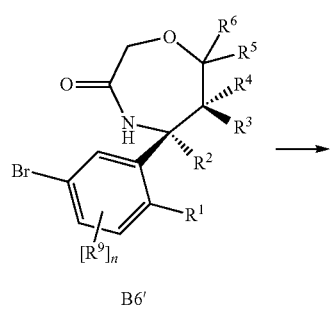

B6'

-continued

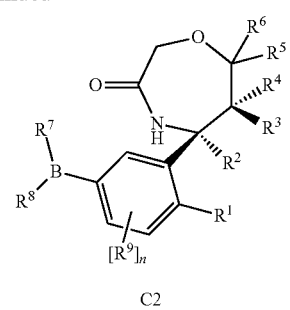

C2

An alternative synthesis of lactame intermediate C2 is depicted in Scheme D. The conversion of B6' to the lactame C2 can be accomplished via the boronic acid derivative of formula D1. Boronic acid derivatives D1 can be obtained by reaction of an aryl halogenide of formula B6' with alkyl borates or tetraalkoxydiboranes, particularly with bis(pinacolato)diborane or 5,5,5',5'-tetramethyl-[2,2']bi[[1,3,2]dioxaborinanyl], in presence of a metal catalyst like e.g. bis(triphenylphosphino)palladium(II) dichloride or [1,1'-bis(diphenylphosphino)ferrocen]-palladium(II) dichloride, and a base like e.g. potassium acetate in an inert solvent like dioxane at temperatures between room temperature and 130° C.

Further palladium-catalyzed cross coupling between organoboronic esters of formula D1 and derivatives of formula $(R^7R^8)C$—Y, wherein Y has the meaning of a leaving group, under conditions (Suzuki-Miyaura-coupling) known to those skilled in the art yields compounds of formula C2.

Scheme E: Alternative synthesis of lactame intermediate B6.

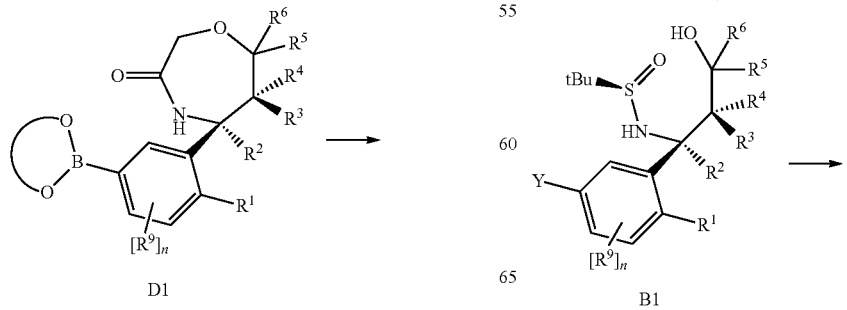

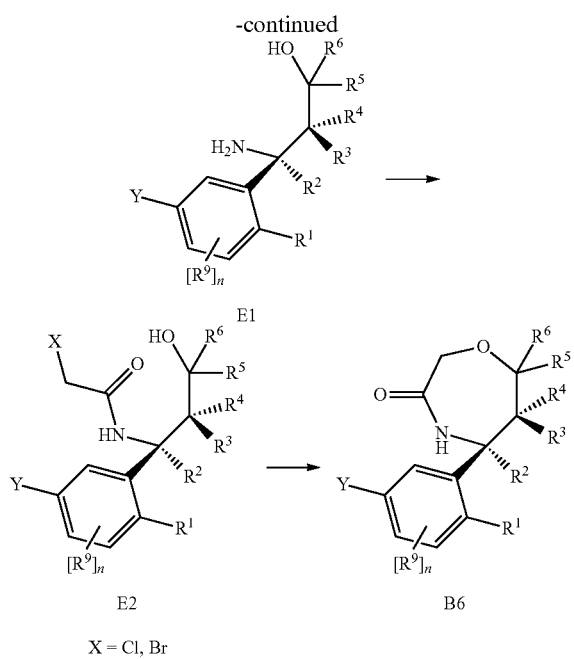

X = Cl, Br
Y = leaving group, in particular Br

An alternative synthesis of the lactame intermediate B6 is depicted in Scheme E. Hydrolysis of the chiral directing group in the alcohol B1 to give the amino alcohol E1 can be accomplished with a mineral acid, e.g. sulfuric acid or particularly hydrochloric acid in a solvent such as an ether, e.g. diethyl ether or tetrahydrofuran, more particularly 1,4-dioxane, at temperatures from 0 to 23° C.

Haloacetamide E2, where X is chlorine or bromine, can be prepared by selective acylation of the amino group in amino alcohol E1 with an acid chloride, such as chloro- or bromoacetyl chloride, under biphasic conditions with a suitable mild base, like e.g. saturated aqueous solutions of sodium or potassium hydrogencarbonate, in a solvent such as toluene, ethyl acetate or dichloromethane, more particularly dichloromethane at temperatures between 0 and 23° C.

Cyclization of the haloacetamide E2 to the lactam B6 can be accomplished by reacting it with a strong base, such as potassium tert-butoxide or potassium tert-amylate, in a solvent such as tert-butanol or tert-amylalcohol, toluene or tetrahydrofuran, particularly toluene, at temperatures between 0 and 70° C., particularly at 23° C.

The corresponding pharmaceutically acceptable salts with acids can be obtained by standard methods known to the person skilled in the art, e.g. by dissolving the compound of formula I in a suitable solvent such as e.g. dioxane or tetrahydrofuran and adding an appropriate amount of the corresponding acid. The products can usually be isolated by filtration or by chromatography. The conversion of a compound of formula I into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation. Particular salts are hydrochloride, formate and trifluoroacetate.

Insofar as their preparation is not described in the examples, the compounds of formula I as well as all intermediate products can be prepared according to analogous methods or according to the methods set forth herein. Starting materials are commercially available, known in the art or can be prepared by methods known in the art or in analogy thereto.

It will be appreciated that the compounds of formula I in this invention can be derivatized at functional groups to provide derivatives which are capable of conversion back to the parent compound in vivo.

Pharmacological Tests

The compounds of formula I and their pharmaceutically acceptable salts possess valuable pharmacological properties. Compounds of the present invention are associated with inhibition of BACE1 and/or BACE2 activity. The compounds were investigated in accordance with the test given hereinafter.

Cellular Aβ-Lowering Assay:

a) Human HEK293 cells which are stably transfected with a vector expressing a cDNA of the human APP wt gene (APP695) were used to assess the potency of the compounds in a cellular assay. The cells were seeded in 96-well microtiter plates in cell culture medium (Iscove, plus 10% (v/v) fetal bovine serum, glutamine, penicillin/streptomycin) to about 80% confluence and the compounds were added at a 10× concentration in 1/10 volume of medium without FCS containing 8% DMSO (final concentration of DMSO was kept at 0.8% v/v). After 18-20 hrs incubation at 37° C. and 5% $CO_2$ in a humidified incubator the culture supernatant was harvested for the determination of Aβ40 concentrations. 96 well ELISA plates (e.g., Nunc MaxiSorb) were coated with monoclonal antibody which specifically recognize the C-terminal end of Aβ40 (Brockhaus et al., NeuroReport 9, 1481-1486; 1998). After blocking of non-specific binding sites with e.g. 1% BSA and washing, the culture supernatants were added in suitable dilutions together with a horseradish peroxidase-coupled Aβ detection antibody (e.g., antibody 4G8, Senetek, Maryland Heights, Mo.) and incubated for 5 to 7 hrs. Subsequently the wells of the microtiter plate were washed extensively with Tris-buffered saline containing 0.05% Tween 20 and the assay was developed with tetramethylbenzidine/ $H_2O_2$ in citric acid buffer. After stopping the reaction with one volume 1 N $H_2SO_4$ the reaction was measured in an ELISA reader at 450 nm wavelength. The concentrations of Aβ in the culture supernatants were calculated from a standard curve obtained with known amounts of pure Aβ peptide.

b) HEK293 APP: Abeta 40 AlphaLISA Assay

The cells were seeded in 96 well Microtiter plates in cell culture medium (Iscove's, plus 10% (v/v) fetal bovine serum, penicillin/streptomycin) to about 80% confluency and the compounds were added at a 3× concentration in 1/3 volume of culture medium (final DMSO concentration was kept at 1% v/v). After 18-20 hrs incubation at 37° C. and 5% $CO_2$ in a humidified incubator, the culture supernatants were harvested for the determination of Aβ 40 concentrations using Perkin-Elmer Human Amyloid beta 1-40 (high specificity) Kit (Cat#AL275C).

In a Perkin-Elmer White Optiplate-384 (Cat#6007290), 2·1 culture supernatants were combined with 2 μl of a 10X AlphaLISA Anti-hAβ Acceptor beads+Biotinylated Antibody Anti-Aβ 1-40 Mix (50 μg/mL/5 nM). After 1 hour room temperature incubation, 16 μl of a 1.25× preparation of Streptavidin (SA) Donor beads (25 μg/mL) were added and incubated for 30 minutes in the Dark. Light Emission at 615 nm was then recorded using EnVision-Alpha Reader. Levels of Aβ 40 in the culture supernatants were calculated as percentage of maximum signal (cells treated with 1% DMSO without inhibitor). The IC50 values were calculated using the Excel XLfit software.

Assay for BACE Inhibition by Measuring Cellular TMEM27 Cleavage:

The assay uses the principle of inhibition of human TMEM27 cleavage by endogenous cellular BACE2 in the Ins1e rat cell line and shedding from the cell surface into the culture medium, followed by detection in an ELISA assay Inhibition of BACE2 prevents the cleavage and shedding in a dose-dependent manner The stable cell line "INS-TMEM27" represents an INS1e-derived cell line with inducible expression (using the TetOn system) of full-length hTMEM27 in a doxycycline-dependent manner. The cells are cultured throughout the experiment in RPMI1640+Glutamax (Invitrogen) Penicillin/Streptomycin, 10% Fetal bovine serum, 100 mM pyruvate, 5 mM beta-mercatptoethanol, 100 micrograms/ml G418 and 100 microgram/ml hygromycin and are grown inadherent culture at 37° C. in a standard $CO_2$ cell culture incubator.

INS-TMEM27 cells are seeded in 96-well plates. After 2 days in culture, BACE2 inhibitor is added in a range of concentrations as required by the assay and after a further two hours, doxycycline is added to a final concentration of 500 ng/ml. The cells are incubated for a further 46 hours and the supernatant harvested for detection of shed TMEM27.

An ELISA assay (using a pair of mouse anti-human-TMEM27 antibodies, raised against the extracellular domain of TMEM27) is used for detection of TMEM27 in the culture medium. An $EC_{50}$ for BACE2 inhibition is calculated using the ELISA readout for each inhibitor concentration with standard curve-fitting software such as XLFit for the Excel spreadsheet program.

TABLE 1

| Ex. | Structure | BACE1 $IC_{50}$ [μM] | BACE2 $IC_{50}$ [μM] |
|---|---|---|---|
| 1 | 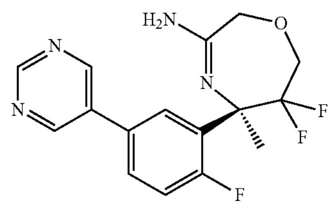 [SMILES: C[C@]1(c2cc(-c3cncnc3)ccc2F)N=C(N)COCC1(F)F] | $0.253^a$ | |
| 2 | 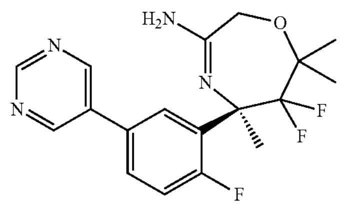 [SMILES: CC1(C)OCC(N)=N[C@](C)(c2cc(-c3cncnc3)ccc2F)C1(F)F] | $0.056^a$ | |
| 3 | 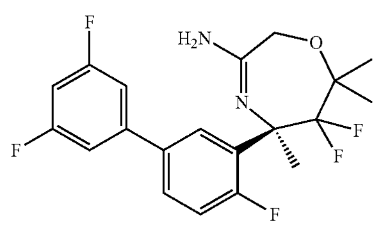 [SMILES: CC1(C)OCC(N)=N[C@](C)(c2cc(-c3cc(F)cc(F)c3)ccc2F)C1(F)F] | $0.180^a$ | |
| 4 | 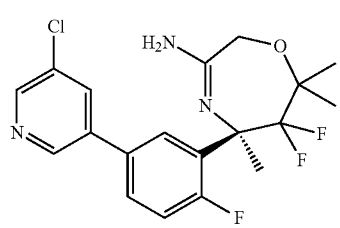 [SMILES: CC1(C)OCC(N)=N[C@](C)(c2cc(-c3cncc(Cl)c3)ccc2F)C1(F)F] | $0.205^a$ | 0.592 |
| 5 | 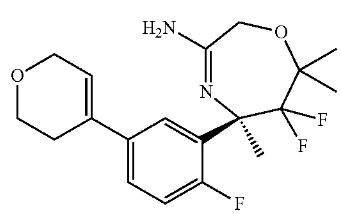 [SMILES: CC1(C)OCC(N)=N[C@](C)(c2cc(C3=CCOCC3)ccc2F)C1(F)F] | $0.430^a$ | |

TABLE 1-continued

| Ex. | Structure | BACE1 IC$_{50}$ [µM] | BACE2 IC$_{50}$ [µM] |
|---|---|---|---|
| 6 | 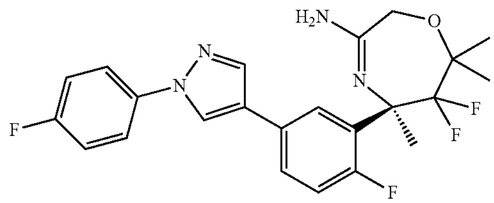 [SMILES: CC1(C)OCC(N)=N[C@](C)(c2cc(-c3cnn(-c4ccc(F)cc4)c3)ccc2F)C1(F)F] | 0.520$^a$ | |
| 7 | 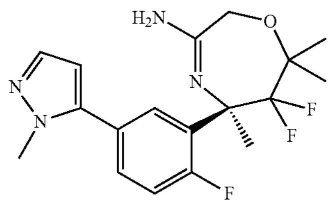 [SMILES: Cn1nccc1-c1ccc(F)c([C@@]2(C)N=C(N)COC(C)(C)C2(F)F)c1] | 0.540$^a$ | |
| 8 | 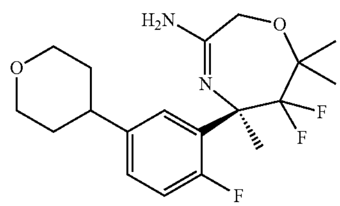 [SMILES: CC1(C)OCC(N)=N[C@](C)(c2cc(C3CCOCC3)ccc2F)C1(F)F] | 0.650$^a$ | |
| 9 | 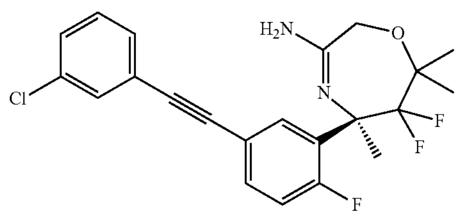 [SMILES: CC1(C)OCC(N)=N[C@](C)(c2cc(C#Cc3cccc(Cl)c3)ccc2F)C1(F)F] | 1.340$^a$ | |
| 10 | 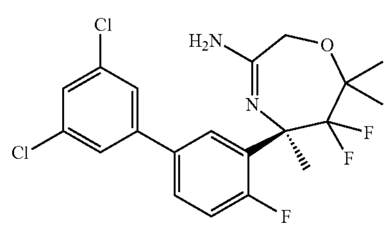 [SMILES: CC1(C)OCC(N)=N[C@](C)(c2cc(-c3cc(Cl)cc(Cl)c3)ccc2F)C1(F)F] | 1.595$^a$ | 1.333 |
| 11 | 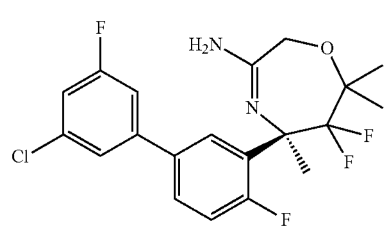 [SMILES: CC1(C)OCC(N)=N[C@](C)(c2cc(-c3cc(F)cc(Cl)c3)ccc2F)C1(F)F] | 0.510$^b$ | |
| 12 | 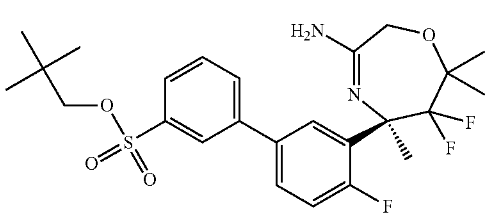 [SMILES: CC(C)(C)COS(=O)(=O)c1cccc(-c2ccc(F)c([C@@]3(C)N=C(N)COC(C)(C)C3(F)F)c2)c1] | 5.180$^b$ | |

TABLE 1-continued

| Ex. | Structure | BACE1 IC$_{50}$ [μM] | BACE2 IC$_{50}$ [μM] |
|---|---|---|---|
| 13 | 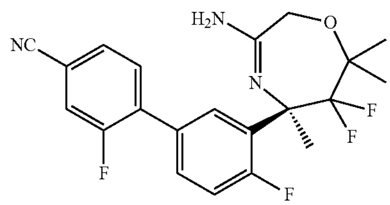 [SMILES: CC1(C)OCC(N)=N[C@](C)(c2cc(-c3ccc(C#N)cc3F)ccc2F)C1(F)F] | 0.092[a] | |
| 14 | 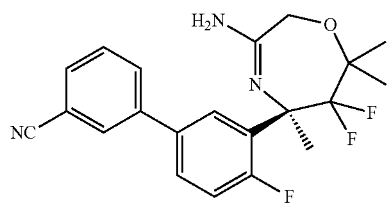 [SMILES: CC1(C)OCC(N)=N[C@](C)(c2cc(-c3cccc(C#N)c3)ccc2F)C1(F)F] | 0.186[a] | 0.279 |
| 15 | 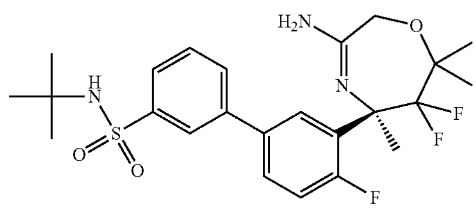 [SMILES: CC(C)(C)NS(=O)(=O)c1cccc(-c2ccc(F)c([C@@]3(C)N=C(N)COC(C)(C)C3(F)F)c2)c1] | 4.000[b] | |
| 16 | 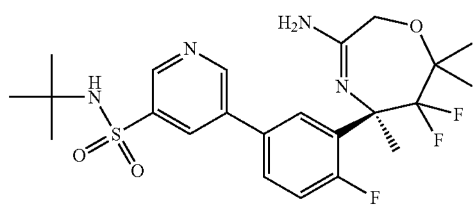 [SMILES: CC(C)(C)NS(=O)(=O)c1cncc(-c2ccc(F)c([C@@]3(C)N=C(N)COC(C)(C)C3(F)F)c2)c1] | 1.550[b] | |
| 17 | 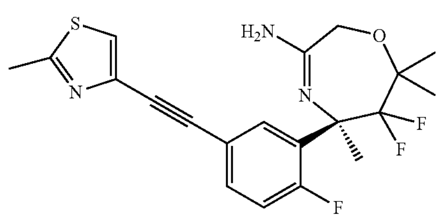 | 0.800[a] | |
| 18 | 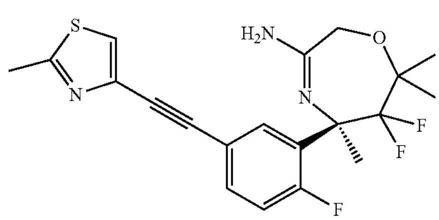 | 3.150[a] | |
| 19 | 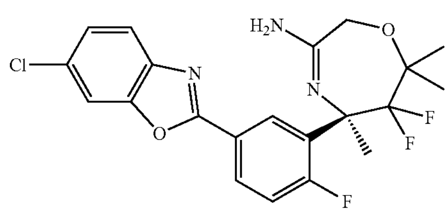 [SMILES: CC1(C)OCC(N)=N[C@](C)(c2cc(-c3nc4ccc(Cl)cc4o3)ccc2F)C1(F)F] | 0.250[a] | |

TABLE 1-continued

| Ex. | Structure | BACE1 IC$_{50}$ [μM] | BACE2 IC$_{50}$ [μM] |
|---|---|---|---|
| 20 | 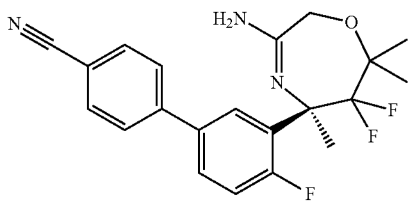 [SMILES: CC1(C)OCC(N)=N[C@](C)(c2cc(-c3ccc(C#N)cc3)ccc2F)C1(F)F] | 0.710[b] | |
| 21 | 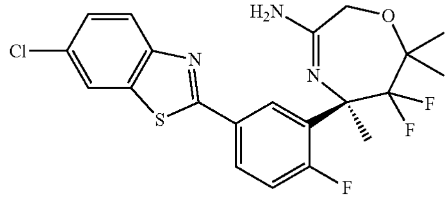 [SMILES: CC1(C)OCC(N)=N[C@](C)(c2cc(-c3nc4ccc(Cl)cc4s3)ccc2F)C1(F)F] | 7.430[b] | |
| 22 | 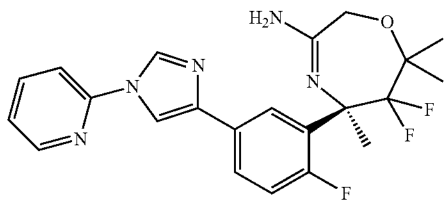 [SMILES: CC1(C)OCC(N)=N[C@](C)(c2cc(-c3cn(-c4ccccn4)cn3)ccc2F)C1(F)F] | 0.200[b] | |
| 23 | 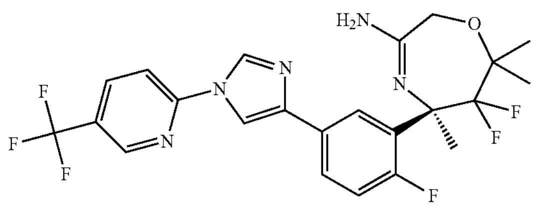 [SMILES: CC1(C)OCC(N)=N[C@](C)(c2cc(-c3cn(-c4ccc(C(F)(F)F)cn4)cn3)ccc2F)C1(F)F] | 0.220[b] | |
| 24 | 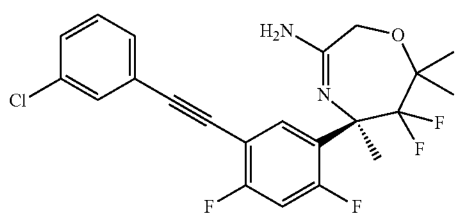 [SMILES: CC1(C)OCC(N)=N[C@](C)(c2cc(C#Cc3cccc(Cl)c3)c(F)cc2F)C1(F)F] | 1.270[b] | |
| 25 | 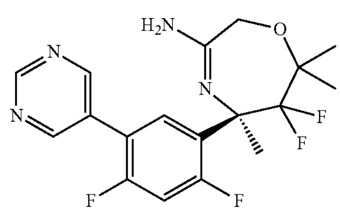 [SMILES: CC1(C)OCC(N)=N[C@](C)(c2cc(-c3cncnc3)c(F)cc2F)C1(F)F] | 0.007[a] | |
| 26 | 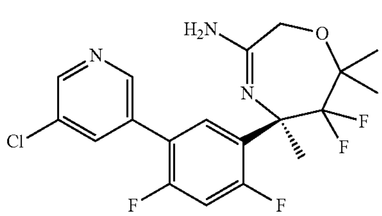 [SMILES: CC1(C)OCC(N)=N[C@](C)(c2cc(-c3cncc(Cl)c3)c(F)cc2F)C1(F)F] | 0.081[a] | |

TABLE 1-continued

| Ex. | Structure | BACE1 IC$_{50}$ [μM] | BACE2 IC$_{50}$ [μM] |
|---|---|---|---|
| 27 | 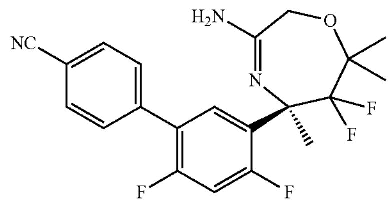 [SMILES: CC1(C)OCC(N)=N[C@](C)(c2cc(-c3ccc(C#N)cc3)c(F)cc2F)C1(F)F] | 0.430$^a$ | |
| 28 | 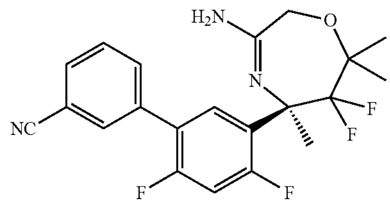 | 0.790$^a$ | |
| 29 | 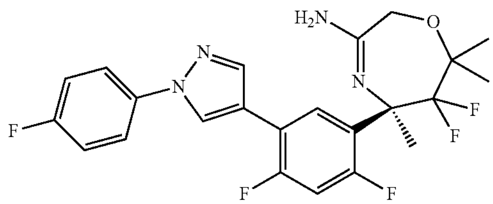 [SMILES: CC1(C)OCC(N)=N[C@](C)(c2cc(-c3cnn(-c4ccc(F)cc4)c3)c(F)cc2F)C1(F)F] | 0.940$^b$ | |
| 30 | 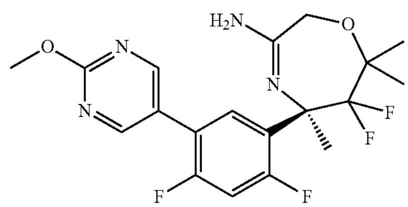 | 0.075$^b$ | |
| 31 | 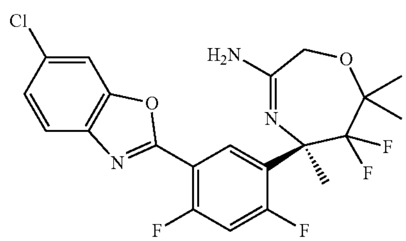 [SMILES: CC1(C)OCC(N)=N[C@](C)(c2cc(-c3nc4ccc(Cl)cc4o3)c(F)cc2F)C1(F)F] | 0.180$^b$ | |
| 32 | 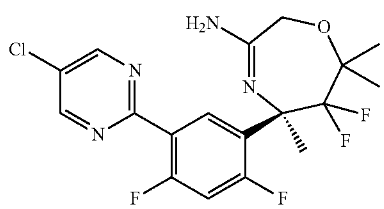 [SMILES: CC1(C)OCC(N)=N[C@](C)(c2cc(-c3ncc(Cl)cn3)c(F)cc2F)C1(F)F] | 0.500$^b$ | |
| 33 | 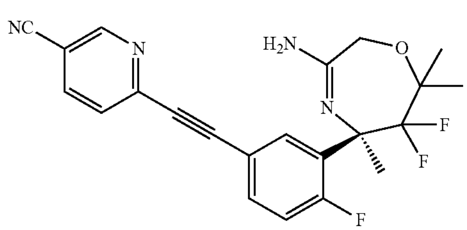 [SMILES: CC1(C)OCC(N)=N[C@](C)(c2cc(C#Cc3ccc(C#N)cn3)ccc2F)C1(F)F] | 0.003b | |

TABLE 1-continued
| Ex. | Structure | BACE1 IC$_{50}$ [μM] | BACE2 IC$_{50}$ [μM] |
|---|---|---|---|
| 34 | 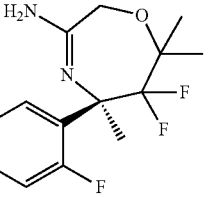 | 0.013b | |
| 35 | 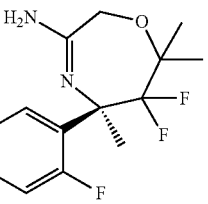 | 0.079b | |
| 36 | 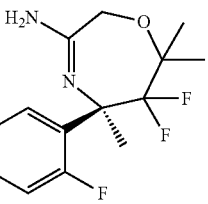 | 0.115b | |
| 37 | 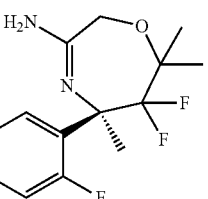 | 0.145b | |
| 38 | 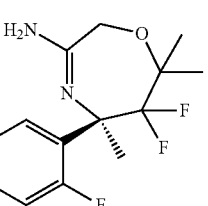 | 0.152$^b$ | |
| 39 | 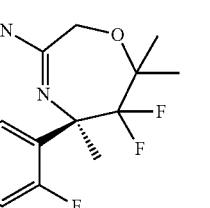 | 0.360b | |
| 40 | 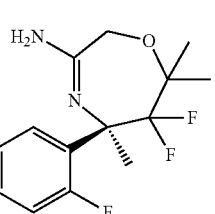 | 0.480b | |

TABLE 1-continued

| Ex. | Structure | BACE1 IC$_{50}$ [µM] | BACE2 IC$_{50}$ [µM] |
|---|---|---|---|
| 41 | 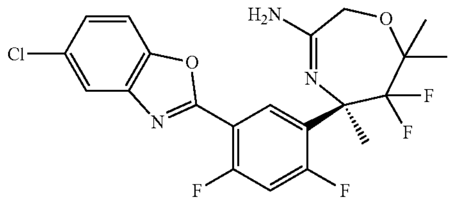 [SMILES: CC1(C)OCC(N)=N[C@](C)(c2cc(-c3nc4cc(Cl)ccc4o3)c(F)cc2F)C1(F)F] | 0.550b | |
| 42 | 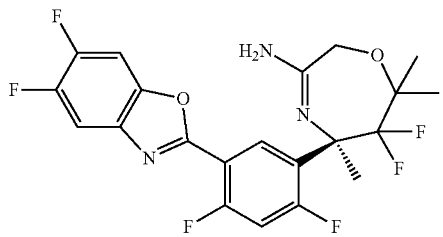 [SMILES: CC1(C)OCC(N)=N[C@](C)(c2cc(-c3nc4cc(F)c(F)cc4o3)c(F)cc2F)C1(F)F] | 0.550b | |
| 43 | 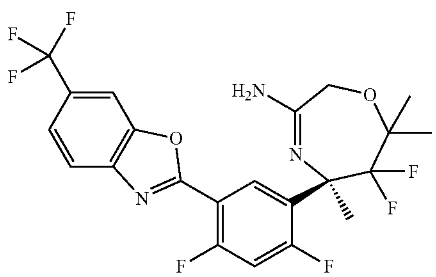 [SMILES: CC1(C)OCC(N)=N[C@](C)(c2cc(-c3nc4ccc(C(F)(F)F)cc4o3)c(F)cc2F)C1(F)F] | 0.070b | |

IC$_{50}$ values of selected examples, $^{a,b}$indicated the respective assays as described above under a) and b).

Pharmaceutical Compositions

The compounds of formula I and the pharmaceutically acceptable salts can be used as therapeutically active substances, e.g. in the form of pharmaceutical preparations. The pharmaceutical preparations can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds of formula I and the pharmaceutically acceptable salts thereof can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also provided by the present invention, as is a process for their production, which comprises bringing one or more compounds of formula I and/or pharmaceutically acceptable salts thereof and, if desired, one or more other therapeutically valuable substances into a galenical administration form together with one or more therapeutically inert carriers.

The dosage can vary within wide limits and will, of course, have to be adjusted to the individual requirements in each particular case. In the case of oral administration the dosage for adults can vary from about 0.01 mg to about 1000 mg per day of a compound of formula I or of the corresponding amount of a pharmaceutically acceptable salt thereof. The daily dosage can be administered as single dose or in divided doses and, in addition, the upper limit can also be exceeded when this is found to be indicated.

The following examples illustrate the present invention without limiting it, but serve merely as representative thereof. The pharmaceutical preparations conveniently contain about 1-500 mg, particularly 1-100 mg, of a compound of formula I. Examples of compositions according to the invention are:

Example A

Tablets of the following composition are manufactured in the usual manner:

TABLE 2 possible tablet composition

| ingredient | mg/tablet | | | |
|---|---|---|---|---|
| | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure

1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Example B-1

Capsules of the following composition are manufactured:

TABLE 3 possible capsule ingredient composition

| ingredient | mg/capsule | | | |
|---|---|---|---|---|
| | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure

1. Mix ingredients 1, 2 and 3 in a suitable mixer for 30 minutes.
2. Add ingredients 4 and 5 and mix for 3 minutes.
3. Fill into a suitable capsule.

The compound of formula I, lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Example B-2

Soft Gelatin Capsules of the following composition are manufactured:

TABLE 4 possible soft gelatin capsule ingredient composition

| ingredient | mg/capsule |
|---|---|
| Compound of formula I | 5 |
| Yellow wax | 8 |
| Hydrogenated Soya bean oil | 8 |
| Partially hydrogenated plant oils | 34 |
| Soya bean oil | 110 |
| Total | 165 |

TABLE 5 possible soft gelatin capsule composition

| ingredient | mg/capsule |
|---|---|
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure

The compound of formula I is dissolved in a warm melting of the other ingredients and the mixture is filled into soft gelatin capsules of appropriate size. The filled soft gelatin capsules are treated according to the usual procedures.

Example C

Suppositories of the following composition are manufactured:

TABLE 6 possible suppository composition

| ingredient | mg/supp. |
|---|---|
| Compound of formula I | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered compound of formula I is added thereto and stirred until it has dispersed completely. The mixture is poured into suppository moulds of suitable size, left to cool; the suppositories are then removed from the moulds and packed individually in wax paper or metal foil.

Example D

Injection solutions of the following composition are manufactured:

TABLE 7

| possible injection solution composition | |
|---|---|
| ingredient | mg/injection solution. |
| Compound of formula I | 3 |
| Polyethylene Glycol 400 | 150 |
| acetic acid | q.s. ad pH 5.0 |
| water for injection solutions | ad 1.0 ml |

Manufacturing Procedure

The compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example E

Sachets of the following composition are manufactured:

TABLE 8

| possible sachet composition | |
|---|---|
| ingredient | mg/sachet |
| Compound of formula I | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |
| Magnesium stearate | 10 |
| Flavoring additives | 1 |
| Total | 2500 |

Manufacturing Procedure

The compound of formula I is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

Experimental Part

The following examples are provided for illustration of the invention. They should not be considered as limiting the scope of the invention, but merely as being representative thereof.

General:

MS: Mass spectra (MS) were measured either with ion spray positive or negative (ISP or ISN) method on a Perkin-Elmer SCIEX API 300 or with electron impact method (EI, 70 eV) on a Finnigan MAT SSQ 7000 spectrometer.

Synthesis of the Intermediate Sulfinyl Imines A2

General Procedure

To a solution of the (R)-(+)-tert-butylsulfinamide (66 mmol) in tetrahydrofuran (350 ml) was added subsequently the ketone A1 (72.6 mmol) and titanium(IV)ethoxide (132 mmol) and the solution was stirred at reflux temperature for 5 h. The mixture was cooled to 22° C., treated with brine (400 ml), the suspension was stirred for 10 min and filtered over Dicalite®. The layers were separated, the aqueous layer was extracted with ethyl acetate, and the combined organic layers were washed with water, dried and concentrated in vacuo. The residue was purified by chromatography on silica using cylohexane/ethyl acetate as the eluent to give the pure sulfinyl imine A2.

Intermediate A2.1

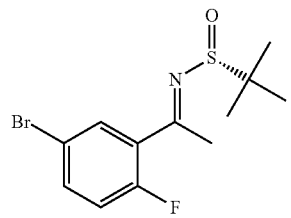 [SMILES: C/C(=N\[S@](=O)C(C)(C)C)c1cc(Br)ccc1F]

Starting from commercially available 1-(2-fluoro-5-bromo-phenyl)-ethanone [CAS No. 477-89-3], the product (R)-2-methyl-propane-2-sulfinic acid [1-(2-fluoro-5-bromo-phenyl)-(E)-ethylidene]-amide was obtained as a pale red oil. MS: m/z=320.3 $[M+H]^+$.

Intermediate A2.2

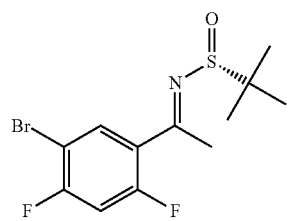 [SMILES: C/C(=N\[S@](=O)C(C)(C)C)c1cc(Br)c(F)cc1F]

Starting from commercially available 1-(5-bromo-2,4-difluorophenyl)-ethanone [CAS No. 864773-64-8] the product (R)-2-methyl-propane-2-sulfinic acid [1-(5-bromo-2,4-difluoro-phenyl)-eth-(E)-ylidene]-amide was obtained as a pale red oil. MS: m/z=338.1 $[M+H]^+$ and 340.1 $[M+2+H]^+$.

Synthesis of the Intermediate Sulfinamide Esters A3

General Procedure (Via Reformatsky Reaction)

In a dry apparatus a suspension of freshly activated zinc powder (1.63 g, 24.9 mmol) in dry tetrahydrofuran (70 ml) was heated under an inert atmosphere to reflux. A solution of the sulfinyl imine A2 (24.9 mmol) and the bromo-acetate (24.9 mmol) in dry tetrahydrofuran (15 ml) was added dropwise over a period of 15 min and the suspension was heated to reflux for 5 h. The cooled mixture was partitioned between aqueous saturated ammonium chloride and ethyl acetate, the organic layer was dried and evaporated. The crude material was purified by flash chromatography using heptane/ethyl acetate as the eluent to give the sulfinamide ester A3.

Intermediate A3.1

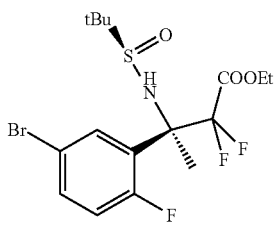 [SMILES: CCOC(=O)C(F)(F)[C@](C)(N[S@](=O)C(C)(C)C)c1cc(Br)ccc1F]

Starting from (R)-2-methyl-propane-2-sulfinic acid [1-(2-fluoro-5-bromo-phenyl)-(E)-ethylidene]-amide and ethyl 2-bromo-2,2-difluoroacetate, the product (3R)-ethyl 3-((R)-1,1-dimethylethylsulfinamido)-2,2-difluoro-3-(2-fluoro-5-bromo-phenyl)butanoate was obtained as an orange oil. MS: m/z=446.1 [M+H]$^+$.

Intermediate A3.2

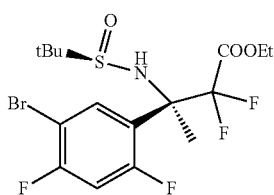 [SMILES: CCOC(=O)C(F)(F)[C@](C)(N[S@](=O)C(C)(C)C)c1cc(Br)c(F)cc1F]

Starting from (R)-2-methyl-propane-2-sulfinic acid [1-(5-bromo-2,4-difluoro-phenyl)-eth-(E)-ylidene]-amide (intermediate A2.2) and ethyl 2-bromo-2,2-difluoroacetate, the product (R)-3-(5-bromo-2,4-difluoro-phenyl)-2,2-difluoro-3-((R)-2-methyl-propane-2-sulfinylamino)-butyric acid ethyl ester was obtained as an orange oil. MS: m/z=462.1 [M+H]$^+$ and 464.1 [M+2+H]$^+$.

Synthesis of the Intermediate Sulfinamide Alcohols A4 and B1

General Procedure

A solution of the sulfinamide ester A3 (12.7 mmol) in dry tetrahydrofuran (50 ml) was treated at 0° C. with lithium borohydride (25.3 mmol) and stirring was continued at 0° C. for 4 h. The reaction mixture was quenched by addition of acetic acid (2 ml) and water (50 ml), extracted with ethyl acetate and the organic layer was dried and evaporated. The residue was purified by chromatography on silica using a mixture of n-heptane and ethyl acetate as the eluent to give the pure intermediate sulfinamide alcohol A4.

Intermediate A4.1

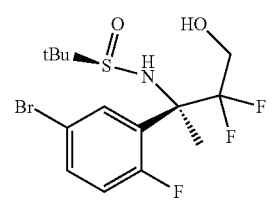 [SMILES: CC(C)(C)[S@@](=O)N[C@](C)(c1cc(Br)ccc1F)C(F)(F)CO]

Starting from (3R)-ethyl 3-((R)-1,1-dimethylethylsulfinamido)-2,2-difluoro-3-(2-fluoro-5-bromo-phenyl)butanoate, the product (S)—N—((R)-2-(5-bromo-2-fluorophenyl)-3,3-difluoro-4-hydroxybutan-2-yl)-2-methylpropane-2-sulfinamide was obtained as a colorless solid. MS: m/z=402.2 [M+H]$^+$.

Intermediate B1.1

(R)—N—((R)-2-(5-Bromo-2-fluorophenyl)-3,3-difluoro-4-hydroxy-4-methylpentan-2-yl)-2-methyl-propane-2-sulfinamide

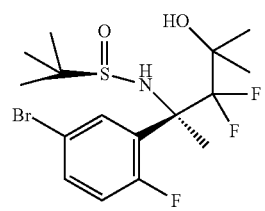 [SMILES: CC(C)(C)[S@@](=O)N[C@](C)(c1cc(Br)ccc1F)C(F)(F)C(C)(C)O]

To a solution of (R)-ethyl 3-(5-bromo-2-fluorophenyl)-3-((R)-1,1-dimethylethylsulfinamido)-2,2-difluorobutanoate (intermediate A3.2) (10.5 g, 23.6 mmol) in anhydrous tetrahydrofuran (150 ml) at −78° C. was added dropwise a solution of methylmagnesium bromide (3.2 M in 2-methyltetrahydrofuran; 59.1 ml, 189 mmol). The cooling bath was removed, and the mixture was stirred at 23° C. for 18 h. Poured cautiously into a saturated solution of ammonium chloride, extracted with ethyl acetate, washed organic layer with brine and dried over sodium sulphate. Removal of the solvent in vacuum left the (R)—N—((R)-2-(5-bromo-2-fluorophenyl)-3,3-difluoro-4-hydroxy-4-methylpentan-2-yl)-2-methylpropane-2-sulfinamide (10.565 g, 23.6 mmol, 99.7% yield) as a yellow gum, which was used in the next step without further purification. MS: m/z=430.1 [(M+H)$^+$] and 432.1 [(M+2+H)$^+$].

Intermediate B.1.2

(R)—N—((R)-2-(5-Bromo-2,4-difluorophenyl)-3,3-difluoro-4-hydroxy-4-methylpentan-2-yl)-2-methyl-propane-2-sulfinamide

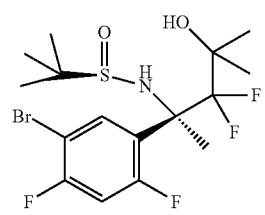

To a solution of (R)-ethyl 3-(5-bromo-2,4-difluorophenyl)-3-(((R)-1,1-dimethylethylsulfinamido)-2,2-difluorobutanoate (intermediate A3.2) (23.1 g, 50.0 mmol) in anhydrous tetrahydrofuran (700 ml) at −78° C. was added dropwise a solution of methylmagnesium bromide (3.2 M in 2-methyltetrahydrofuran; 125 ml, 400 mmol). The cooling bath was removed and the mixture was stirred at 23° C. for 18 h. Poured cautiously into a saturated solution of ammonium chloride, extracted with ethyl acetate, washed organic layer with brine and dried over sodium sulphate. Removal of the solvent in vacuum left the (R)—N—((R)-2-(5-bromo-2,4-difluorophenyl)-3,3-difluoro-4-hydroxy-4-methylpentan-2-yl)-2-methyl-propane-2-sulfinamide (21.4 g, 47.7 mmol, 95.5% yield) as a light yellow solid, which was used in the next step without further purification. MS: m/z=448.1 [(M+H)$^+$] and 450.1 [(M+2+H)$^+$].

Synthesis of the Intermediate Sulfinamide Nitrile A5

General Procedure

To a solution of the sulfinamide alcohol A4 (4.1 mmol) in dichloromethane (23 ml) was subsequently added at 22° C. 2-bromoacetonitrile (6.2 mmol), silver(I) oxide (1.9 g) and tetrabutylammonium iodide (0.30 g) and stirring was continued for 2 h. The suspension was filtered, and the filtrate was washed with aqueous saturated solution of sodium hydrogencarbonate. The organic layer was dried and evaporated to give the crude sulfinamide nitrile A5 which was used without further purification.

Intermediate A5.1

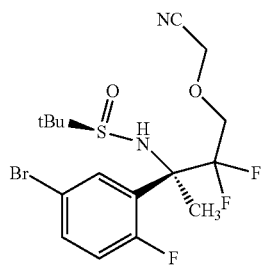

Starting from (S)—N—((R)-2-(5-bromo-2-fluorophenyl)-3,3-difluoro-4-hydroxybutan-2-yl)-2-methylpropane-2-sulfinamide, the product (S)—N—((R)-2-(5-bromo-2-fluorophenyl)-4-(cyanomethoxy)-3,3-difluorobutan-2-yl)-2-methylpropane-2-sulfinamide was obtained as a colorless oil. MS: m/z=441.1 [M+H]$^+$.

Synthesis of the Intermediate Amino Nitrile A6

General Procedure

A solution of the sulfinamide nitrile A5 (4.25 mmol) in 1,4-dioxane (20 ml) was treated with a solution of hydrochloric acid in 1,4-dioxane (4 M, 5.3 ml) and stirring was continued at 22° C. for 1 h. The mixture was diluted with ethyl acetate, washed with saturated aqueous solution of sodium hydrogencarbonate; the organic layer was dried and evaporated. The crude material was purified on silica using n-heptane/ethyl acetate as the eluent to give the pure amino nitrile A6.

Intermediate A6.1

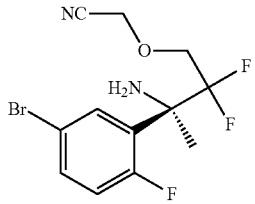

Starting from (S)—N4R)-2-(5-bromo-2-fluorophenyl)-4-(cyanomethoxy)-3,3-difluorobutan-2-yl)-2-methylpropane-2-sulfinamide, the product (R)-2-(3-amino-3-(5-bromo-2-fluorophenyl)-2,2-difluorobutoxy)acetonitrile was obtained as a colorless oil. MS: m/z=337.2 [M+H]$^+$.

Synthesis of the Intermediate 1,4-oxazepine A7

General Procedure

To a solution of the amino nitrile A6 (2.20 mmol) in toluene (38 ml) was added at 22° C. a solution of trimethylaluminium in toluene (2 M, 1.2 ml) and the mixture was heated to 80° C. for 1 h. The mixture was cooled to 0° C., diluted with saturated aqueous solution of sodium carbonate; then the aqueous layer was extracted with ethyl acetate. The combined organic layers were dried, evaporated and the residue purified by chromatography on NH$_2$-silica using n-heptane/ethyl acetate as the eluent to give the pure 1,4-oxazepine A7.

Intermediate A7.1

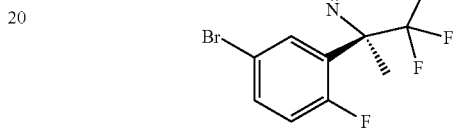

Starting from (R)-2-(3-amino-3-(5-bromo-2-fluorophenyl)-2,2-difluorobutoxy)acetonitrile, the product (R)-5-(5-bromo-2-fluorophenyl)-6,6-difluoro-5-methyl-2,5,6,7-tetrahydro-1,4-oxazepin-3-amine was obtained as a colorless oil. MS: m/z=337.2 [M+H]$^+$ and 339.2 [M+2+H]$^+$.

Synthesis of the Intermediate DMTr-1,4-Oxazepine A8.1

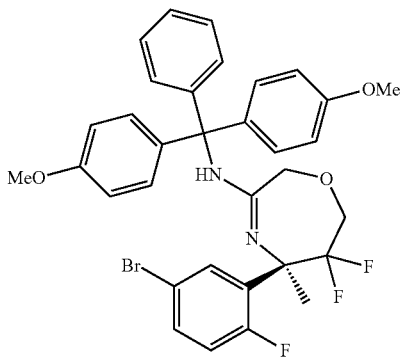 [SMILES: COc1ccc(C(NC2=N[C@](C)(c3cc(Br)ccc3F)C(F)(F)COC2)(c2ccccc2)c2ccc(OC)cc2)cc1]

To a solution of (R)-5-(5-bromo-2-fluorophenyl)-6,6-difluoro-5-methyl-2,5,6,7-tetrahydro-1,4-oxazepin-3-amine (intermediate A7.1) (9.0 mmol) in dichloromethane (150 ml) was subsequently added at 0° C. triethylamine (18.0 mmol) and 4,4'-dimethoxytriphenylmethyl chloride (9.9 mmol) and stirring was continued at 22° C. for 2 hours. For the workup, the mixture was washed with saturated an aqueous solution of ammonium chloride. The organic layer was dried, evaporated at reduced pressure, and the residue was purified by chromatography on silica using cyclohexane/ethyl acetate to give pure (R)—N-(bis(4-methoxyphenyl)(phenyl)methyl)-5-(5-bromo-2-fluorophenyl)-6,6-difluoro-5-methyl-2,5,6,7-tetrahydro-1,4-oxazepin-3-amine (A8.1) as a colorless foam. MS (ISP): m/z=639.3 [M+H]$^+$ and 641.4 [M+2+H]$^+$.

Synthesis of the O-Allyl Compounds B2 from the Alcohols B1

General Procedure:

To a solution of the alcohol B1 (29.25 mmol) in dry tetrahydrofuran (290 mL) at 23° C. was added commercially available allyl tert-butyl carbonate (5.56 g, 35.1 mmol). Argon was bubbled through the solution and tetrakistriphenylphosphinepalladium(0) (1.02 g, 878 µmol) was added, and the mixture was stirred at 70° C. for 8 hours. Cooled to 23° C., extracted with ethyl acetate and water, dried the organic layer over sodium sulphate, filtered and evaporated totally. The residue was purified by chromatography on silica gel with ethyl acetate 0%-80% in heptane to give the O-allylated compounds B2.

Intermediate B2.1

(R)—N—((R)-4-(allyloxy)-2-(5-bromo-2-fluorophenyl)-3,3-difluoro-4-methylpentan-2-yl)-2-methylpropane-2-sulfinamide

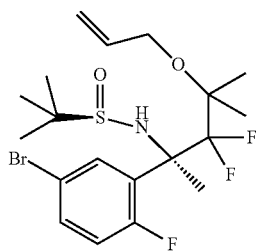 [SMILES: C=CCOC(C)(C)C(F)(F)[C@](C)(N[S@](=O)C(C)(C)C)c1cc(Br)ccc1F]

The compound was prepared from (R)—N—((R)-2-(5-bromo-2-fluorophenyl)-3,3-difluoro-4-hydroxy-4-methylpentan-2-yl)-2-methylpropane-2-sulfinamide (intermediate B1.1) (12.58 g; 29.25 mmol). The (R)—N—((R)-4-(allyloxy)-2-(5-bromo-2-fluorophenyl)-3,3-difluoro-4-methylpentan-2-yl)-2-methylpropane-2-sulfinamide (9.5 g, 20.2 mmol, 69% yield) was obtained as a light yellow solid. MS: m/z=470.0 [(M+H)⁺] and 472.0 [(M+2+H)⁺].

Intermediate B2.2

(R)—N—((R)-4-(allyloxy)-2-(5-bromo-2,4-difluorophenyl)-3,3-difluoro-4-methylpentan-2-yl)-2-methylpropane-2-sulfinamide

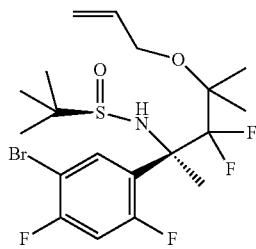 [SMILES: C=CCOC(C)(C)C(F)(F)[C@](C)(N[S@](=O)C(C)(C)C)c1cc(Br)c(F)cc1F]

The compound was prepared from (R)—N—((R)-2-(5-bromo-2,4-difluorophenyl)-3,3-difluoro-4-hydroxy-4-methylpentan-2-yl)-2-methylpropane-2-sulfinamide (intermediate B1.2) (21.4 g; 47.7 mmol). The (R)—N—((R)-4-(allyloxy)-2-(5-bromo-2,4-difluorophenyl)-3,3-difluoro-4-methylpentan-2-yl)-2-methylpropane-2-sulfinamide (16.15 g, 33.1 mmol, 69% yield) was obtained as a light brown oil. MS: m/z=488.1 [(M+H)⁺] and 490.0 [(M+2+H)⁺].

Synthesis of the Acids B3 from the Allyl Ethers B2

General Procedure:

To a solution of the allyl ether B2 (20.2 mmol) in ethyl acetate (95 mL), acetonitrile (95 mL) and water (142 mL) at 23° C. was added sodium periodate (28.1 g, 131 mmol) followed by ruthenium(III) chloride hydrate (91 mg, 0.4 mmol), and the mixture was stirred at 23° C. for 3 hours. The reaction mixture was diluted with ethyl acetate and extracted with hydrochloric acid (1M) and diluted solution of sodium hydrogensulfite. The organic layer was dried over sodium sulphate, filtered off, evaporated totally and dried in high vacuum to give the crude product (acid B3), which was used without further purification.

Intermediate B3.1

(R)-2-(4-(5-Bromo-2-fluorophenyl)-4-(1,1-dimethylethylsulfonamido)-3,3-difluoro-2-methylpentan-2-yloxy)acetic acid

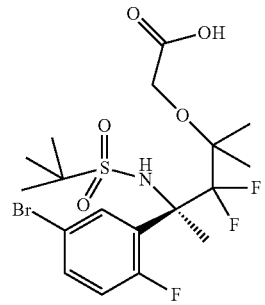 [SMILES: CC(C)(OCC(=O)O)C(F)(F)[C@](C)(NS(=O)(=O)C(C)(C)C)c1cc(Br)ccc1F]

The compound was prepared from (R)—N—((R)-4-(allyloxy)-2-(5-bromo-2-fluorophenyl)-3,3-difluoro-4-methylpentan-2-yl)-2-methylpropane-2-sulfinamide (intermediate B2.1) (9.5 g; 20.2 mmol). The (R)-2-(4-(5-bromo-2-fluorophenyl)-4-(1,1-dimethylethylsulfonamido)-3,3-difluoro-2-methylpentan-2-yloxy)acetic acid (10.2 g, 20.2 mmol, 100% yield) was obtained as a light yellow foam. MS (ISN): m/z=502.0 [(M−H)⁻] and 503.9 [(M+2-H)⁻].

Intermediate B3.2

(R)-2-(4-(5-Bromo-2,4-difluorophenyl)-4-(1,1-dimethylethylsulfonamido)-3,3-difluoro-2-methylpentan-2-yloxy)acetic acid

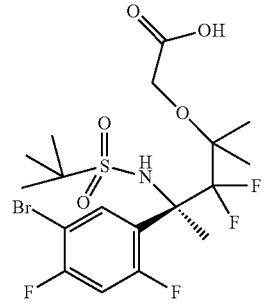 [SMILES: CC(C)(OCC(=O)O)C(F)(F)[C@](C)(NS(=O)(=O)C(C)(C)C)c1cc(Br)c(F)cc1F]

The compound was prepared from (R)—N—((R)-4-(allyloxy)-2-(5-bromo-2,4-difluorophenyl)-3,3-difluoro-4-methylpentan-2-yl)-2-methylpropane-2-sulfinamide (intermediate B2.2) (16.14 g; 33 mmol). The (R)-2-(4-(5-bromo-2,4-difluorophenyl)-4-(1,1-dimethylethylsulfonamido)-3,3-difluoro-2-methylpentan-2-yloxy)acetic acid (17.3 g, 33.1 mmol, 100% yield) was obtained as a light grey solid. MS (ISN): m/z=520.0 [(M−H)⁻] and 521.9 [(M+2-H)⁻].

Synthesis of the Ethyl Esters B4 from the Acids B3

General Procedure:

To a solution of the acid B3 (18.2 mmol) in ethanol (200 mL) at 23° C. was dropwise added thionyl chloride (5.3 mL, 72.8 mmol), and the mixture was stirred at reflux for 18 hours. Cooled to 23° C., diluted with ethyl acetate and extracted with saturated solution of sodium hydrogencarbonate and brine. Dried over sodium sulphate, filtered off and evaporated totally to give the crude ethyl esters B4, which were used without further purification.

Intermediate B4.1

(R)-Ethyl 2-(4-(5-bromo-2-fluorophenyl)-4-(1,1-dimethylethylsulfonamido)-3,3-difluoro-2-methylpentan-2-yloxy)acetate

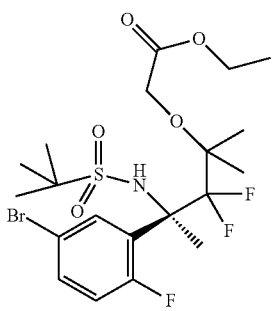 [SMILES: CCOC(=O)COC(C)(C)C(F)(F)[C@](C)(NS(=O)(=O)C(C)(C)C)c1cc(Br)ccc1F]

The compound was prepared from (R)-2-(4-(5-bromo-2-fluorophenyl)-4-(1,1-dimethylethylsulfonamido)-3,3-difluoro-2-methylpentan-2-yloxy)acetic acid (intermediate B3.1) (10.2 g; 18.2 mmol). The (R)-ethyl 2-(4-(5-bromo-2-fluorophenyl)-4-(1,1-dimethylethylsulfonamido)-3,3-difluoro-2-methylpentan-2-yloxy)acetate (10 g, 103% yield) was obtained as a light brown solid. MS (ISN): m/z=530.2 [(M−H)⁻] and 532.0 [(M+2-H)⁻].

Intermediate B4.2

(R)-Ethyl 2-(4-(5-bromo-2,4-difluorophenyl)-4-(1,1-dimethylethylsulfonamido)-3,3-difluoro-2-methylpentan-2-yloxy)acetate

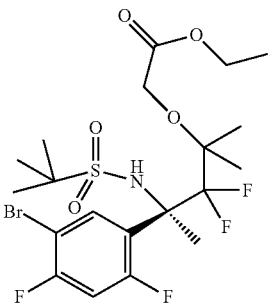 [SMILES: CCOC(=O)COC(C)(C)C(F)(F)[C@](C)(NS(=O)(=O)C(C)(C)C)c1cc(Br)c(F)cc1F]

The compound was prepared from (R)-2-(4-(5-bromo-2,4-difluorophenyl)-4-(1,1-dimethylethylsulfonamido)-3,3-difluoro-2-methylpentan-2-yloxy)acetic acid (intermediate B3.2) (17.1 g; 33 mmol). The (R)-ethyl 2-(4-(5-bromo-2,4-difluorophenyl)-4-(1,1-dimethylethylsulfonamido)-3,3-difluoro-2-methylpentan-2-yloxy)acetate (20.55 g, 37.3 mmol, 113% yield) was obtained as a light brown oil. MS (ISP): m/z=550.2 [(M+H)⁺] and 552.3 [(M+2+H)⁺].

Synthesis of the Amino Esters B5 from the Sulfonamides B4

General Procedure:

To a solution of the sulfonamide B4 (18.8 mmol) in dichloromethane (190 mL) at 0° C. was dropwise added a 0.25 M solution of trifluoromethanesulfonic acid (225 mL, 56.3 mmol) and the mixture was stirred at 23° C. for 30 minutes. Poured into a saturated solution of sodium hydrogencarbonate, extracted with dichloromethane, dried the organic layer over sodium sulphate, filtered off and evaporated totally to give the crude amino esters B5, which were used without further purification or alternatively purified by silica gel column chromatography with heptane and ethyl acetate as the eluent.

Intermediate B5.1

(R)-Ethyl 2-(4-amino-4-(5-bromo-2-fluorophenyl)-3,3-difluoro-2-methylpentan-2-yloxy)acetate

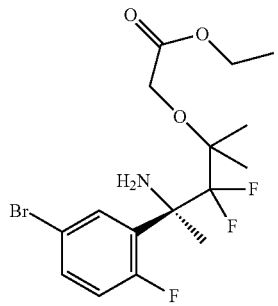 [SMILES: CCOC(=O)COC(C)(C)C(F)(F)[C@](C)(N)c1cc(Br)ccc1F]

The compound was prepared from (R)-ethyl 2-(4-(5-bromo-2-fluorophenyl)-4-(1,1-dimethylethylsulfonamido)-

3,3-difluoro-2-methylpentan-2-yloxy)acetate (intermediate B4.1) (10.2 g; 18.2 mmol). The (R)-ethyl 2-(4-amino-4-(5-bromo-2-fluorophenyl)-3,3-difluoro-2-methylpentan-2-yloxy)acetate (6.85 g, 16.6 mmol, 88.5% yield) was obtained as a light yellow oil. MS: m/z=412.1 [(M+H)+] and 414.2 [(M+2+H)+].

Intermediate B5.2

(R)-Ethyl 2-(4-amino-4-(5-bromo-2,4-difluorophenyl)-3,3-difluoro-2-methylpentan-2-yloxy)acetate

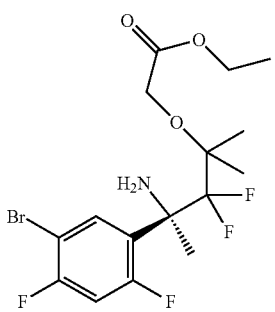 [SMILES: CCOC(=O)COC(C)(C)C(F)(F)[C@](C)(N)c1cc(Br)c(F)cc1F]

The compound was prepared from (R)-ethyl 2-(4-(5-bromo-2,4-difluorophenyl)-4-(1,1-dimethylethylsulfonamido)-3,3-difluoro-2-methylpentan-2-yloxy)acetate (intermediate B4.2) (20.55 g; 37.3 mmol). The (R)-ethyl 2-(4-amino-4-(5-bromo-2,4-difluorophenyl)-3,3-difluoro-2-methylpentan-2-yloxy)acetate (16.1 g, 37.4 mmol, 100% yield) was obtained as a light yellow oil. MS: m/z=430.1 [(M+H)+] and 432.2 [(M+2+H)+].

Synthesis of the Lactams B6 from the Amino Esters B5

Intermediate B6.1

(R)-5-(5-Bromo-2-fluorophenyl)-6,6-difluoro-5,7,7-trimethyl-[1,4]oxazepan-3-one

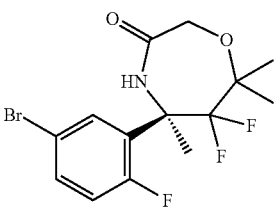 [SMILES: CC1(C)OCC(=O)N[C@](C)(c2cc(Br)ccc2F)C1(F)F]

To a solution of (R)-ethyl 2-(4-amino-4-(5-bromo-2-fluorophenyl)-3,3-difluoro-2-methylpentan-2-yloxy)acetate (intermediate B5.1) (6.85 g, 16.6 mmol) in toluene (205 ml) at 23° C. was added dropwise trimethylaluminum (2 M in toluene, 10.8 ml, 21.6 mmol) and the light yellow solution was stirred at 23° C. for 2 h. Poured into a saturated solution of sodium hydrogencarbonate, extracted with ethyl acetate, washed organic layer with brine, dried over sodium sulphate, filtered off and evaporated totally. Dried at high vacuum to give the (R)-5-(5-bromo-2-fluorophenyl)-6,6-difluoro-5,7,7-trimethyl-1,4-oxazepan-3-one (5.95 g, 16.2 mmol, 97.8% yield) as a light yellow solid, which was used without further purification. MS: m/z=366.2 [(M+H)+] and 368.1 [(M+2+H)+].

Intermediate B6.2

(R)-5-(5-Bromo-2,4-difluorophenyl)-6,6-difluoro-5,7,7-trimethyl-[1,4]oxazepan-3-one

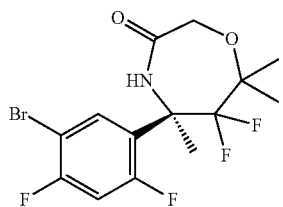 [SMILES: CC1(C)OCC(=O)N[C@](C)(c2cc(Br)c(F)cc2F)C1(F)F]

Prepared in a manner analogous to that described for intermediate B6.1 from (R)-ethyl 2-(4-amino-4-(5-bromo-2,4-difluorophenyl)-3,3-difluoro-2-methylpentan-2-yloxy)acetate (intermediate B5.2) (16.1 g; 37.4 mmol). After silica gel column chromatography with heptane and ethyl acetate as the eluent the (R)-5-(5-bromo-2,4-difluorophenyl)-6,6-difluoro-5,7,7-trimethyl-[1,4]oxazepan-3-one (9.0 g, 23.4 mmol, 63% yield) was obtained as an off-white solid. MS: m/z=384.2 [(M+H)+] and 386.1 [(M+2+H)+].

Synthesis of the Thiolactams B7 from the Lactams B6

Intermediate B7.1

(R)-5-(5-Bromo-2-fluorophenyl)-6,6-difluoro-5,7,7-trimethyl-[1,4]oxazepan-3-thione

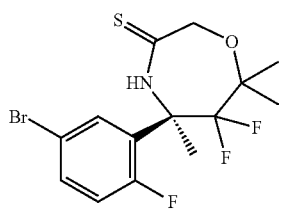

A solution of (R)-5-(5-bromo-2-fluorophenyl)-6,6-difluoro-5,7,7-trimethyl-[1,4]oxazepan-3-one (intermediate B6.1) (1.11 g, 2.84 mmol) in dioxane (80 ml) was treated at room temperature with 2,4-bis-(4-methoxy-phenyl)-[1,3,2,4] dithiadiphosphetane 2,4-disulfide (Lawesson's reagent) (1.19 g, 2.84 mmol). The mixture was stirred at 85° C. for 15 hours. For the workup, the solvent was evaporated at reduced pressure, then the residue distributed between ethyl acetate and a saturated solution of sodium hydrogencarbonate. The organic layer was washed with brine, then dried over sodium sulphate and evaporated at reduced pressure. Purification of the crude product by chromatography on silica-amine phase using a gradient of heptane/ethyl acetate=100:0 to 85:15 yielded the (R)-5-(5-bromo-2-fluorophenyl)-6,6-difluoro-5,7,7-trimethyl-[1,4]oxazepan-3-one as a light yellow foam (971 mg, 89% yield). MS: m/z=382.2 [(M+H)+] and 384.0 [(M+2+H)+].

Intermediate B7.2

(R)-5-(5-Bromo-2,4-fluorophenyl)-6,6-difluoro-5,7,7-trimethyl-[1,4]oxazepan-3-thione

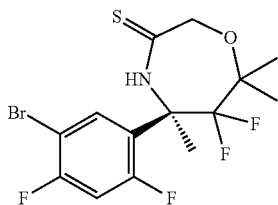

The compound was prepared in analogy to the preparation of intermediate B7.1 starting from (R)-5-(5-bromo-2,4-difluorophenyl)-6,6-difluoro-5,7,7-trimethyl-[1,4]oxazepan-3-one (intermediate B6.2) (2.0 g, 5.21 mmol). The (R)-5-(5-bromo-2,4-difluorophenyl)-6,6-difluoro-5,7,7-trimethyl-[1,4]oxazepan-3-thione was obtained in quantitative yield as a light yellow oil. MS (ISN): m/z=397.4 [M–H]$^-$ and 399.8 [M+2-H]$^-$.

Synthesis of the Aminooxazepines B8 from the Thiolactames B7

Intermediate B8.1

(R)-5-(5-Bromo-2-fluoro-phenyl)-6,6-difluoro-5,7,7-trimethyl-2,5,6,7-tetrahydro-[1,4]oxazepin-3-ylamine

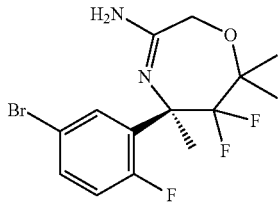 [SMILES: CC1(C)OCC(N)=N[C@](C)(c2cc(Br)ccc2F)C1(F)F]

A solution of (R)-5-(5-bromo-2-fluorophenyl)-6,6-difluoro-5,7,7-trimethyl-1,4-oxazepane-3-thione (intermediate B7.1) (959 mg, 2.51 mmol) in methanol (27 ml) was treated consecutively with ammonia in methanol (7M; 21.5 ml, 151 mmol) and dropwise with tert-butylhydroperoxide (70% in water; 2.07 ml, 15.1 mmol). The reaction mixture was stirred at room temperature overnight. For the workup, the methanol was evaporated at reduced pressure, and the residue partitioned between dichloromethane and water. The organic layer was washed with brine, then the 2 aqueous layers extracted with dichloromethane. The combined organic layers were dried over sodium sulphate and evaporated at reduced pressure. The first purification of the crude product by chromatography on silica-amine phase using a gradient of heptane/ethyl acetate=100:0 to 72:28 was followed by a filtration through a SCX-2 cartridge. The cartridge was washed with a mixture of heptane and ethyl acetate and the product was recovered eluting with a solution of ammonia in methanol (7M). The (R)-5-(5-bromo-2-fluoro-phenyl)-6,6-difluoro-5,7,7-trimethyl-2,5,6,7-tetrahydro-[1,4]oxazepin-3-ylamine was obtained as a light yellow foam (463 mg, 51% yield). MS (ISP): m/z=365.2 [(M+H)$^+$] and 367.1 [(M+2+H)$^+$].

Intermediate B8.2

(R)-5-(5-Bromo-2,4-difluoro-phenyl)-6,6-difluoro-5,7,7-trimethyl-2,5,6,7-tetrahydro-[1,4]oxazepin-3-ylamine

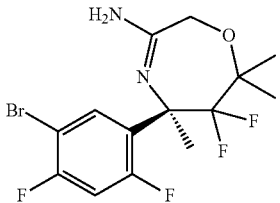 [SMILES: CC1(C)OCC(N)=N[C@](C)(c2cc(Br)c(F)cc2F)C1(F)F]

The compound was prepared in analogy to the preparation of intermediate B8.1 starting from (R)-5-(5-bromo-2,4-difluorophenyl)-6,6-difluoro-5,7,7-trimethyl-[1,4]oxazepan-3-thione (intermediate B7.2) (2.2 g, 5.5 mmol). The (R)-5-(5-bromo-2,4-difluoro-phenyl)-6,6-difluoro-5,7,7-trimethyl-2,5,6,7-tetrahydro-[1,4]oxazepin-3-ylamine (870 mg, 41% yield) was obtained as a light yellow oil. MS (ISP): m/z=383.2 [(M+H)$^+$] and 385.0 [(M+2+H)$^+$].

Synthesis of the Intermediate DMTr-1,4-oxazepine B9.1

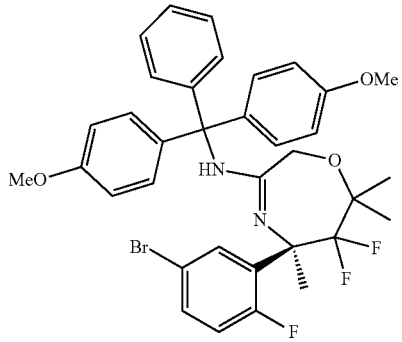 [SMILES: COc1ccc(C(NC2=N[C@](C)(c3cc(Br)ccc3F)C(F)(F)C(C)(C)OC2)(c2ccccc2)c2ccc(OC)cc2)cc1]

Prepared in a manner analogous to that described for the preparation of intermediate A8.1 starting from (R)-5-(5-bromo-2-fluorophenyl)-6,6-difluoro-5,7,7-trimethyl-2,5,6,7-tetrahydro-1,4-oxazepin-3-amine (intermediate B8.1) (302.6 mg, 829 µmol). The (R)—N-(bis(4-methoxyphenyl)(phenyl)methyl)-5-(5-bromo-2-fluorophenyl)-6,6-difluoro-5,7,7-trimethyl-2,5,6,7-tetrahydro-1,4-oxazepin-3-amine (418 mg, 74% yield) was obtained as a white foam. MS (ISP): m/z=667.2 [M+H]+ and 669.3 [M+2+H]+.

Synthesis of the Intermediate Boronic Ester B10.1 from B9.2

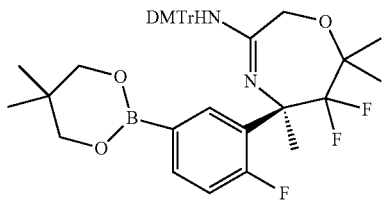

A dried pressure tube was charged with potassium acetate (411 mg, 4.2 mmol), bis(triphenylphosphin)palladium(II) chloride (41.7 mg, 58.2 µmol), 5,5,5',5'-tetramethyl-2,2'-bi(1,3,2-dioxaborinane) (316 mg, 1.4 mmol), and dioxane (13 ml). After addition of (R)—N-(bis(4-methoxyphenyl)(phenyl) methyl)-5-(5-bromo-2-fluorophenyl)-6,6-difluoro-5,7,7-trimethyl-2,5,6,7-tetrahydro-1,4-oxazepin-3-amine (intermediate B9.1) the tube was flushed with argon, sealed and heated at 110° C. for 15 hours. For the workup, the reaction mixture was cooled to room temperature and evaporated at reduced pressure. The residue was partitioned between dichloromethane and water. The organic layer was washed with brine, dried over sodium sulphate and evaporated at reduced pressure. The crude [bis-(4-methoxy-phenyl)-phenyl-methyl]-{(R)-5-[5-(5,5-dimethyl-[1,3,2]dioxaborinan-2-yl)-2-fluoro-phenyl]-6,6-difluoro-5,7,7-trimethyl-2,5,6,7-tetrahydro-[1,4]oxazepin-3-yl}-amine (918 mg) was obtained as a light brown foam and engaged in the next step without further purification.

Intermediate B10.2

[Bis-(4-methoxy-phenyl)-phenyl-methyl]-{(R)-6,6-difluoro-5-[2-fluoro-5-(4,4,5,5-tetramethyl-[1,3,2]dioxaborolan-2-yl)-phenyl]-5,7,7-trimethyl-2,5,6,7-tetrahydro-[1,4]oxazepin-3-yl}-amine

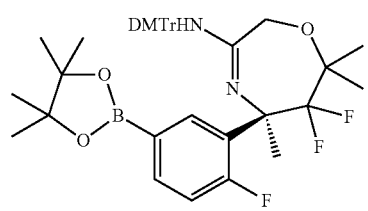

The compound was prepared in analogy to the preparation of intermediate B10.1 starting from (R)—N-(bis(4-methoxyphenyl)(phenyl)methyl)-5-(5-bromo-2-fluorophenyl)-6,6-difluoro-5,7,7-trimethyl-2,5,6,7-tetrahydro-1,4-oxazepin-3-amine (intermediate B9.1) and bis(pinacolato)diboron (CAS 73183-34-3) yielding the title compound to be used in the next step without further purification.

Synthesis of the Intermediate Iodo Lactame B6".1

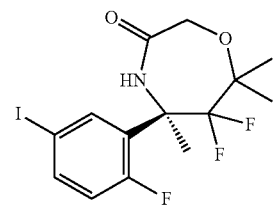 [SMILES: CC1(C)OCC(=O)N[C@](C)(c2cc(I)ccc2F)C1(F)F]

A solution of (R)-5-(5-bromo-2-fluorophenyl)-6,6-difluoro-5,7,7-trimethyl-1,4-oxazepan-3-one (intermediate B6.1) (200 mg, 546 µmol) in dioxane (2 ml) was treated consecutively with trans-N,N'-dimethyl-1,2-cyclohexanediamine (16.0 mg, 109 µmol), copper(I)iodide (10.6 mg, 54.6 µmol), and sodium iodide (165 mg, 1.09 mmol). The reaction mixture was stirred at 110° C. for 15 hours. Following TLC the reaction was incomplete. Another amount of copper(I) iodide (10.6 mg, 54.6 µmol), trans-N,N'-dimethyl-1,2-cyclohexanediamine (16.0 mg, 109 µmol), and sodium iodide (165 mg, 1.09 mmol) was added. Stirring was continued at 110° C. during the weekend. For the workup, the reaction mixture was evaporated at reduced pressure and the residue was purified by chromatography on silica gel using a gradient of heptane/ ethyl acetate=100:0 to 90:60 as the eluent. The (R)-6,6-difluoro-5-(2-fluoro-5-iodo-phenyl)-5,7,7-trimethyl-[1,4]oxazepan-3-one (217 mg, 96% yield) was obtained as light yellow viscous oil. MS (ISP): m/z=414.1 [M+H]+.

Synthesis of the Intermediate Boronic Ester D1.1 from Bromo Lactame B6'

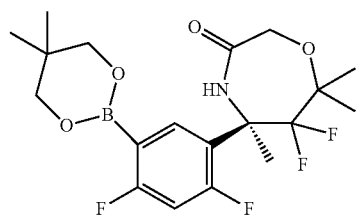

A dried pressure tube was charged with (R)-5-(5-bromo-2,4-difluorophenyl)-6,6-difluoro-5,7,7-trimethyl-1,4-oxazepan-3-one (177 mg, 461 µmol) (intermediate B6.1), 5,5,5',5'-tetramethyl-2,2'-bi(1,3,2-dioxaborinane) (312 mg, 1.38 mmol), potassium acetate (226 mg, 2.3 mmol) and dioxane (5.8 ml). After addition of bis(triphenylphosphin) palladium (II)chloride (16.2 mg, 23.0 µmol) the tube was flushed with argon, sealed and heated at 80° C. for 3 hours. For the workup, the reaction mixture was cooled to room temperature, diluted with water and extracted twice with dichloromethane. The combined organic layers were washed with water and brine, dried over sodium sulphate and evaporated. The crude (R)-5-[5-(5,5-dimethyl-[1,3,2]dioxaborinan-2-yl)-2,4-difluorophenyl]-6,6-difluoro-5,7,7-trimethyl-[1,4]oxazepan-3-one was engaged in the next step without further purification.

Intermediate D1.2

(R)-5-[5-(5,5-Dimethyl-[1,3,2]dioxaborinan-2-yl)-2-fluoro-phenyl]-6,6-difluoro-5,7,7-trimethyl-[1,4]oxazepan-3-one

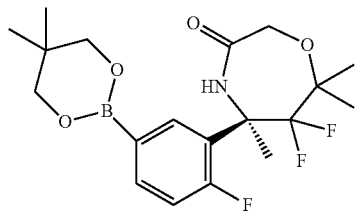

The compound was prepared in analogy to the preparation of intermediate D1.1 starting from (R)-5-(5-bromo-2-fluorophenyl)-6,6-difluoro-5,7,7-trimethyl-1,4-oxazepan-3-one (intermediate B6.1) (275 mg, 684 µmol). (R)-5-[5-(5,5-dimethyl-[1,3,2]dioxaborinan-2-yl)-2-fluoro-phenyl]-6,6-difluoro-5,7,7-trimethyl-[1,4]oxazepan-3-one (207 mg, 76% yield) as a white foam.

Example 1

Method A (R)-6,6-Difluoro-5-(2-fluoro-5-pyrimidin-5-yl-phenyl)-5-methyl-2,5,6,7-tetrahydro-[1,4]oxazepin-3-ylamine formate A degassed solution of (R)-5-(5-bromo-2-fluorophenyl)-6,6-difluoro-5-methyl-2,5,6,7-tetrahydro-1,4-oxazepin-3-amine (20 mg, 59.3 µmol (intermediate A7.1), pyrimidine-5-boronic acid (8.8 mg, 71.2 µmol), and cesium carbonate (77.3 mg, 237 µmol) in a mixture of dimethoxyethane (1 ml) and water (0.5 ml) was treated in a tube under an argon atmosphere with [1,1'-bis(diphenylphosphino)ferrocene]dichloropalladium(II) (CAS 72287-26-4) (2.2 mg, 3.0 µmol). The tube was sealed and heated to 80° C. for 70 minutes. In order to complete the reaction, pyrimidine-5-boronic acid (2.2 mg, 17.8 µmol) and [1,1'-bis(diphenylphosphino)-ferrocene]dichloropalladium(II) (2.2 mg, 3.0 µmol) were added and stirring continued at 80° C. for 10 minutes. For the workup, the reaction mixture was cooled to room temperature and diluted with water (1.5 ml). After addition of formic acid (0.5 ml) the mixture was filtrated and the filtrate purified by preparative HPLC. The (R)-6,6-difluoro-5-(2-fluoro-5-pyrimidin-5-yl-phenyl)-5-methyl-2,5,6,7-tetrahydro-[1,4]oxazepin-3-ylamine was obtained as a light brown amorphous material (n off-white solid (14 mg, 59% yield). MS (ISP): m/z=337.2 [M+H]+.

Example 2

Method B (R)-6,6-Difluoro-5-(2-fluoro-5-pyrimidin-5-yl-phenyl)-5,7,7-trimethyl-2,5,6,7-tetrahydro-[1,4]oxazepin-3-ylamine a) (R)-6,6-Difluoro-5-(2-fluoro-5-pyrimidin-5-yl-phenyl)-5,7,7-trimethyl-[1,4]oxazepan-3-one In analogy to the procedure described in Example 1 (method A), the reaction of (R)-5-(5-bromo-2-fluorophenyl)-6,6-difluoro-5,7,7-trimethyl-1,4-oxazepan-3-one (intermediate B6.1) (311 mg, 849 µmol) and pyrimidin-5-boronic acid (116 mg, 934 µmol) in tetrahydrofuran (8 ml) and water (4 ml) with [1,1'-bis(diphenylphosphino) ferrocene]dichloropalladium(II) dichloromethane complex (34.7 mg, 42.5 µmol) as the catalyst yielded, after chromatography on silica gel using a gradient of heptane/ethyl acetate=100:0 to 10:90 as the eluent, the (R)-6,6-difluoro-5-(2-fluoro-5-(pyrimidin-5-yl)phenyl)-5,7,7-trimethyl-1,4-oxazepan-3-one (263 mg, 85% yield) as a white foam. MS (ISP): m/z=366.1 [M+H]+.

b) (R)-6,6-Difluoro-5-(2-fluoro-5-pyrimidin-5-yl-phenyl)-5,7,7-trimethyl-[1,4]oxazepan-3-thione A solution of (R)-6,6-difluoro-5-(2-fluoro-5-(pyrimidin-5-yl)phenyl)-5,7,7-trimethyl-1,4-oxazepan-3-one (263 mg, 720 µmol) in dioxane (24.0 ml) was treated at room temperature with Lawesson's reagent (233 mg, 576 µmol). The reaction mixture was stirred at 80° C. for 4 hours. For the workup, the reaction mixture was poured on a saturated solution of sodium hydrogencarbonate then extracted twice with ethyl acetate. The combined organic layers were washed with brine, dried over sodium sulphate, filtered and evaporated at reduced pressure to give brown oil. This residue was purified by chromatography on silica gel using a gradient of heptane/dichloromethane=100:0 to 20:80. The (R)-6,6-difluoro-5-(2-fluoro-5-(pyrimidin-5-yl)phenyl)-5,7,7-trimethyl-1,4-oxazepane-3-thione (244 mg, 89% yield) was obtained as a white foam. MS (ISP): m/z=382.1 [M+H]+.

c) (R)-6,6-Difluoro-5-(2-fluoro-5-pyrimidin-5-yl-phenyl)-5,7,7-trimethyl-2,5,6,7-tetrahydro-[1,4]oxazepin-3-ylamine A solution of (R)-6,6-difluoro-5-(2-fluoro-5-(pyrimidin-5-yl)phenyl)-5,7,7-trimethyl-1,4-oxazepane-3-thione (239 mg, 627 µmol) in methanol (7.2 ml), was treated with ammonia (7 M in methanol, 5.37 ml) and tert-butyl hydroperoxide (70% in water, 517 µl). The mixture was stirred at room temperature for 16 hours. For the workup, the reaction mixture was extracted with water and dichloromethane. The organic layer was washed with water and brine, the aqueous layers were reextracted with dichloromethane. The combined organic layers were dried over sodium sulphate, filtered and evaporated to give brown oil. The residue was purified by chromatography on an amino-silica phase using dichloromethane as the eluent. The (R)-6,6-difluoro-5-(2-fluoro-5-(pyrimidin-5-yl)phenyl)-5,7,7-trimethyl-2,5,6,7-tetrahydro-1,4-oxazepin-3-amine (94 mg, 41% yield) was obtained as a white foam. MS (ISP): m/z=365.2 [M+H]+.

Example 3

(R)-6,6-Difluoro-5,7,7-trimethyl-5-(4,3',5'-trifluoro-biphenyl-3-yl)-2,5,6,7-tetrahydro-[1,4]oxazepin-3-ylamine In a reaction sequence analogous to that described for the preparation of Example 2 the title compound was obtained as follows:

a) (R)-6,6-Difluoro-5,7,7-trimethyl-5-(4,3',5'-trifluoro-biphenyl-3-yl)-[1,4]oxazepan-3-one The reaction of (R)-5-(5-bromo-2-fluorophenyl)-6,6-difluoro-5,7,7-trimethyl-1,4-oxazepan-3-one (intermediate B6.1) (200 mg, 510 µmol) with 3,5-difluorophenyl-boronic acid (121 mg, 766 µmol) in 1,2-dimethoxyethane (3 ml), with triphenylphosphine (27.6 mg, 102 µmol) and palladium(II) acetate (11.5 mg, 51.0 µmol) as the catalyst and a solution of sodium carbonate (2M, 0.6 ml) yielded the (R)-6,6-difluoro-5,7,7-trimethyl-5-(4,3',5'-trifluoro-biphenyl-3-yl)-[1,4]oxazepan-3-one (161 mg, 79% yield) as a white solid. MS (ISP): m/z=400.1 [M+H]$^+$.

(R)-6,6-Difluoro-5,7,7-trimethyl-5-(4,3',5'-trifluoro-biphenyl-3-yl)-[1,4]oxazepan-3-thione The reaction of (R)-6,6-difluoro-5,7,7-trimethyl-5-(4,3',5'-trifluoro-biphenyl-3-yl)-[1,4]oxazepan-3-one (159 mg, 398 µmol) with Lawesson's reagent (131 mg, 319 µmol) in 1,4-dioxane (13 ml) yielded the (R)-6,6-difluoro-5,7,7-trimethyl-5-(4,3',5'-trifluoro-biphenyl-3-yl)-[1,4]oxazepan-3-thione (142 mg, 86% yield) as a white foam. MS (ISP): m/z=416.2 [M+H]$^+$.

c) (R)-6,6-Difluoro-5,7,7-trimethyl-5-(4,3',5'-trifluoro-biphenyl-3-yl)-2,5,6,7-tetrahydro-[1,4]oxazepin-3-ylamine The ammonolysis of (R)-6,6-difluoro-5,7,7-trimethyl-5-(4,3',5'-trifluoro-biphenyl-3-yl)-[1,4]oxazepan-3-thione (139.4 mg, 336 µmol) with ammonia (7M in methanol, 2.9 ml) and tert-butylhydroperoxide (70% in water, 277 µl) in methanol (4 ml) yielded the (R)-6,6-difluoro-5,7,7-trimethyl-5-(4,3',5'-trifluoro-biphenyl-3-yl)-2,5,6,7-tetrahydro-[1,4]oxazepin-3-ylamine (65 mg, 49% yield) as a white foam. MS (ISP): m/z=399.2 [M+H]$^+$.

Example 4

(R)-5-[5-(5-Chloro-pyridin-3-yl)-2-fluoro-phenyl]-6,6-difluoro-5,7,7-trimethyl-2,5,6,7-tetrahydro-[1,4]oxazepin-3-ylamine In a reaction sequence analogous to that described for the preparation of Example 2 the title compound was obtained as follows:

a) (R)-5-[5-(5-Chloro-pyridin-3-yl)-2-fluoro-phenyl]-6,6-difluoro-5,7,7-trimethyl-[1,4]oxazepan-3-one The reaction of (R)-5-(5-bromo-2-fluorophenyl)-6,6-difluoro-5,7,7-trimethyl-1,4-oxazepan-3-one (intermediate B6.1) (294 mg, 803 µmol) with 5-chloropyridin-3-ylboronic acid (139 mg, 883 µmol) in tetrahydrofuran (8 ml) and water (4 ml), with [1,1'-bis(diphenylphosphino)ferrocene]dichloropalladium(II) dichloromethane complex (32.8 mg, 32.8 µl, 40.1 µmol) as the catalyst and cesium carbonate (1.5 g, 3.21 mmol) yielded the (R)-5-[5-(5-Chloro-pyridin-3-yl)-2-fluoro-phenyl]-6,6-difluoro-5,7,7-trimethyl-[1,4]oxazepan-3-one (245 mg, 77% yield) as a white foam. MS (ISP): m/z=399.1 [M+H]$^+$ and 401.1 [M+2+H]$^+$.

b) (R)-5-[5-(5-Chloro-pyridin-3-yl)-2-fluoro-phenyl]-6,6-difluoro-5,7,7-trimethyl-[1,4]oxazepan-3-thione The reaction of (R)-5-[5-(5-chloro-pyridin-3-yl)-2-fluoro-phenyl]-6,6-difluoro-5,7,7-trimethyl-[1,4]oxazepan-3-one (235 mg, 589 µmol) with Lawesson's reagent (238 mg, 589 µmol) in 1,4-dioxane (19.6 ml) yielded the (R)-5-[5-(5-chloro-pyridin-3-yl)-2-fluoro-phenyl]-6,6-difluoro-5,7,7-trimethyl-[1,4]oxazepan-3-thione (211 mg, 86% yield) as a white solid. MS (ISP): m/z=415.1 [M+H]$^+$ and 417.1 [M+2+H]$^+$.

c) (R)-5-[5-(5-Chloro-pyridin-3-yl)-2-fluoro-phenyl]-6,6-difluoro-5,7,7-trimethyl-2,5,6,7-tetrahydro-[1,4]oxazepin-3-ylamine The ammonolysis of (R)-5-[5-(5-chloro-pyridin-3-yl)-2-fluoro-phenyl]-6,6-difluoro-5,7,7-trimethyl-[1,4]oxazepan-3-thione (211 mg, 509 µmol) with ammonia (7M in methanol, 4.4 ml) and tert-butylhydroperoxide (70% in water, 419 µl) in methanol (5 ml) yielded the (R)-5-[5-(5-Chloro-pyridin-3-yl)-2-fluoro-phenyl]-6,6-difluoro-5,7,7-trimethyl-2,5,6,7-tetrahydro-[1,4]oxazepin-3-ylamine (107 mg, 53% yield) as a white solid. MS (ISP): m/z=398.1 [M+H]$^+$ and 400.1 [M+2+H]$^+$.

Example 5

(R)-5-[5-(3,6-Dihydro-2H-pyran-4-yl)-2-fluoro-phenyl]-6,6-difluoro-5,7,7-trimethyl-2,5,6,7-tetrahydro-[1,4]oxazepin-3-ylamine In a reaction sequence analogous to that described for the preparation of Example 2 the title compound was obtained as follows:

a) (R)-5-[5-(3,6-Dihydro-2H-pyran-4-yl)-2-fluoro-phenyl]-6,6-difluoro-5,7,7-trimethyl-[1,4]oxazepan-3-one A solution of (R)-5-(5-bromo-2-fluorophenyl)-6,6-difluoro-5,7,7-trimethyl-1,4-oxazepan-3-one (intermediate B6.1) (151 mg, 412 µmol) and 4-methyl-N'-(2H-pyran-4(3H,5H,6H)-ylidene)benzenesulfonohydrazide (CAS1240042-12-9) (122 mg, 454 µmol) in dioxane (5 ml) was treated under argon with 2-dicyclohexylphosphino-2',4',6'-triisopropylbiphenyl (X-PHOS) (19.7 mg, 41.2 µmol), bis(dibenzylideneacetone) palladium (11.9 mg, 20.6 µmol) and finally lithium tert-butoxide (72.6 mg, 907 µmol). The reaction mixture was stirred in a sealed microwave tube at 110° C. for 16 hours. For the workup, the reaction mixture was poured on a saturated solution of sodium hydrogencarbonate followed by 2 extractions with ethyl acetate. The combined organic layers were washed with brine, dried over sodium sulphate, filtered and evaporated at reduced pressure to give brown oil. The residue was purified by chromatography on silica gel using a gradient of heptane/ethyl acetate=100:0 to 20:80 as the eluent. The (R)-5-(5-(3,6-dihydro-2H-pyran-4-yl)-2-fluorophenyl)-6,6-difluoro-5,7,7-trimethyl-1,4-oxazepan-3-one (76 mg, 50% yield) was obtained as an off-white foam. MS (ISP): m/z=370.2 [M+H]$^+$.

The 4-methyl-N'-(2H-pyran-4(3H,5H,6H)-ylidene)benzenesulfonohydrazide (CAS1240042-12-9) was obtained as follows:

A solution of 4-methylbenzenesulfonohydrazide (819 mg, 4.4 mmol) and dihydro-2H-pyran-4(3H)-one (487 µl, 5.28 mmol) was stirred in a Dean-Stark apparatus at 120° C. for 24 hours. The reaction mixture was cooled and evaporated at reduced pressure. The residue was purified by chromatography using a gradient of dichloromethane/ethyl acetate=100:0 to 80:20 as the eluent to give the 4-methyl-N'-(2H-pyran-4(3H,5H,6H)-ylidene)benzenesulfonohydrazide (475 mg, 40% yield) as an off white solid. MS (ISP): m/z=269.3 [M+H]$^+$.

b) (R)-5-[5-(3,6-Dihydro-2H-pyran-4-yl)-2-fluorophenyl]-6,6-difluoro-5,7,7-trimethyl-[1,4]oxazepan-3-thione The reaction of (R)-5-(5-(3,6-dihydro-2H-pyran-4-yl)-2-fluorophenyl)-6,6-difluoro-5,7,7-trimethyl-1,4-oxazepan-3-one (72 mg, 195 μmol) with Lawesson's reagent (79 mg, 195 μmol) in 1,4-dioxane (5 ml) yielded the (R)-5-(5-(3,6-dihydro-2H-pyran-4-yl)-2-fluorophenyl)-6,6-difluoro-5,7,7-trimethyl-1,4-oxazepane-3-thione (65 mg, 87% yield) as a white foam. MS (ISP): m/z=386.0 [M+H]+.

c) (R)-5-[5-(3,6-Dihydro-2H-pyran-4-yl)-2-fluorophenyl]-6,6-difluoro-5,7,7-trimethyl-2,5,6,7-tetrahydro-[1,4]oxazepin-3-ylamine The ammonolysis of (R)-5-(5-(3,6-dihydro-2H-pyran-4-yl)-2-fluorophenyl)-6,6-difluoro-5,7,7-trimethyl-1,4-oxazepane-3-thione (63 mg, 163 μmol) with ammonia (7M in methanol, 1.4 ml) and tert-butylhydroperoxide (70% in water, 135 μl) in methanol (1 ml) yielded the (R)-5-(5-(3,6-dihydro-2H-pyran-4-yl)-2-fluorophenyl)-6,6-difluoro-5,7,7-trimethyl-2,5,6,7-tetrahydro-1,4-oxazepin-3-amine (17 mg, 28% yield) as a white foam. MS (ISP): m/z=369.1 [M+H]+.

Example 6

(R)-6,6-Difluoro-5-{2-fluoro-5-[1-(4-fluoro-phenyl)-1H-pyrazol-4-yl]-phenyl}-5,7,7-trimethyl-2,5,6,7-tetrahydro-[1,4]oxazepin-3-ylamine In a reaction sequence analogous to that described for the preparation of Example 2 the title compound was obtained as follows:

a) (R)-6,6-Difluoro-5-{2-fluoro-5-[1-(4-fluoro-phenyl)-1H-pyrazol-4-yl]-phenyl}-5,7,7-trimethyl-[1,4]oxazepan-3-one The reaction of (R)-5-(5-bromo-2-fluorophenyl)-6,6-difluoro-5,7,7-trimethyl-1,4-oxazepan-3-one (intermediate B6.1) (200 mg, 510 μmol) with 1-(4-fluorophenyl)-1H-pyrazol-4-ylboronic acid (161 mg, 766 μmol) in 1,2-dimethoxyethane (4 ml), with tetrakis(triphenylphosphine)palladium(0) (29.5 mg, 25.5 μmol) as the catalyst and a solution of sodium carbonate (2M, 0.77 ml) yielded the (R)-6,6-difluoro-5-{2-fluoro-5-[1-(4-fluoro-phenyl)-1H-pyrazol-4-yl]-phenyl}-5,7,7-trimethyl-[1,4]oxazepan-3-one (202 mg, 89% yield) as a light yellow foam. MS (ISP): m/z=448.2 [M+H]+.

b) (R)-6,6-Difluoro-5-{2-fluoro-5-[1-(4-fluoro-phenyl)-1H-pyrazol-4-yl]-phenyl}-5,7,7-trimethyl-[1,4]oxazepan-3-thione The reaction of (R)-6,6-difluoro-5-{2-fluoro-5-[1-(4-fluoro-phenyl)-1H-pyrazol-4-yl]-phenyl}-5,7,7-trimethyl-[1,4]oxazepan-3-one (189 mg, 422 μmol) with Lawesson's reagent (139 mg, 338 μmol) in 1,4-dioxane (14 ml) yielded the (R)-6,6-difluoro-5-{2-fluoro-5-[1-(4-fluoro-phenyl)-1H-pyrazol-4-yl]-phenyl}-5,7,7-trimethyl-[1,4]oxazepan-3-thione (148 mg, 76% yield) as a white solid. MS (ISP): m/z=464.2.0 [M+H]+.

c) (R)-6,6-Difluoro-5-{2-fluoro-5-[1-(4-fluoro-phenyl)-1H-pyrazol-4-yl]-phenyl}-5,7,7-trimethyl-2,5,6,7-tetrahydro-[1,4]oxazepin-3-ylamine The ammonolysis of (R)-6,6-difluoro-5-{2-fluoro-5-[1-(4-fluoro-phenyl)-1H-pyrazol-4-yl]-phenyl}-5,7,7-trimethyl-[1,4]oxazepan-3-thione (144 mg, 311 μmol) with ammonia (7M in methanol, 2.7 ml) and tert-butylhydroperoxide (70% in water, 257 μl) in methanol (4 ml) yielded the (R)-6,6-Difluoro-5-{2-fluoro-5-[1-(4-fluoro-phenyl)-1H-pyrazol-4-yl]-phenyl}-5,7,7-trimethyl-2,5,6,7-tetrahydro-[1,4]oxazepin-3-ylamine (62 mg, 44% yield) as a light yellow foam. MS (ISP): m/z=447.2 [M+H]+.

Example 7

(R)-6,6-Difluoro-5-[2-fluoro-5-(2-methyl-2H-pyrazol-3-yl)-phenyl]-5,7,7-trimethyl-2,5,6,7-tetrahydro-[1,4]oxazepin-3-ylamine In a reaction sequence analogous to that described for the preparation of Example 2 the title compound was obtained as follows:

a) (R)-6,6-Difluoro-5-[2-fluoro-5-(2-methyl-2H-pyrazol-3-yl)-phenyl]-5,7,7-trimethyl-[1,4]oxazepan-3-one The reaction of (R)-5-(5-bromo-2-fluorophenyl)-6,6-difluoro-5,7,7-trimethyl-1,4-oxazepan-3-one (intermediate B6.1) (200 mg, 510 μmol) with 5-(5,5-dimethyl-1,3,2-dioxaborinan-2-yl)-1-methyl-1H-pyrazole (139 mg, 715 μmol) in dimethylformamide (9 ml) and water (0.7 ml), with [1,1'-bis(diphenylphosphino)ferrocene]dichloropalladium(II) dichloromethane complex (42.5 mg, 51.0 μmol) as the catalyst and sodium carbonate (1.38 mmol) yielded the (R)-6,6-difluoro-5-[2-fluoro-5-(2-methyl-2H-pyrazol-3-yl)-phenyl]-5,7,7-trimethyl-[1,4]oxazepan-3-one (136 mg, 73% yield) as a light yellow solid. MS (ISP): m/z=368.2 [M+H]+.

b) (R)-6,6-Difluoro-5-[2-fluoro-5-(2-methyl-2H-pyrazol-3-yl)-phenyl]-5,7,7-trimethyl-[1,4]oxazepan-3-thione The reaction of (R)-6,6-difluoro-5-[2-fluoro-5-(2-methyl-2H-pyrazol-3-yl)-phenyl]-5,7,7-trimethyl-[1,4]oxazepan-3-one (133 mg, 364 μmol) with Lawesson's reagent (120 mg, 292 μmol) in 1,4-dioxane (12 ml) yielded the (R)-6,6-difluoro-5-[2-fluoro-5-(2-methyl-2H-pyrazol-3-yl)-phenyl]-5,7,7-trimethyl-[1,4]oxazepan-3-thione (137 mg, 98% yield) as a colorless oil. MS (ISP): m/z=384.2 [M+H]+.

c) (R)-6,6-Difluoro-5-[2-fluoro-5-(2-methyl-2H-pyrazol-3-yl)-phenyl]-5,7,7-trimethyl-2,5,6,7-tetrahydro-[1,4]oxazepin-3-ylamine The ammonolysis of (R)-6,6-difluoro-5-[2-fluoro-5-(2-methyl-2H-pyrazol-3-yl)-phenyl]-5,7,7-trimethyl-[1,4]oxazepan-3-thion (133 mg, 348 μmol) with ammonia (7M in methanol, 3 ml) and tert-butylhydroperoxide (70% in water, 287 μl) in methanol (4 ml) yielded the (R)-6,6-difluoro-5-[2-fluoro-5-(2-methyl-2H-pyrazol-3-yl)-phenyl]-5,7,7-trimethyl-2,5,6,7-tetrahydro-[1,4]oxazepin-3-ylamine (20 mg, 15% yield) as a light yellow foam. MS (ISP): m/z=367.1 [M+H]+.

Example 8

(R)-6,6-Difluoro-5-[2-fluoro-5-(tetrahydro-pyran-4-yl)-phenyl]-5,7,7-trimethyl-2,5,6,7-tetrahydro-[1,4]oxazepin-3-ylamine a) (R)-6,6-Difluoro-5-[2-fluoro-5-(tetrahydro-pyran-4-yl)-phenyl]-5,7,7-trimethyl-[1,4]oxazepan-3-one A solution of (R)-5-(5-(3,6-dihydro-2H-pyran-4-yl)-2-fluorophenyl)-6,6-difluoro-5,7,7-trimethyl-1,4-oxazepan-3- one [Example 5a)] (256 mg, 693 μmol) in ethyl acetate (20 ml) was hydrogenated at room temperature for 16 hours using palladium on carbon (10%: 74 mg, 69.3 μmol) as the catalyst. The reaction mixture was filtered and evaporated to give the crude (R)-6,6-difluoro-5-(2-fluoro-5-(tetrahydro-2H-pyran-4-yl)phenyl)-5,7,7-trimethyl-1,4-oxazepan-3-one (244 mg, 95% yield) as a colorless oil. MS (ISP): m/z=372.2 [M+H]$^+$.

In a reaction sequence analogous to that described for the preparation of Example 2 the title compound was obtained as follows:

b) (R)-6,6-Difluoro-5-(2-fluoro-5-(tetrahydro-2H-pyran-4-yl)phenyl)-5,7,7-trimethyl-1,4-oxazepan-3-thione The reaction of (R)-6,6-difluoro-5-(2-fluoro-5-(tetrahydro-2H-pyran-4-yl)phenyl)-5,7,7-trimethyl-1,4-oxazepan-3-one (244 mg, 657 μmol) with Lawesson's reagent (266 mg, 657 μmol) in 1,4-dioxane (20 ml) yielded the (R)-6,6-difluoro-5-(2-fluoro-5-(tetrahydro-2H-pyran-4-yl)phenyl)-5,7,7-trimethyl-1,4-oxazepan-3-thione (205 mg, 81% yield) as a white foam. MS (ISP): m/z=388.2 [M+H]$^+$.

c) (R)-6,6-Difluoro-5-[2-fluoro-5-(tetrahydro-pyran-4-yl)-phenyl]-5,7,7-trimethyl-2,5,6,7-tetrahydro-[1,4]oxazepin-3-ylamine The ammonolysis of (R)-6,6-difluoro-5-(2-fluoro-5-(tetrahydro-2H-pyran-4-yl)phenyl)-5,7,7-trimethyl-1,4-oxazepan-3-thione (203 mg, 524 μmol) with ammonia (7M in methanol, 4.4 ml) and tert-butylhydroperoxide (70% in water, 360 μl) in methanol (3 ml) yielded the (R)-6,6-difluoro-5-[2-fluoro-5-(tetrahydro-pyran-4-yl)-phenyl]-5,7,7-trimethyl-2,5,6,7-tetrahydro-[1,4]oxazepin-3-ylamine (76 mg, 39% yield) as a white foam. MS (ISP): m/z=371.1 [M+H]$^+$.

Example 9

(R)-5-[5-(3-Chloro-phenylethynyl)-2-fluoro-phenyl]-6,6-difluoro-5,7,7-trimethyl-2,5,6,7-tetrahydro-[1,4]oxazepin-3-ylamine a) (R)-5-[5-(3-Chloro-phenylethynyl)-2-fluoro-phenyl]-6,6-difluoro-5,7,7-trimethyl-[1,4]oxazepan-3-one A dried pressure tube was charged with (R)-5-(5-bromo-2-fluorophenyl)-6,6-difluoro-5,7,7-trimethyl-1,4-oxazepan-3-one (intermediate B6.1) (250 mg, 622 μmol) and dimethylformamide (2 ml). The solution was flushed with argon, thereafter, successively bis(triphenylphosphin)palladium(II) chloride (31.2 mg, 43.5 μmol), triphenylphoshine (3.26 mg, 12.4 μmol), triethylamine (126 mg, 1.24 mmol), 1-chloro-3-ethynylbenzene (175 mg, 1.24 mmol), and copper(i) iodide (3.6 mg, 18.7 μmol) were added. The tube was sealed and the reaction mixture stirred at room temperature for 10 minutes, then it was heated at 60° C. for 16 hours. For the workup, the reaction mixture was cooled and evaporated at reduced pressure. The residue was directly purified by chromatography on an amine-silica phase using a gradient of heptane/ethyl acetate=100:0 to 60:10 as the eluent. The (R)-5-[5-(3-chloro-phenylethynyl)-2-fluoro-phenyl]-6,6-difluoro-5,7,7-trimethyl-[1,4]oxazepan-3-one (235 mg, 90% yield) was obtained as a green foam. MS (ISP): m/z=422.1 [M+2+H]$^+$ and 424.2 [M+H]$^+$.

In a reaction sequence analogous to that described for the preparation of Example 2 the title compound was obtained as follows:

b) (R)-5-[5-(3-Chloro-phenylethynyl)-2-fluoro-phenyl]-6,6-difluoro-5,7,7-trimethyl-[1,4]oxazepan-3-thione The reaction of (R)-5-[5-(3-chloro-phenylethynyl)-2-fluoro-phenyl]-6,6-difluoro-5,7,7-trimethyl-[1,4]oxazepan-3-one (233 mg, 552 μmol) with Lawesson's reagent (230 mg, 552 μmol) in 1,4-dioxane (15 ml) yielded the (R)-5-[5-(3-chloro-phenylethynyl)-2-fluoro-phenyl]-6,6-difluoro-5,7,7-trimethyl-[1,4]oxazepan-3-thione (129 mg, 53% yield) as a light yellow foam. MS (ISP): m/z=438.1 [M+H]$^+$ and 440.2 [M+2+H]$^+$.

c) (R)-5-[5-(3-Chloro-phenylethynyl)-2-fluoro-phenyl]-6,6-difluoro-5,7,7-trimethyl-2,5,6,7-tetrahydro-[1,4]oxazepin-3-ylamine The ammonolysis of (R)-5-[5-(3-chloro-phenylethynyl)-2-fluoro-phenyl]-6,6-difluoro-5,7,7-trimethyl-[1,4]oxazepan-3-thione (126 mg, 289 μmol) with ammonia (7M in methanol, 2.5 ml) and tert-butylhydroperoxide (70% in water, 238 μl) in methanol (3 ml) yielded the (R)-5-[5-(3-chloro-phenyl ethynyl)-2-fluoro-phenyl]-6,6-difluoro-5,7,7-trimethyl-2,5,6,7-tetrahydro-[1,4]oxazepin-3-ylamine (52 mg, 43% yield) as a white foam. MS (ISP): m/z=421.1 [M+H]$^+$ and 423.1 [M+2+H]$^+$.

Example 10

(R)-5-(3',5'-Dichloro-4-fluoro-biphenyl-3-yl)-6,6-difluoro-5,7,7-trimethyl-2,5,6,7-tetrahydro-[1,4]oxazepin-3-ylamine In a reaction sequence analogous to that described for the preparation of Example 2 the title compound was obtained as follows:

a) (R)-5-(3',5'-Dichloro-4-fluoro-biphenyl-3-yl)-6,6-difluoro-5,7,7-trimethyl-[1,4]oxazepan-3-one The reaction of (R)-5-(5-bromo-2-fluorophenyl)-6,6-difluoro-5,7,7-trimethyl-1,4-oxazepan-3-one (intermediate B6.1) (255 mg, 696 μmol) with 3,5-dichlorophenylboronic acid (146 mg, 766 μmol) in tetrahydrofuran (8 ml) and water (4 ml), with [1,1'-bis(diphenylphosphino)ferrocene]dichloropalladium(II) dichloromethane complex (28.4 mg, 34.8 μmol) as the catalyst and cesium carbonate (908 mg, 2.79 mmol) yielded the (R)-5-(3',5'-dichloro-4-fluoro-biphenyl-3-yl)-6,6-difluoro-5,7,7-trimethyl-[1,4]oxazepan-3-one (255 mg, 85% yield) as a white solid.

b) (R)-5-(3',5'-Dichloro-4-fluoro-biphenyl-3-yl)-6,6-difluoro-5,7,7-trimethyl-[1,4]oxazepan-3-thione The reaction of (R)-5-(3',5'-dichloro-4-fluoro-biphenyl-3-yl)-6,6-difluoro-5,7,7-trimethyl-[1,4]oxazepan-3-one (250 mg, 578 μmol) with Lawesson's reagent (187 mg, 463 μmol) in 1,4-dioxane (19 ml) yielded the (R)-5-(3',5'-dichloro-4-fluoro-biphenyl-3-yl)-6,6-difluoro-5,7,7-trimethyl-[1,4]oxazepan-3-thione (202 mg, 78% yield) as a white foam. MS (ISN): m/z=446.0 [M−H]$^-$ and 447.9 [M+2-H]$^-$.

c) (R)-5-(3',5'-Dichloro-4-fluoro-biphenyl-3-yl)-6,6-difluoro-5,7,7-trimethyl-2,5,6,7-tetrahydro-[1,4]oxazepin-3-ylamine The ammonolysis of (R)-5-(3',5'-dichloro-4-fluoro-biphenyl-3-yl)-6,6-difluoro-5,7,7-trimethyl-[1,4]oxazepan-3-thione (195 mg, 435 µmol) with ammonia (7M in methanol, 3.7 ml) and tert-butylhydroperoxide (70% in water, 359 µl) in methanol (5 ml) yielded the (R)-5-(3',5'-dichloro-4-fluoro-biphenyl-3-yl)-6,6-difluoro-5,7,7-trimethyl-2,5,6,7-tetrahydro-[1,4]oxazepin-3-ylamine (105 mg, 56% yield) as a white foam. MS (ISP): m/z=431.2 [M+H]$^+$ and 433.3 [M+2+H]$^+$.

Example 11

(R)-5-(5'-Chloro-4,3'-difluoro-biphenyl-3-yl)-6,6-difluoro-5,7,7-trimethyl-2,5,6,7-tetrahydro-[1,4]oxazepin-3-ylamine hydrochloride In a reaction sequence analogous to that described for the preparation of Example 2 the title compound was obtained as follows:

a) (R)-5-(5'-Chloro-4,3'-difluoro-biphenyl-3-yl)-6,6-difluoro-5,7,7-trimethyl-[1,4]oxazepan-3-one The reaction of (R)-5-[5-(5,5-dimethyl-[1,3,2]dioxaborinan-2-yl)-2-fluoro-phenyl]-6,6-difluoro-5,7,7-trimethyl-[1,4]oxazepan-3-one (intermediate D6.2) (180 mg, 452 µmol) with 1-bromo-3-chloro-5-fluorobenzene (125 mg, 73.0 µl, 587 µmol) in tetrahydrofuran (10 ml) and water (4 ml), with [1,1'-bis(diphenylphosphino)ferrocene]dichloropalladium(II) dichloromethane complex (18.8 mg, 22.6 µmol) as the catalyst and cesium carbonate (589 mg, 1.81 mmol) yielded the (R)-5-(5'-chloro-4,3'-difluoro-biphenyl-3-yl)-6,6-difluoro-5,7,7-trimethyl-[1,4]oxazepan-3-one (133 mg, 71%) as light yellow crystals. MS (ISP): m/z=416.2 [M+H]$^+$ and 418.2 [M+2+H]$^+$.

b) (R)-5-(5'-Chloro-4,3'-difluoro-biphenyl-3-yl)-6,6-difluoro-5,7,7-trimethyl-[1,4]oxazepan-3-thione The reaction of (R)-5-(5'-chloro-4,3'-difluoro-biphenyl-3-yl)-6,6-difluoro-5,7,7-trimethyl-[1,4]oxazepan-3-one (130 mg, 313 µmol) with Lawesson's reagent (130 mg, 313 µmol) in 1,4-dioxane (5 ml) yielded the (R)-5-(5'-chloro-4,3'-difluoro-biphenyl-3-yl)-6,6-difluoro-5,7,7-trimethyl-[1,4]oxazepan-3-thione (131 mg, 97%) as a white foam. MS (ISP): m/z=432.2 [M+H]$^+$ and 434.2 [M+2+H]$^+$.

c) (R)-5-(5'-Chloro-4,3'-difluoro-biphenyl-3-yl)-6,6-difluoro-5,7,7-trimethyl-2,5,6,7-tetrahydro-[1,4]oxazepin-3-ylamine hydrochloride The ammonolysis of (R)-5-(5'-chloro-4,3'-difluoro-biphenyl-3-yl)-6,6-difluoro-5,7,7-trimethyl-[1,4]oxazepan-3-thione (128 mg, 296 µmol) with ammonia (7M in methanol, 2.5 ml) and tert-butylhydroperoxide (70% in water, 244 µl) in methanol (4 ml) yielded the (R)-5-(5'-chloro-4,3'-difluoro-biphenyl-3-yl)-6,6-difluoro-5,7,7-trimethyl-2,5,6,7-tetrahydro-[1,4]oxazepin-3-ylamine as a white foam. The amine was treated with hydrochloric acid (4M in dioxane; 1 ml). The solution was evaporated at reduced pressure and the residue triturated with diethyl ether. After filtration the (R)-5-(5'-chloro-4,3'-difluoro-biphenyl-3-yl)-6,6-difluoro-5,7,7-trimethyl-2,5,6,7-tetrahydro-[1,4]oxazepin-3-ylamine hydrochloride (46 mg, 34% yield) was obtained as a white foam. MS (ISP): m/z=415.2 [M+H]$^+$ and 417.2 [M+2+H]$^+$.

Example 12

3'-((R)-3-Amino-6,6-difluoro-5,7,7-trimethyl-2,5,6,7-tetrahydro-[1,4]oxazepin-5-yl)-4'-fluoro-biphenyl-3-sulfonic acid 2,2-dimethyl-propyl ester In a reaction sequence analogous to that described for the preparation of Example 2 the title compound was obtained as follows:

a) 3'-((R)-6,6-Difluoro-5,7,7-trimethyl-3-oxo-[1,4]oxazepan-5-yl)-4'-fluoro-biphenyl-3-sulfonic acid 2,2-dimethyl-propyl ester The reaction of (R)-5-(5-bromo-2-fluorophenyl)-6,6-difluoro-5,7,7-trimethyl-1,4-oxazepan-3-one (intermediate B6.1) (200 mg, 546 µmol) with 3-(neopentyloxysulfonyl)phenylboronic acid (CAS 951233-64-0) (178 mg, 655 µmol) in tetrahydrofuran (10 ml) and water (5 ml), with [1,1'-bis(diphenylphosphino)ferrocene]dichloropalladium(II) dichloromethane complex (22.3 mg, 27.3 µmol) as the catalyst and cesium carbonate (712 mg, 2.18 mmol), yielded the 3'-((R)-6,6-difluoro-5,7,7-trimethyl-3-oxo-[1,4]oxazepan-5-yl)-4'-fluoro-biphenyl-3-sulfonic acid 2,2-dimethyl-propyl ester (229 mg, 82% yield) as a white foam. MS (ISP): m/z=514.5 [M+H]$^+$ and 531.2 [M+NH$_3$]$^+$.

b) 3'-((R)-6,6-Difluoro-5,7,7-trimethyl-3-thioxo-[1,4]oxazepan-5-yl)-4'-fluoro-biphenyl-3-sulfonic acid 2,2-dimethyl-propyl ester The reaction of 3'-((R)-6,6-difluoro-5,7,7-trimethyl-3-oxo-[1,4]oxazepan-5-yl)-4'-fluoro-biphenyl-3-sulfonic acid 2,2-dimethyl-propyl ester (124 mg, 241 µmol with Lawesson's reagent (97.7 mg, 241 µmol) in 1,4-dioxane (10 ml) yielded the 3'-((R)-6,6-difluoro-5,7,7-trimethyl-3-thioxo-[1,4]oxazepan-5-yl)-4'-fluoro-biphenyl-3-sulfonic acid 2,2-dimethyl-propyl ester (115 mg, 90%) as a white foam. MS (ISP): m/z=530.2 [M+H]$^+$.

c) 3'-((R)-3-Amino-6,6-difluoro-5,7,7-trimethyl-2,5,6,7-tetrahydro-[1,4]oxazepin-5-yl)-4'-fluoro-biphenyl-3-sulfonic acid 2,2-dimethyl-propyl ester The ammonolysis of 3'-((R)-6,6-difluoro-5,7,7-trimethyl-3-thioxo-[1,4]oxazepan-5-yl)-4'-fluoro-biphenyl-3-sulfonic acid 2,2-dimethyl-propyl ester (115 mg, 217 µmol) with ammonia (7M in methanol, 2 ml) and tert-butylhydroperoxide (70% in water, 180 µl) in methanol (3 ml) yielded the 3'-((R)-3-amino-6,6-difluoro-5,7,7-trimethyl-2,5,6,7-tetrahydro-[1,4]oxazepin-5-yl)-4'-fluoro-biphenyl-3-sulfonic acid 2,2-dimethyl-propyl ester (41 mg, 37%) as a white foam. MS (ISP): m/z=513.5 [M+H]$^+$.

Example 13

3'-((R)-3-Amino-6,6-difluoro-5,7,7-trimethyl-2,5,6,7-tetrahydro-[1,4]oxazepin-5-yl)-2,4'-difluoro-biphenyl-4-carbonitrile In a manner analogous to that described for the preparation of Example 1 (method A), the reaction of (R)-5-(5-bromo-2-fluoro-phenyl)-6,6-difluoro-5,7,7-trimethyl-2,5,6,7-tetrahydro-[1,4]oxazepin-3-ylamine (intermediate B 8.1) (100 mg, 274 µmol) with 5-cyano-2-fluorophenylboronic acid (CAS 468718-30-1) (54.2 mg, 329 µmol) in tetrahydrofuran (8 ml) and water (4 ml), with [1,1'-bis(diphenylphosphino)ferrocene]dichloropalladium(II) dichloromethane complex (11.2 mg, 13.7 µmol) as the catalyst and cesium carbonate (357 mg, 1.1 mmol), yielded the 3'-((R)-3-amino-6,6-difluoro-5,7,7-trimethyl-2,5,6,7-tetrahydro-[1,4]oxazepin-5-yl)-2',4'-difluoro-biphenyl-4-carbonitrile (42 mg, 38% yield) as a white foam. MS (ISP): m/z=406.4 [M+H]$^+$.

Example 14

3'-((R)-3-Amino-6,6-difluoro-5,7,7-trimethyl-2,5,6,7-tetrahydro-[1,4]oxazepin-5-yl)-4'-fluoro-biphenyl-3-carbonitrile In a manner analogous to that described for the preparation of Example 1 (method A), the reaction of (R)-5-(5-bromo-2-fluoro-phenyl)-6,6-difluoro-5,7,7-trimethyl-2,5,6,7-tetrahydro-[1,4]oxazepin-3-ylamine (intermediate B8.1) (100 mg, 274 µmol) with 3-cyano-phenylboronic acid (48.3 mg, 329 µmol) in tetrahydrofuran (8 ml) and water (4 ml), with [1,1'-bis(diphenylphosphino)ferrocene]dichloropalladium(II) dichloromethane complex (11.2 mg, 13.7 µmol) as the catalyst and cesium carbonate (357 mg, 1.1 mmol), yielded the 3'-((R)-3-amino-6,6-difluoro-5,7,7-trimethyl-2,5,6,7-tetrahydro-[1,4]oxazepin-5-yl)-4'-fluoro-biphenyl-3-carbonitrile (55 mg, 52% yield) as a beige foam. MS (ISP): m/z=388.3 [M+H]$^+$.

Example 15

3'-((R)-3-Amino-6,6-difluoro-5,7,7-trimethyl-2,5,6,7-tetrahydro-[1,4]oxazepin-5-yl)-4'-fluoro-biphenyl-3-sulfonic acid tert-butylamide In a manner analogous to that described for the preparation of Example 1 (method A), the reaction of (R)-5-(5-bromo-2-fluoro-phenyl)-6,6-difluoro-5,7,7-trimethyl-2,5,6,7-tetrahydro-[1,4]oxazepin-3-ylamine (intermediate B8.1) (100 mg, 274 µmol) with 3-(N-tert-butylsulfamoyl)phenylboronic acid (84.5 mg, 329 µmol) in tetrahydrofuran (10 ml) and water (5 ml), with [1 µl'-bis(diphenylphosphino)ferrocene]dichloropalladium(II) dichloromethane complex (26.5 mg, 32.5 µmol) as the catalyst and cesium carbonate (357 mg, 1.1 mmol), yielded the 3'-((R)-3-amino-6,6-difluoro-5,7,7-trimethyl-2,5,6,7-tetrahydro-[1,4]oxazepin-5-yl)-4'-fluoro-biphenyl-3-sulfonic acid tert-butylamide (105 mg, 77% yield) as a light yellow foam. MS (ISP): m/z=498.4 [M+H]$^+$.

Example 16

5-[3-((R)-3-Amino-6,6-difluoro-5,7,7-trimethyl-2,5,6,7-tetrahydro-[1,4]oxazepin-5-yl)-4-fluoro-phenyl]-pyridine-3-sulfonic acid tert-butylamide In a manner analogous to that described for the preparation of Example 1 (method A), the reaction of (R)-5-(5-bromo-2-fluoro-phenyl)-6,6-difluoro-5,7,7-trimethyl-2,5,6,7-tetrahydro-[1,4]oxazepin-3-ylamine (intermediate B8.1) (115 mg, 315 µmol) with 5-(N-tert-butylsulfamoyl)pyridin-3-ylboronic acid (97.5 mg, 378 µmol) in tetrahydrofuran (8 ml) and water (4 ml), with [1,1'-bis(diphenylphosphino)ferrocene] dichloromethane complex (24 mg, 29.4 µmol) as the catalyst and cesium carbonate (410 mg, 1.26 mmol), yielded the 5-[3-((R)-3-amino-6,6-difluoro-5,7,7-trimethyl-2,5,6,7-tetrahydro-[1,4]oxazepin-5-yl)-4-fluoro-phenyl]-pyridine-3-sulfonic acid tert-butylamide (95 mg, 61% yield) as an off-white foam. MS (ISP): m/z=499.3 [M+H]$^+$.

The 5-(N-tert-butylsulfamoyl)pyridin-3-ylboronic acid was obtained in the following manner:

A solution of 5-bromo-pyridine-3-sulfonic acid tert-butylamide (CAS 911111-80-3; WO2010007) (11.4 g, 39 mmol) in tetrahydrofuran (200 ml) was treated with triisopropyl borate (33 ml, 144 mmol) and cooled to −78° C. A solution of n-butyl lithium in hexane (1.6M, 90 ml, 144 mmol) was added cautiously whereby the reaction temperature was kept below −60° C. The reaction mixture was stirred for 3.5 hours at −78° C. For the workup, the reaction mixture was treated with water (300 ml), stirred at room temperature for 15 minutes, and then extracted with ethyl acetate. The aqueous layer was separated and acidified with hydrochloric acid (3M) to pH 4. Thereafter, solid sodium chloride was added, and the aqueous layer was extracted with ethyl acetate. The organic layers were combined, dried over magnesium sulphate, filtered, and the solvent evaporated to give a light yellow amorphous product. For purification, the residue was dissolved at room temperature in a 3:1-mixture of water and isopropanol (100 ml). More water was added (total volume: 200 ml), then the solution cooled to 0° C., stirred for 30 minutes. The precipitate was filtered, the solid washed with water and dried at high vacuum to give the 5-(N-tert-butylsulfamoyl)pyridin-3-ylboronic acid (5.06 g, 50% yield) as an off-white solid. MS (ISN): m/z=257.1 [M−H]$^-$.

Example 17

(R)-6,6-Difluoro-5-[2-fluoro-5-(2-methyl-thiazol-4-ylethynyl)-phenyl]-5,7,7-trimethyl-2,5,6,7-tetrahydro-[1,4]oxazepin-3-ylamine a) (R)-6,6-Difluoro-5-[2-fluoro-5-(2-methyl-thiazol-4-ylethynyl)-phenyl]-5,7,7-trimethyl-[1,4]oxazepan-3-one A dried pressure tube was charged with (R)-6,6-difluoro-5-(2-fluoro-5-iodo-phenyl)-5,7,7-trimethyl-[1,4]oxazepan-3-one (intermediate B6".1) (203 mg, 491 µmol), 2-methyl-4-((trimethylsilyl)ethynyl)thiazole (115 mg, 590 µmol), and N,N-dimethylformamide (3 ml) flushed with nitrogen (solution 1). Another dried pressure tube was flushed with argon, thereafter, successively N,N-dimethylformamide (3 ml), bis(triphenylphosphine) palladium(II)chloride (24.6 mg, 34.4 µmol), triphenylphoshine (5.2 mg, 19.7 µmol), copper(I)iodide (1.9 mg, 9.8 µmol), triethylamine (249 mg, 2.46 mmol), and tetrabutylammoniumiodide (185 mg, 491 µmol) were added. The mixture was heated to 40° C., and solution 1 was added dropwise. The temperature was raised to 60° C. and stirring was continued for 16 hours. For the workup, the reaction mixture was evaporated at reduced pressure and the residue directly purified by chromatography on silica gel using a gradient of heptane/ethyl acetate=100:0 to 50:50 as the eluent. The (R)-6,6-difluoro-5-[2-fluoro-5-(2-methyl-thiazol-4-ylethynyl)-phenyl]-5,7,7-trimethyl-[1,4]oxazepan-3-one (182 mg, 91% yield) was obtained as a white foam. MS (ISP): m/z=409.3 [M+H]$^+$.

In a reaction sequence analogous to that described for the preparation of Example 2 the title compound was obtained as follows:

b) (R)-6,6-difluoro-5-[2-fluoro-5-(2-methyl-thiazol-4-ylethynyl)-phenyl]-5,7,7-trimethyl-[1,4]oxazepan-3-thione The reaction of (R)-6,6-difluoro-5-[2-fluoro-5-(2-methyl-thiazol-4-ylethynyl)-phenyl]-5,7,7-trimethyl-[1,4]oxazepan-3-one (178 mg, 436 μmol) with Lawesson's reagent (182 mg, 436 μmol) in 1,4-dioxane (8 ml) yielded the (R)-6,6-difluoro-5-[2-fluoro-5-(2-methyl-thiazol-4-ylethynyl)-phenyl]-5,7,7-trimethyl-[1,4]oxazepan-3-thione (175 mg, 94% yield) as a light yellow foam. MS (ISP): m/z=425.1 [M+H]$^+$ and 427.1 [M+2+H]$^+$.

c) (R)-6,6-Difluoro-5-[2-fluoro-5-(2-methyl-thiazol-4-ylethynyl)-phenyl]-5,7,7-trimethyl-2,5,6,7-tetrahydro-[1,4]oxazepin-3-ylamine The ammonolysis of (R)-6,6-difluoro-5-[2-fluoro-5-(2-methyl-thiazol-4-ylethynyl)-phenyl]-5,7,7-trimethyl-[1,4]oxazepan-3-thione (168 mg, 395 μmol) with ammonia (7M in methanol, 3.4 ml) and tert-butylhydroperoxide (70% in water, 326 μl) in methanol (5 ml) yielded the (R)-6,6-difluoro-5-[2-fluoro-5-(2-methyl-thiazol-4-ylethynyl)-phenyl]-5,7,7-trimethyl-2,5,6,7-tetrahydro-[1,4]oxazepin-3-ylamine (62 mg, 39% yield) as a white foam. MS (ISP): m/z=408.3 [M+H]$^+$ and 410.3 [M+2+H]$^+$.

Example 18

Method C

(R)-5-{5-[1-(3-Chloro-phenyl)-1H-pyrazol-4-yl]-2-fluoro-phenyl}-6,6-difluoro-5,7,7-trimethyl-2,5,6,7-tetrahydro-[1,4]oxazepin-3-ylamine hydrochloride a) [Bis-(4-methoxy-phenyl)-phenyl-methyl]-((R)-5-{5-[1-(3-chloro-phenyl)-1H-pyrazol-4-yl]-2-fluoro-phenyl}-6,6-difluoro-5,7,7-trimethyl-2,5,6,7-tetrahydro-[1,4]oxazepin-3-yl)-amine A dried pressure tube was consecutively charged with (R)—N-(bis(4-methoxyphenyl)(phenyl)methyl)-5-(5-bromo-2-fluorophenyl)-6,6-difluoro-5,7,7-trimethyl-2,5,6,7-tetrahydro-1,4-oxazepin-3-amine (intermediate B9.1) (199 mg, 299 μmol), 1,2-dimethoxyethane (4 ml), 1-(3-chlorophenyl)-1H-pyrazol-4-ylboronic acid (CAS 1072945-88-0) (102 mg, 448 μmol), and a solution of potassium carbonate (2M, 448·1). The tube was flushed with argon, thereafter tetrakistriphenylphosphinepalladium(0) (17.3 mg, 14.9 μmol) was added, the tube was sealed and the reaction mixture heated at 85° C. for 16 hours. For the workup, the reaction mixture was evaporated at reduced pressure and the residue directly purified by chromatography on an amine-silica phase using a gradient of heptane/ethyl acetate=100:0 to 80:20 as the eluent. The [bis-(4-methoxy-phenyl)-phenyl-methyl]-((R)-5-{5-[1-(3-chloro-phenyl)-1H-pyrazol-4-yl]-2-fluoro-phenyl}-6,6-difluoro-5,7,7-trimethyl-2,5,6,7-tetrahydro-[1,4]oxazepin-3-yl)-amine (177 mg, 77% yield) was obtained as a white foam. MS (ISP): m/z=765.4 [M+H]$^+$ and 767.4 [M+2+H]$^+$.

b) (R)-5-{5-[1-(3-Chloro-phenyl)-1H-pyrazol-4-yl]-2-fluoro-phenyl}-6,6-difluoro-5,7,7-trimethyl-2,5,6,7-tetrahydro-[1,4]oxazepin-3-ylamine hydrochloride A solution of [bis-(4-methoxy-phenyl)-phenyl-methyl]-((R)-5-{5-[1-(3-chloro-phenyl)-1H-pyrazol-4-yl]-2-fluoro-phenyl}-6,6-difluoro-5,7,7-trimethyl-2,5,6,7-tetrahydro-[1,4]oxazepin-3-yl)-amine (174 mg, 228 μmol) in dichloromethane (4 ml) was treated at room temperature with trifluoro acetic acid (178·1, 2.28 mmol). The reaction mixture was stirred at room temperature for 16 hours. For the workup, the reaction mixture was evaporated at reduced pressure and the dark red residue was directly purified by chromatography on an amine-silica phase using a gradient of heptane/ethyl acetate=100:0 to 30:60 as the eluent. For further purification, the product (146 mg) was treated with a solution of hydrochloric acid in dioxane (4M, 1 ml). After evaporation at reduced pressure, the residue was triturated with diethyl ether (2 ml). The solid residue was dried at high vacuum an yielded the (R)-5-{5-[1-(3-chloro-phenyl)-1H-pyrazol-4-yl]-2-fluoro-phenyl}-6,6-difluoro-5,7,7-trimethyl-2,5,6,7-tetrahydro-[1,4]oxazepin-3-ylamine hydrochloride (76 mg, 67% yield) as a white solid. MS (ISP): m/z=463.2 [M+H]$^+$ and 465.2 [M+2+H]$^+$.

Example 19

(R)-5-[5-(6-Chloro-benzooxazol-2-yl)-2-fluoro-phenyl]-6,6-difluoro-5,7,7-trimethyl-2,5,6,7-tetrahydro-[1,4]oxazepin-3-ylamine hydrochloride a) [Bis-(4-methoxy-phenyl)-phenyl-methyl]-{(R)-5-[5-(6-chloro-benzooxazol-2-yl)-2-fluoro-phenyl]-6,6-difluoro-5,7,7-trimethyl-2,5,6,7-tetrahydro-[1,4]oxazepin-3-yl}-amine A dried pressure tube was consecutively charged with [bis-(4-methoxy-phenyl)-phenyl-methyl]-{(R)-5-[5-(5,5-dimethyl-[1,3,2]dioxaborinan-2-yl)-2-fluoro-phenyl]-6,6-difluoro-5,7,7-trimethyl-2,5,6,7-tetrahydro-[1,4]oxazepin-3-yl}-amine (intermediate B10.1) (100 mg, 127 μmol), tetrahydrofuran (3 ml), 2,6-dichlorobenzo[d]oxazole (31.6 mg, 165 μmol), cesium carbonate (165 mg, 507 μmol) and water (1.5 ml). The tube was flushed with argon, thereafter [1,1'-bis(diphenylphosphino)ferrocene]dichloropalladium (II) dichloromethane complex (11 mg, 12.7 μmol) was added, the tube was sealed and the reaction mixture heated at 85° C. for 64 hours. For the workup, the reaction mixture was evaporated at reduced pressure and the residue directly purified by chromatography on silica gel using a gradient of heptane/ethyl acetate=100:0 to 80:20 as the eluent. The [bis-(4-methoxy-phenyl)-phenyl-methyl]-{(R)-5-[5-(6-chloro-benzo oxazol-2-yl)-2-fluoro-phenyl]-6,6-difluoro-5,7,7-trimethyl-2,5,6,7-tetrahydro-[1,4]oxazepin-3-yl}-amine (41 mg, 44% yield) was obtained as a white solid. MS (ISP): m/z=740.4 [M+H]$^+$ and 742.3 [M+2+H]$^+$.

b) (R)-5-[5-(6-Chloro-benzooxazol-2-yl)-2-fluoro-phenyl]-6,6-difluoro-5,7,7-trimethyl-2,5,6,7-tetrahydro-[1,4]oxazepin-3-ylamine hydrochloride In a manner analogous to that described in Example 18b), the treatment of [bis-(4-methoxy-phenyl)-phenyl-methyl]-{(R)-5-[5-(6-chloro-benzo oxazol-2-yl)-2-fluoro-phenyl]-6,6-difluoro-5,7,7-trimethyl-2,5,6,7-tetrahydro-[1,4]oxazepin-3-yl}-amine (38 mg, 51.3 μmol) with trifluoro acetic acid (40 μl, 513 μmol), treatment with hydrochloric acid and followed by trituration with diethyl ether yielded the (R)-5-[5-(6-chloro-benzooxazol-2-yl)-2-fluoro-phenyl]-6,6-difluoro-5,7,7-trimethyl-2,5,6,7-tetrahydro-[1,4]oxazepin-3-ylamine hydrochloride (16 mg, 66% yield) as an off-white solid. MS (ISP): m/z=438.2 [M+H]$^+$ and 440.3 [M+2+H]$^+$.

Example 20

3'-((R)-3-Amino-6,6-difluoro-5,7,7-trimethyl-2,5,6, 7-tetrahydro-[1,4]oxazepin-5-yl)-4'-fluoro-biphenyl-4-carbonitrile In a reaction sequence analogous to that described for the preparation of Example 19 the title compound was obtained as follows:

a) 3'-((R)-3-{[Bis-(4-methoxy-phenyl)-phenyl-methyl]-amino}-6,6-difluoro-5,7,7-trimethyl-2,5,6,7-tetrahydro-[1,4]oxazepin-5-yl)-4'-fluoro-biphenyl-4-carbonitrile Reaction of [bis-(4-methoxy-phenyl)-phenyl-methyl]-{(R)-5-[5-(5,5-dimethyl-[1,3,2]dioxaborinan-2-yl)-2-fluoro-phenyl]-6,6-difluoro-5,7,7-trimethyl-2,5,6,7-tetrahydro-[1,4]oxazepin-3-yl}-amine (intermediate B10.1) (199 mg, 254 μmol) with 4-bromobenzonitrile (61.3 mg, 330 μmol) yielded the 3'-((R)-3-{[bis-(4-methoxy-phenyl)-phenyl-methyl]-amino}-6,6-difluoro-5,7,7-trimethyl-2,5,6,7-tetrahydro-[1,4]oxazepin-5-yl)-4'-fluoro-biphenyl-4-carbonitrile (137 mg, 78% yield) as a white foam. MS (ISP): m/z=690.4 [M+H]$^+$.

b) 3'-((R)-3-Amino-6,6-difluoro-5,7,7-trimethyl-2,5, 6,7-tetrahydro-[1,4]oxazepin-5-yl)-4'-fluoro-biphenyl-4-carbonitrile Deprotection of 3'-((R)-3-{[bis-(4-methoxy-phenyl)-phenyl-methyl]-amino}-6,6-difluoro-5,7,7-trimethyl-2,5,6,7-tetrahydro-[1,4]oxazepin-5-yl)-4'-fluoro-biphenyl-4-carbonitrile (126 mg, 183 μmol) with trifluoro acetic acid (143 μl, 1.83 mmol) and chromatography on an amine-silica phase yielded the 3'-((R)-3-amino-6,6-difluoro-5,7,7-trimethyl-2,5,6,7-tetrahydro-[1,4]oxazepin-5-yl)-4'-fluoro-biphenyl-4-carbonitrile (63 mg, 90% yield) as a white foam. MS (ISP): m/z=388.2 [M+H]$^+$.

Example 21

(R)-5-[5-(6-Chloro-benzothiazol-2-yl)-2-fluoro-phenyl]-6,6-difluoro-5,7,7-trimethyl-2,5,6,7-tetrahydro-[1,4]oxazepin-3-ylamine hydrochloride In a reaction sequence analogous to that described for the preparation of Example 19 the title compound was obtained as follows:

a) [Bis-(4-methoxy-phenyl)-phenyl-methyl]-{(R)-5-[5-(6-chloro-benzothiazol-2-yl)-2-fluoro-phenyl]-6, 6-difluoro-5,7,7-trimethyl-2,5,6,7-tetrahydro-[1,4]oxazepin-3-yl}-amine Reaction of [bis-(4-methoxy-phenyl)-phenyl-methyl]-{(R)-6,6-difluoro-5-[2-fluoro-5-(4,4,5,5-tetramethyl-[1,3,2]dioxaborolan-2-yl)-phenyl]-5,7,7-trimethyl-2,5,6,7-tetrahydro-[1,4]oxazepin-3-yl}-amine (intermediate B10.2) (35 mg, 49 μmol) with 2,6-dichlorobenzo[d]thiazole (13.4 mg, 63.7 μmol) yielded the [bis-(4-methoxy-phenyl)-phenyl-methyl]-{(R)-5-[5-(6-chloro-benzothiazol-2-yl)-2-fluoro-phenyl]-6,6-difluoro-5,7,7-trimethyl-2,5,6,7-tetrahydro-[1,4]oxazepin-3-yl}-amine (28 mg, 76% yield) as a light yellow solid. MS (ISP): m/z=756.4 [M+H]$^+$ and 758.3 [M+2+H]$^+$.

b) (R)-5-[5-(6-Chloro-benzothiazol-2-yl)-2-fluoro-phenyl]-6,6-difluoro-5,7,7-trimethyl-2,5,6,7-tetrahydro-[1,4]oxazepin-3-ylamine hydrochloride Deprotection of [bis-(4-methoxy-phenyl)-phenyl-methyl]-{(R)-5-[5-(6-chloro-benzothiazol-2-yl)-2-fluoro-phenyl]-6,6-difluoro-5,7,7-trimethyl-2,5,6,7-tetrahydro-[1,4]oxazepin-3-yl}-amine (26 mg, 35 μmol) with trifluoroacetic acid (27 μl, 349 μmol), treatment with hydrochloric acid and followed by trituration with diethyl ether yielded the (R)-5-[5-(6-Chloro-benzothiazol-2-yl)-2-fluoro-phenyl]-6,6-difluoro-5,7,7-trimethyl-2,5,6,7-tetrahydro-[1,4]oxazepin-3-ylamine hydrochloride (9 mg, 53% yield) as a white solid. MS (ISP): m/z=454.1 [M+H]$^+$ and 456.1 [M+2+H]$^+$.

Example 22

(R)-6,6-Difluoro-5-[2-fluoro-5-(1-pyridin-2-yl-1H-imidazol-4-yl)-phenyl]-5,7,7-trimethyl-2,5,6,7-tetrahydro-[1,4]oxazepin-3-ylamine In a reaction sequence analogous to that described for the preparation of Example 19 the title compound was obtained as follows:

a) [Bis-(4-methoxy-phenyl)-phenyl-methyl]-{(R)-6, 6-difluoro-5-[2-fluoro-5-(1-pyridin-2-yl-1H-imidazol-4-yl)-phenyl]-5,7,7-trimethyl-2,5,6,7-tetrahydro-[1,4]oxazepin-3-yl}-amine Reaction of [bis-(4-methoxy-phenyl)-phenyl-methyl]-{(R)-5-[5-(5,5-dimethyl-[1,3,2]dioxaborinan-2-yl)-2-fluoro-phenyl]-6,6-difluoro-5,7,7-trimethyl-2,5,6,7-tetrahydro-[1,4]oxazepin-3-yl}-amine (intermediate B10.1) (300 mg, 380 μmol) with 2-(4-bromo-1H-imidazol-1-yl)pyridine [CAS 556775-77-0; J. Med. Chem. 47(19), 4645 (2004)] (111 mg, 494 μmol) yielded the [bis-(4-methoxy-phenyl)-phenyl-methyl]-{(R)-6,6-difluoro-5-[2-fluoro-5-(1-pyridin-2-yl-1H-imidazol-4-yl)-phenyl]-5,7,7-trimethyl-2,5,6,7-tetrahydro-[1,4]oxazepin-3-yl}-amine (71 mg, 25% yield) as a light red foam. MS (ISP): m/z=732.5 [M+H]$^+$.

b) (R)-6,6-Difluoro-5-[2-fluoro-5-(1-pyridin-2-yl-1H-imidazol-4-yl)-phenyl]-5,7,7-trimethyl-2,5,6,7-tetrahydro-[1,4]oxazepin-3-ylamine Deprotection of [bis-(4-methoxy-phenyl)-phenyl-methyl]-{(R)-6,6-difluoro-5-[2-fluoro-5-(1-pyridin-2-yl-1H-imidazol-4-yl)-phenyl]-5,7,7-trimethyl-2,5,6,7-tetrahydro-[1,4]oxazepin-3-yl}-amine (68 mg, 94 μmol) with trifluoroacetic acid (73 μl, 937 μmol) and chromatography on an amine-silica phase yielded the (R)-6,6-difluoro-5-[2-fluoro-5-(1-pyridin-2-yl-1H-imidazol-4-yl)-phenyl]-5,7,7-trimethyl-2,5,6,7-tetrahydro-[1,4]oxazepin-3-yl amine (15 mg, 37% yield) as a white foam. MS (ISP): m/z=430.3 [M+H]$^+$.

Example 23

(R)-6,6-Difluoro-5-{2-fluoro-5-[1-(5-trifluoromethyl-pyridin-2-yl)-1H-imidazol-4-yl]-phenyl}-5,7,7-trimethyl-2,5,6,7-tetrahydro-[1,4]oxazepin-3-ylamine In a reaction sequence analogous to that described for the preparation of Example 19 the title compound was obtained as follows:

a) [Bis-(4-methoxy-phenyl)-phenyl-methyl]-((R)-6, 6-difluoro-5-{2-fluoro-5-[1-(5-trifluoromethyl-pyridin-2-yl)-1H-imidazol-4-yl]-phenyl}-5,7,7-trimethyl-2,5,6,7-tetrahydro-[1,4]oxazepin-3-yl)-amine Reaction of [bis-(4-methoxy-phenyl)-phenyl-methyl]-{(R)-5-[5-(5,5-dimethyl-[1,3,2]dioxaborinan-2-yl)-2-fluoro-phenyl]-6,6-difluoro-5,7,7-trimethyl-2,5,6,7-tetrahydro-[1,4]oxazepin-3-yl}-amine (intermediate B10.1) (300 mg, 380 µmol) with 2-(4-bromo-1H-imidazol-1-yl)-5-(trifluoromethyl)pyridine (111 mg, 380 µmol) yielded the [bis-(4-methoxy-phenyl)-phenyl-methyl]-((R)-6,6-difluoro-5-{2-fluoro-5-[1-(5-trifluoromethyl-pyridin-2-yl)-1H-imidazol-4-yl]-phenyl}-5,7,7-trimethyl-2,5,6,7-tetrahydro-[1,4]oxazepin-3-yl)-amine (77 mg, 25% yield) as a yellow foam. MS (ISP): m/z=800.3 [M+H]$^+$.

The 2-(4-bromo-1H-imidazol-1-yl)-5-(trifluoromethyl)pyridine was obtained as follows:

A dried pressure tube was charged with 4-bromo-1H-imidazole (100 mg, 667 µmol), tetrahydrofuran (3 ml), N,N-dimethylformamide (2 ml), 2-(methylsulfonyl)-5-(trifluoromethyl)pyridine (150 mg, 667 µmol), and cesium carbonate (261 mg, 800 µmol). The tube was sealed and heated at 105° C. for 16 hours. For the workup, the reaction mixture was evaporated at reduced pressure and the residue directly purified by chromatography on silica gel using a gradient of heptane/ethyl acetate=100:0 to 60:30 as the eluent. The 2-(4-bromo-1H-imidazol-1-yl)-5-(trifluoromethyl)pyridine (167 mg, 86% yield) was obtained as a crystalline white solid. MS (ISP): m/z=292.0 [M+H]$^+$ and 294.2 [M+2+H]$^+$.

b) (R)-6,6-Difluoro-5-[2-fluoro-5-(1-pyridin-2-yl-1H-imidazol-4-yl)-phenyl]-5,7,7-trimethyl-2,5,6,7-tetrahydro-[1,4]oxazepin-3-ylamine Deprotection of [bis-(4-methoxy-phenyl)-phenyl-methyl]-((R)-6,6-difluoro-5-{2-fluoro-5-[1-(5-trifluoromethyl-pyridin-2-yl)-1H-imidazol-4-yl]-phenyl}-5,7,7-trimethyl-2,5,6,7-tetrahydro-[1,4]oxazepin-3-yl)-amine (74.5 mg, 93 µmol) with trifluoroacetic acid (73 µl, 931 µmol) and chromatography on an amine-silica phase yielded the (R)-6,6-difluoro-5-[2-fluoro-5-(1-pyridin-2-yl-1H-imidazol-4-yl)-phenyl]-5,7,7-trimethyl-2,5,6,7-tetrahydro-[1,4]oxazepin-3-ylamine (38 mg, 83% yield) as an off-white foam. MS (ISP): m/z=498.4 [M+H]$^+$.

Example 24

(R)-5-[5-(3-Chloro-phenylethynyl)-2,4-difluoro-phenyl]-6,6-difluoro-5,7,7-trimethyl-2,5,6,7-tetrahydro-[1,4]oxazepin-3-ylamine In a reaction sequence analogous to that described for the preparation of Example 9 the title compound was obtained as follows:

a) (R)-5-[5-(3-Chloro-phenylethynyl)-2,4-difluoro-phenyl]-6,6-difluoro-5,7,7-trimethyl-[1,4]oxazepan-3-one Reaction of (R)-5-(5-bromo-2,4-fluorophenyl)-6,6-difluoro-5,7,7-trimethyl-1,4-oxazepan-3-one (intermediate B6.2) (444 mg, 1.16 mmol) and 1-chloro-3-ethynylbenzene (316 mg, 2.31 mmol) yielded the (R)-5-[5-(3-chloro-phenylethynyl)-2,4-difluoro-phenyl]-6,6-difluoro-5,7,7-trimethyl-[1,4]oxazepan-3-one in quantitative yield as a brown oil. MS (ISP): m/z=440.2 [M+2+H]$^+$ and 442.2 [M+H]$^+$.

b) (R)-5-[5-(3-Chloro-phenylethynyl)-2,4-difluoro-phenyl]-6,6-difluoro-5,7,7-trimethyl-[1,4]oxazepan-3-thione The reaction of (R)-5-[5-(3-chloro-phenylethynyl)-2,4-difluoro-phenyl]-6,6-difluoro-5,7,7-trimethyl-[1,4]oxazepan-3-one (622 mg, 1.14 mmol) with Lawesson's reagent (572 mg, 1.41 mmol) in 1,4-dioxane (40 ml) yielded the (R)-5-[5-(3-chloro-phenylethynyl)-2,4-difluoro-phenyl]-6,6-difluoro-5,7,7-trimethyl-[1,4]oxazepan-3-thione (432 mg, 67% yield) as a light brown gum.

c) (R)-5-[5-(3-Chloro-phenylethynyl)-2,4-difluoro-phenyl]-6,6-difluoro-5,7,7-trimethyl-2,5,6,7-tetrahydro-[1,4]oxazepin-3-ylamine The ammonolysis of (R)-5-[5-(3-chloro-phenylethynyl)-2,4-difluoro-phenyl]-6,6-difluoro-5,7,7-trimethyl-[1,4]oxazepan-3-thione (432 mg, 948 µmol) with ammonia (7M in methanol, 8.1 ml) and tert-butylhydroperoxide (70% in water, 781 µl, 5.69 mmol) in methanol (10 ml) yielded the (R)-5-[5-(3-chloro-phenylethynyl)-2,4-difluoro-phenyl]-6,6-difluoro-5,7,7-trimethyl-2,5,6,7-tetrahydro-[1,4]oxazepin-3-ylamine (144 mg, 35% yield) as a white foam. MS (ISP): m/z=439.1 [M+H]$^+$ and 441.3 [M+2+H]$^+$.

Example 25

(R)-6,6-Difluoro-5-(2,4-difluoro-5-pyrimidin-5-yl-phenyl)-5,7,7-trimethyl-2,5,6,7-tetrahydro-[1,4]oxazepin-3-ylamine In a manner analogous to that described for the preparation of Example 1 (method A), the reaction of (R)-5-(5-bromo-2,4-difluoro-phenyl)-6,6-difluoro-5,7,7-trimethyl-2,5,6,7-tetrahydro-[1,4]oxazepin-3-ylamine (intermediate B8.2) (100 mg, 261 µmol) with pyrimidin-5-ylboronic acid (32.3 mg, 261 µmol) in tetrahydrofuran (8 ml) and water (4 ml), with [1,1'-bis(diphenylphosphino)ferrocene]dichloropalladium (II) dichloromethane complex (10.7 mg, 13 µmol) as the catalyst and cesium carbonate (340 mg, 1.04 mmol), yielded the (R)-6,6-difluoro-5-(2,4-difluoro-5-pyrimidin-5-yl-phenyl)-5,7,7-trimethyl-2,5,6,7-tetrahydro-[1,4]oxazepin-3-ylamine (25 mg, 25% yield) as a light yellow solid. MS (ISP): m/z=383.2 [M+H]$^+$.

Example 26

(R)-5-[5-(5-Chloro-pyridin-3-yl)-2,4-difluoro-phenyl]-6,6-difluoro-5,7,7-trimethyl-2,5,6,7-tetrahydro-[1,4]oxazepin-3-ylamine In a manner analogous to that described for the preparation of Example 1 (method A), the reaction of (R)-5-(5-bromo-2,4-difluoro-phenyl)-6,6-difluoro-5,7,7-trimethyl-2,5,6,7-tetrahydro-[1,4]oxazepin-3-ylamine (intermediate B8.2) (100 mg, 261 µmol) with 5-chloropyridin-3-ylboronic acid (41.1 mg, 261 µmol) in tetrahydrofuran (8 ml) and water (4 ml), with [1,1'-bis(diphenylphosphino)ferrocene]dichloropalladium(II) dichloromethane complex (10.7 mg, 13 µmol) as the catalyst and cesium carbonate (340 mg, 1.04 mmol), yielded the (R)-5-[5-(5-chloro-pyridin-3-yl)-2,4-difluoro-phenyl]-6, 6-difluoro-5,7,7-trimethyl-2,5,6,7-tetrahydro-[1,4]oxazepin-3-ylamine (59 mg, 55% yield) as a white solid. MS (ISP): m/z=416.2 [M+H]$^+$.

Example 27

5'-(((R)-3-Amino-6,6-difluoro-5,7,7-trimethyl-2,5,6,7-tetrahydro-[1,4]oxazepin-5-yl)-2',4'-difluoro-biphenyl-4-carbonitrile In a manner analogous to that described for the preparation of Example 1 (method A), the reaction of (R)-5-(5-bromo-2,4-difluoro-phenyl)-6,6-difluoro-5,7,7-trimethyl-2,5,6,7-tetrahydro-[1,4]oxazepin-3-ylamine (intermediate B8.2) (100 mg, 261 µmol) with 4-cyanophenylboronic acid (38.3 mg, 261 µmol) in tetrahydrofuran (8 ml) and water (4 ml), with [1,1'-bis(diphenylphosphino)ferrocene]dichloropalladium (II) dichloromethane complex (10.7 mg, 13 µmol) as the catalyst and cesium carbonate (340 mg, 1.04 mmol), yielded the 5'-((R)-3-amino-6,6-difluoro-5,7,7-trimethyl-2,5,6,7-tetrahydro-[1,4]oxazepin-5-yl)-2',4'-difluoro-biphenyl-4-carbonitrile (87 mg, 82% yield) as a light yellow oil. MS (ISP): m/z=406.2 [M+H]$^+$.

Example 28

5'-((R)-3-Amino-6,6-difluoro-5,7,7-trimethyl-2,5,6,7-tetrahydro-[1,4]oxazepin-5-yl)-2',4'-difluoro-biphenyl-3-carbonitrile In a manner analogous to that described for the preparation of Example 1 (method A), the reaction of (R)-5-(5-bromo-2,4-difluoro-phenyl)-6,6-difluoro-5,7,7-trimethyl-2,5,6,7-tetrahydro-[1,4]oxazepin-3-ylamine (intermediate B8.2) (100 mg, 261 µmol) with 3-cyanophenylboronic acid (38.3 mg, 261 µmol) in tetrahydrofuran (8 ml) and water (4 ml), with [1,1'-bis(diphenylphosphino)ferrocene]dichloropalladium (II) dichloromethane complex (10.7 mg, 13 µmol) as the catalyst and cesium carbonate (340 mg, 1.04 mmol), yielded the 5'-((R)-3-amino-6,6-difluoro-5,7,7-trimethyl-2,5,6,7-tetrahydro-[1,4]oxazepin-5-yl)-2',4'-difluoro-biphenyl-3-carbonitrile (35 mg, 33% yield) as a light yellow oil. MS (ISP): m/z=406.3 [M+H]$^+$.

Example 29

(R)-6,6-Difluoro-5-{2,4-difluoro-5-[1-(4-fluoro-phenyl)-1H-pyrazol-4-yl]-phenyl}-5,7,7-trimethyl-2,5,6,7-tetrahydro-[1,4]oxazepin-3-ylamine In a manner analogous to that described for the preparation of Example 1 (method A), the reaction of (R)-5-(5-bromo-2,4-difluoro-phenyl)-6,6-difluoro-5,7,7-trimethyl-2,5,6,7-tetrahydro-[1,4]oxazepin-3-ylamine (intermediate B8.2) (100 mg, 261 µmol) with 1-(4-fluorophenyl)-1H-pyrazol-4-ylboronic acid (64.5 mg, 313 µmol) in 1,2-dimethoxyethane (2 ml) and water (1 ml), with [1,1'-bis(diphenylphosphino)ferrocene]dichloropalladium(II) dichloromethane complex (10.7 mg, 13 µmol) as the catalyst and cesium carbonate (340 mg, 1.04 mmol), yielded the (R)-6,6-difluoro-5-{2,4-difluoro-5-[1-(4-fluoro-phenyl)-1H-pyrazol-4-yl]-phenyl}-5,7,7-trimethyl-2,5,6,7-tetrahydro-[1,4]oxazepin-3-ylamine (49 mg, 40% yield) as a white foam. MS (ISP): m/z=465.3 [M+H]$^+$.

Example 30

(R)-5-[2,4-Difluoro-5-(2-methoxy-pyrimidin-5-yl)-phenyl]-6,6-difluoro-5,7,7-trimethyl-2,5,6,7-tetrahydro-[1,4]oxazepin-3-ylamine formate a) (R)-5-[2,4-Difluoro-5-(2-methoxy-pyrimidin-5-yl)-phenyl]-6,6-difluoro-5,7,7-trimethyl-[1,4]oxazepan-3-one In a manner analogous to that described in Example 19a), the reaction of (R)-5-[5-(5,5-dimethyl-[1,3,2]dioxaborinan-2-yl)-2,4-difluoro-phenyl]-6,6-difluoro-5,7,7-trimethyl-[1,4]oxazepan-3-one (intermediate D1.1) (134 mg, 321 µmol) with 5-bromo-2.methoxypyrimidine (102 mg, 541 µmol) in tetrahydrofuran (4 ml) and water (1 ml), with [1,1'-bis(diphenylphosphino)ferrocene]dichloropalladium(II) (9.9 mg, 13 µmol) as the catalyst and cesium carbonate (353 mg, 1.08 mmol), yielded the (R)-5-[2,4-difluoro-5-(2-methoxy-pyrimidin-5-yl)-phenyl]-6,6-difluoro-5,7,7-trimethyl-[1,4]oxazepan-3-one (36 mg, 32%) as an off-white solid. MS (ISP): m/z=414.3 [M+H]$^+$.

In a reaction sequence analogous to that described for the preparation of Example 2 the title compound was obtained as follows:

b) (R)-5-[2,4-difluoro-5-(2-methoxy-pyrimidin-5-yl)-phenyl]-6,6-difluoro-5,7,7-trimethyl-[1,4]oxazepan-3-thione The reaction of (R)-5-[2,4-difluoro-5-(2-methoxy-pyrimidin-5-yl)-phenyl]-6,6-difluoro-5,7,7-trimethyl-[1,4]oxazepan-3-one (82 mg, 198 µmol) with Lawesson's reagent (80.2 mg, 198 µmol) in 1,4-dioxane (3 ml) yielded the (R)-5-[2,4-difluoro-5-(2-methoxy-pyrimidin-5-yl)-phenyl]-6,6-difluoro-5,7,7-trimethyl-[1,4]oxazepan-3-thione (53 mg, 62% yield) as a white solid. MS (ISP): m/z=430.3 [M+H]$^+$.

c) (R)-5-[2,4-Difluoro-5-(2-methoxy-pyrimidin-5-yl)-phenyl]-6,6-difluoro-5,7,7-trimethyl-2,5,6,7-tetrahydro-[1,4]oxazepin-3-ylamine formate The ammonolysis of (R)-5-[2,4-difluoro-5-(2-methoxy-pyrimidin-5-yl)-phenyl]-6,6-difluoro-5,7,7-trimethyl-[1,4]oxazepan-3-thione (44.3 mg, 103 µmol) with ammonia (7M in methanol, 884 µl, 6.19 mmol) and tert-butylhydroperoxide (70% in water, 99.2 µl, 1.03 mmol) in methanol (1.5 ml) yielded the (R)-5-[2,4-difluoro-5-(2-methoxy-pyrimidin-5-yl)-phenyl]-6,6-difluoro-5,7,7-trimethyl-2,5,6,7-tetrahydro-[1,4]oxazepin-3-ylamine which was treated with formic acid, evaporated at reduced pressure, finally dried at 60° C. at high vacuum for 18 hours. The (R)-5-[2,4-difluoro-5-(2-methoxy-pyrimidin-5-yl)-phenyl]-6,6-difluoro-5,7,7-trimethyl-2,5,6,7-tetrahydro-[1,4]oxazepin-3-ylamine formate (18 mg, 39% yield) was obtained as an amorphous colorless material. MS (ISP): m/z=413.2 [M+H]$^+$.

Example 31

(R)-5-[5-(6-Chloro-benzooxazol-2-yl)-2,4-difluoro-phenyl]-6,6-difluoro-5,7,7-trimethyl-2,5,6,7-tetrahydro-[1,4]oxazepin-3-ylamine a) (R)-5-[5-(6-Chloro-benzooxazol-2-yl)-2,4-difluoro-phenyl]-6,6-difluoro-5,7,7-trimethyl-[1,4]oxazepan-3-one In a manner analogous to that described in Example 19a), the reaction of (R)-5-[5-(5,5-dimethyl-[1,3,2]dioxaborinan- 2-yl)-2,4-difluoro-phenyl]-6,6-difluoro-5,7,7-trimethyl-[1,4]oxazepan-3-one (intermediate D1.1) (390 mg, 935 μmol) with 2,6-dichlorobenzoxazole (173 mg, 921 μmol) in tetrahydrofuran (5.8 ml) and water (1.4 ml), with [1,1'-bis(diphenylphosphino)ferrocene]dichloropalladium(II) (16.9 mg, 23 μmol) as the catalyst and cesium carbonate (600 mg, 1.84 mmol), yielded the (R)-5-[5-(6-chloro-benzooxazol-2-yl)-2,4-difluoro-phenyl]-6,6-difluoro-5,7,7-trimethyl-[1,4]oxazepan-3-one (184 mg, 80%) as a grey solid. MS (ISP): m/z=457.2 [M+H]$^+$ and 459.2 [M+2+H]$^+$.

In a reaction sequence analogous to that described for the preparation of Example 2 the title compound was obtained as follows:

b) (R)-5-[5-(6-chloro-benzooxazol-2-yl)-2,4-difluoro-phenyl]-6,6-difluoro-5,7,7-trimethyl-[1,4]oxazepan-3-thione The reaction of (R)-5-[5-(6-chloro-benzooxazol-2-yl)-2,4-difluoro-phenyl]-6,6-difluoro-5,7,7-trimethyl-[1,4]oxazepan-3-one (164 mg, 359 μmol) with Lawesson's reagent (145 mg, 359 μmol) in 1,4-dioxane (3.5 ml) yielded the (R)-5-[5-(6-chloro-benzooxazol-2-yl)-2,4-difluoro-phenyl]-6,6-difluoro-5,7,7-trimethyl-[1,4]oxazepan-3-thione (148 mg, 87% yield) as a white solid. MS (ISP): m/z=473.0 [M+H]$^+$ and 475.1 [M+2+H]$^+$.

c) (R)-5-[5-(6-Chloro-benzooxazol-2-yl)-2,4-difluoro-phenyl]-6,6-difluoro-5,7,7-trimethyl-2,5,6,7-tetrahydro-[1,4]oxazepin-3-ylamine The ammonolysis of (R)-5-[5-(6-chloro-benzooxazol-2-yl)-2,4-difluoro-phenyl]-6,6-difluoro-5,7,7-trimethyl-[1,4]oxazepan-3-thione (116 mg, 245 μmol) with ammonia (7M in methanol, 2.1 ml, 14.7 mmol) and tert-butylhydroperoxide (70% in water, (236 μl, 2.45 mmol) in methanol (3.9 ml) yielded the (R)-5-[5-(6-chloro-benzooxazol-2-yl)-2,4-difluoro-phenyl]-6,6-difluoro-5,7,7-trimethyl-2,5,6,7-tetrahydro-[1,4]oxazepin-3-ylamine (38 mg, 34% yield) as a white solid. MS (ISP): m/z=456.2 [M+H]$^+$ and 458.2 [M+2+H]$^+$.

Example 32

(R)-5-[5-(5-Chloro-pyrimidin-2-yl)-2,4-difluoro-phenyl]-6,6-difluoro-5,7,7-trimethyl-2,5,6,7-tetrahydro-[1,4]oxazepin-3-ylamine a) (R)-5-[5-(5-Chloro-pyrimidin-2-yl)-2,4-difluoro-phenyl]-6,6-difluoro-5,7,7-trimethyl-[1,4]oxazepan-3-one In a manner analogous to that described in Example 19a), the reaction of (R)-5-[5-(5,5-dimethyl-[1,3,2]dioxaborinan-2-yl)-2,4-difluoro-phenyl]-6,6-difluoro-5,7,7-trimethyl-[1,4]oxazepan-3-one (intermediate D1.1) (195 mg, 467 μmol) with 5-chloro-2-iodopyrimidine (222 mg, 921 μmol) in tetrahydrofuran (5.8 ml) and water (1.4 ml), with [1,1'-bis(diphenylphosphino)ferrocene]dichloropalladium(II) (16.9 mg, 23 μmol) as the catalyst and cesium carbonate (600 mg, 1.84 mmol), yielded the (R)-5-[5-(5-chloro-pyrimidin-2-yl)-2,4-difluoro-phenyl]-6,6-difluoro-5,7,7-trimethyl-[1,4]oxazepan-3-one (181 mg, 83%) as an off-white solid. MS (ISP): m/z=418.2 [M+H]$^+$ and 420.2 [M+2+H]$^+$.

In a reaction sequence analogous to that described for the preparation of Example 2 the title compound was obtained as follows:

b) (R)-5-[5-(5-chloro-pyrimidin-2-yl)-2,4-difluoro-phenyl]-6,6-difluoro-5,7,7-trimethyl-[1,4]oxazepan-3-thione The reaction of (R)-5-[5-(5-chloro-pyrimidin-2-yl)-2,4-difluoro-phenyl]-6,6-difluoro-5,7,7-trimethyl-[1,4]oxazepan-3-o (164 mg, 359 μmol) with Lawesson's reagent (151 mg, 373 μmol) in 1,4-dioxane (5 ml) yielded the (R)-5-[5-(5-chloro-pyrimidin-2-yl)-2,4-difluoro-phenyl]-6,6-difluoro-5,7,7-trimethyl-[1,4]oxazepan-3-thione (131 mg, 81% yield) as a white solid. MS (ISP): m/z=434.2 [M+H]$^+$.

c) (R)-5-[5-(5-Chloro-pyrimidin-2-yl)-2,4-difluoro-phenyl]-6,6-difluoro-5,7,7-trimethyl-2,5,6,7-tetrahydro-[1,4]oxazepin-3-ylamine The ammonolysis of (R)-5-[5-(5-chloro-pyrimidin-2-yl)-2,4-difluoro-phenyl]-6,6-difluoro-5,7,7-trimethyl-[1,4]oxazepan-3-thione (114 mg, 263 μmol) with ammonia (7M in methanol, 2.3 ml, 15.8 mmol) and tert-butylhydroperoxide (70% in water, (253 μl, 2.63 mmol) in methanol (3.9 ml) yielded the (R)-5-[5-(5-chloro-pyrimidin-2-yl)-2,4-difluoro-phenyl]-6,6-difluoro-5,7,7-trimethyl-2,5,6,7-tetrahydro-[1,4]oxazepin-3-ylamine (26 mg, 24% yield) as a white solid. MS (ISP): m/z=417.2 [M+H]$^+$.

Example 33

6-[3-((R)-3-Amino-6,6-difluoro-5,7,7-trimethyl-2,5,6,7-tetrahydro-[1,4]oxazepin-5-yl)-4-fluoro-phenylethynyl]-nicotinonitrile a) (R)-6,6-Difluoro-5-(2-fluoro-5-iodo-phenyl)-5,7,7-trimethyl-[1,4]oxazepane-3-thione In a manner analogous to that described for the preparation of intermediate B7, the reaction of (R)-6,6-difluoro-5-(2-fluoro-5-iodo-phenyl)-5,7,7-trimethyl-[1,4]oxazepan-3-one (intermediate B6".1) (1.455 g, 3.52 mmol) with Lawesson's reagent (1.42 g, 3.52 mmol), yielded the title compound (1.44 g, 95% yield) as a colorless oil. MS (ISP): m/z=430.1 [M+H]$^+$.

b) (R)-6,6-Difluoro-5-(2-fluoro-5-iodo-phenyl)-5,7,7-trimethyl-2,5,6,7-tetrahydro-[1,4]oxazepin-3-ylamine In a manner analogous to that described for the preparation of intermediate B8.1, the ammonolysis of (R)-6,6-difluoro-5-(2-fluoro-5-iodo-phenyl)-5,7,7-trimethyl-[1,4]oxazepane-3-thione (3.475 g, 8.1 mmol) yielded the title compound (1.633 g, 49% yield) as a light yellow oil. MS (ISP): m/z=413.1 [M+H]$^+$.

c) (R)-6,6-Difluoro-5-(2-fluoro-5-trimethylsilanyl-ethynyl-phenyl)-5,7,7-trimethyl-2,5,6,7-tetrahydro-[1,4]oxazepin-3-ylamine In a manner analogous to that described in Example 9a), palladium-catalyzed coupling of (R)-6,6-Difluoro-5-(2-fluoro-5-iodo-phenyl)-5,7,7-trimethyl-2,5,6,7-tetrahydro-[1,4]oxazepin-3-ylamine (485 mg, 1.18 mmol) with ethynyltrimethylsilane yielded the title compound (350 mg, 78% yield) as a yellow oil. MS (ISP): m/z=383.2 [M+H]$^+$.

d) 6-[3-((R)-3-Amino-6,6-difluoro-5,7,7-trimethyl-2, 5,6,7-tetrahydro-[1,4]oxazepin-5-yl)-4-fluoro-phenylethynyl]-nicotinonitrile A dried flask was charged under an atmosphere of argon with a solution of 6-iodo-nicotinonitrile (25 mg, 109 μmol) and (R)-6,6-Difluoro-5-(2-fluoro-5-trimethylsilanylethynyl-phenyl)-5,7,7-trimethyl-2,5,6,7-tetrahydro-[1,4]oxazepin-3-ylamine (50 mg, 131 μmol) in dimethylformamide (368 μl) (solution A). A second dried flask was charged under an atmosphere of argon with dimethylformamide (368 μl), then successively with bis(triphenylphosphine)palladium(II)chloride (5.47 mg, 7.6 μmol), triphenylphoshine (1.14 mg, 4.4 μmol), copper(I)iodide (0.42 mg, 2.1 μmol), triethylamine (55.2 mg, 0.545 mmol), and tetrabutylammoniumiodide (41.1 mg, 109 μmol) were added. The mixture was heated to 40° C., and solution A was added dropwise. The temperature was raised to 60° C. and a solution of tetrabutylammoniumfluoride (1M in tetrahydrofuran; 142 μl) was added dropwise. Stirring was continued for 16 hours. For the workup, the reaction mixture was evaporated at reduced pressure and the residue directly purified by chromatography on silica gel using a gradient of heptane/ethyl acetate=100:0 to 50:50 as the eluent. The 6-[3-((R)-3-amino-6,6-difluoro-5,7,7-trimethyl-2,5,6,7-tetrahydro-[1,4]oxazepin-5-yl)-4-fluoro-phenylethynyl]-nicotinonitrile (18 mg, 40% yield) was obtained as a colorless oil. MS (ISP): m/z=413.2 [M+H]$^+$.

In a manner analogous to that described in Example 33d) the following compounds were obtained:

Example 34

(R)-5-[5-(5-Chloro-pyrimidin-2-ylethynyl)-2-fluoro-phenyl]-6,6-difluoro-5,7,7-trimethyl-2,5,6,7-tetrahydro-[1,4]oxazepin-3-ylamine The coupling of (R)-6,6-difluoro-5-(2-fluoro-5-trimethylsilanylethynyl-phenyl)-5,7,7-trimethyl-2,5,6,7-tetrahydro-[1,4]oxazepin-3-ylamine [Example 33c)] (50 mg, 131 μmol) with 5-chloro-2-iodo-pyrimidine (26.2 mg, 109 μmol) yielded the title compound (5 mg, 11% yield) as a light yellow solid. MS (ISP): m/z=423.2 [M+H]$^+$ and 425.2 [M+2H]$^+$.

Example 35

(R)-5-[5-(2-Chloro-pyridin-4-ylethynyl)-2-fluoro-phenyl]-6,6-difluoro-5,7,7-trimethyl-2,5,6,7-tetrahydro-[1,4]oxazepin-3-ylamine The coupling of (R)-6,6-difluoro-5-(2-fluoro-5-trimethylsilanylethynyl-phenyl)-5,7,7-trimethyl-2,5,6,7-tetrahydro-[1,4]oxazepin-3-ylamine [Example 33c)] (50 mg, 131 μmol) with 2-chloro-4-iodo-pyridine (26.1 mg, 109 μmol) yielded the title compound (25 mg, 54% yield) as a light yellow oil. MS (ISP): m/z=422.1 [M+H]$^+$ and 424.2 [M+2H]$^+$.

Example 36

2-[3-((R)-3-Amino-6,6-difluoro-5,7,7-trimethyl-2,5,6,7-tetrahydro-[1,4]oxazepin-5-yl)-4-fluoro-phenylethynyl]-isonicotinonitrile The coupling of (R)-6,6-difluoro-5-(2-fluoro-5-trimethylsilanylethynyl-phenyl)-5,7,7-trimethyl-2,5,6,7-tetrahydro-[1,4]oxazepin-3-ylamine [Example 33c)] (40 mg, 105 μmol) with 2-iodo-isonicotinonitrile (20.1 mg, 87 μmol) yielded the title compound (10 mg, 28% yield) as a light yellow solid. MS (ISP): m/z=413.3 [M+H]$^+$.

Example 37

(R)-5-[5-(6-Chloro-pyridazin-3-ylethynyl)-2-fluoro-phenyl]-6,6-difluoro-5,7,7-trimethyl-2,5,6,7-tetrahydro-[1,4]oxazepin-3-ylamine The coupling of (R)-6,6-difluoro-5-(2-fluoro-5-trimethylsilanylethynyl-phenyl)-5,7,7-trimethyl-2,5,6,7-tetrahydro-[1,4]oxazepin-3-ylamine [Example 33c)] (50 mg, 131 μmol) with 3-chloro-6-iodo-pyridazine (26.2 mg, 109 μmol) yielded the title compound (11 mg, 24% yield) as a light yellow solid. MS (ISP): m/z=423.1 [M+H]$^+$ and 425.1 [M+2H]$^+$.

Example 38

(R)-5-[5-(5-Chloro-pyridin-3-ylethynyl)-2-fluoro-phenyl]-6,6-difluoro-5,7,7-trimethyl-2,5,6,7-tetrahydro-[1,4]oxazepin-3-ylamine The coupling of (R)-6,6-difluoro-5-(2-fluoro-5-trimethylsilanylethynyl-phenyl)-5,7,7-trimethyl-2,5,6,7-tetrahydro-[1,4]oxazepin-3-ylamine [Example 33c)] (50 mg, 131 μmol) with 3-chloro-5-iodo-pyridine (26.1 mg, 109 μmol) yielded the title compound (15 mg, 33% yield) as a light yellow oil. MS (ISP): m/z=422.1 [M+H]$^+$ and 424.2 [M+2H]$^+$.

Example 39

(R)-6,6-Difluoro-5-(2-fluoro-5-pyridin-2-ylethynyl-phenyl)-5,7,7-trimethyl-2,5,6,7-tetrahydro-[1,4]oxazepin-3-ylamine The coupling of (R)-6,6-difluoro-5-(2-fluoro-5-trimethylsilanylethynyl-phenyl)-5,7,7-trimethyl-2,5,6,7-tetrahydro-[1,4]oxazepin-3-ylamine [Example 33c)] (50 mg, 131 μmol) with 2-iodo-pyridine (22.3 mg, 109 μmol) yielded the title compound (26 mg, 62% yield) as a light yellow oil. MS (ISP): m/z=388.2 [M+H]$^+$.

Example 40

(R)-6,6-Difluoro-5-[2-fluoro-5-(5-methoxy-pyrazin-2-ylethynyl)-phenyl]-5,7,7-trimethyl-2,5,6,7-tetrahydro-[1,4]oxazepin-3-ylamine The coupling of (R)-6,6-difluoro-5-(2-fluoro-5-trimethylsilanylethynyl-phenyl)-5,7,7-trimethyl-2,5,6,7-tetrahydro-[1,4]oxazepin-3-ylamine [Example 33c)] (50 mg, 131 μmol) with 2-bromo-5-methoxy-pyrazine (20.6 mg, 109 μmol) yielded the title compound (9 mg, 20% yield) as a yellow solid. MS (ISP): m/z=419.2 [M+H]$^+$.

Example 41

(R)-5-[5-(5-Chloro-benzooxazol-2-yl)-2,4-difluoro-phenyl]-6,6-difluoro-5,7,7-trimethyl-2,5,6,7-tetrahydro-[1,4]oxazepin-3-ylamine a) (R)-5-[5-(5-Chloro-benzooxazol-2-yl)-2,4-difluoro-phenyl]-6,6-difluoro-5,7,7-trimethyl-[1,4]oxazepan-3-one In a manner analogous to that described in Example 19a), the palladium-catalyzed coupling of (R)-5-[5-(5,5-dimethyl-

[1,3,2]dioxaborinan-2-yl)-2,4-difluoro-phenyl]-6,6-difluoro-5,7,7-trimethyl-[1,4]oxazepan-3-one (intermediate D1.1) and 2,5-dichlorobenzo[d]oxazole yielded the title compound (42% yield) as a white solid. MS (ISP): m/z=457.2 [M+H]⁺.

b) (R)-5-[5-(5-Chloro-benzooxazol-2-yl)-2,4-difluoro-phenyl]-6,6-difluoro-5,7,7-trimethyl-[1,4]oxazepan-3-thione In a manner analogous to that described in Example 2b), the reaction of (R)-5-[5-(5-chloro-benzooxazol-2-yl)-2,4-difluoro-phenyl]-6,6-difluoro-5,7,7-trimethyl-[1,4]oxazepan-3-one (35 mg, 77 μmol) with Lawesson's reagent (34 mg, 84 μmol) yielded the title compound in quantitative yield as a white powder. MS (ISP): m/z=473.0 [M+H]⁺.

c) (R)-5-[5-(5-Chloro-benzooxazol-2-yl)-2,4-difluoro-phenyl]-6,6-difluoro-5,7,7-trimethyl-2,5,6,7-tetrahydro-[1,4]oxazepin-3-ylamine In a manner analogous to that described in Example 2c), the ammonolysis of (R)-5-[5-(5-chloro-benzo oxazol-2-yl)-2,4-difluoro-phenyl]-6,6-difluoro-5,7,7-trimethyl-[1,4]oxazepan-3-thione (35 mg, 74 μmol) with ammonia (7M in methanol; 0.73 ml) and tert-butylhydroperoxide (70% in water; 71 μl) yielded the title compound (14 mg, 43% yield). MS (ISP): m/z=456.3 [M+H]⁺ and 458.2 [M+2+H]⁺.

Example 42

(R)-5-[5-(5,6-Difluoro-benzooxazol-2-yl)-2,4-difluoro-phenyl]-6,6-difluoro-5,7,7-trimethyl-2,5,6,7-tetrahydro-[1,4]oxazepin-3-ylamine a) (R)-5-[5-(5,6-Difluoro-benzooxazol-2-yl)-2,4-difluoro-phenyl]-6,6-difluoro-5,7,7-trimethyl-[1,4]oxazepan-3-one In a manner analogous to that described in Example 19a), the palladium-catalyzed coupling of (R)-5-[5-(5,5-dimethyl-[1,3,2]dioxaborinan-2-yl)-2,4-difluoro-phenyl]-6,6-difluoro-5,7,7-trimethyl-[1,4]oxazepan-3-one (intermediate D1.1) and 2-chloro-5,6-difluorobenzo[d]oxazole yielded the title compound (74% yield) as a white powder. MS (ISP): m/z=459.2 [M+H]⁺.

b) (R)-5-[5-(5,6-Difluoro-benzooxazol-2-yl)-2,4-difluoro-phenyl]-6,6-difluoro-5,7,7-trimethyl-[1,4]oxazepan-3-thione In a manner analogous to that described in Example 2b), the reaction of (R)-5-[5-(5,6-difluoro-benzooxazol-2-yl)-2,4-difluoro-phenyl]-6,6-difluoro-5,7,7-trimethyl-[1,4]oxazepan-3-one (130 mg, 284 μmol) with Lawesson's reagent (126 mg, 312 μmol) yielded the title compound (83 mg, 62% yield as a white solid. MS (ISP): m/z=475.1 [M+H]⁺.

c) (R)-5-[5-(5,6-Difluoro-benzooxazol-2-yl)-2,4-difluoro-phenyl]-6,6-difluoro-5,7,7-trimethyl-2,5,6,7-tetrahydro-[1,4]oxazepin-3-ylamine In a manner analogous to that described in Example 2c), the ammonolysis of (R)-5-[5-(5,6-difluoro-benzo oxazol-2-yl)-2,4-difluoro-phenyl]-6,6-difluoro-5,7,7-trimethyl-[1,4]oxazepan-3-thione (83 mg, 175 μmol) with ammonia (7M in methanol; 1.72 ml) and tert-butylhydroperoxide (70% in water; 183 μl) yielded the title compound (19 mg, 24% yield). MS (ISP): m/z=458.2 [M+H]⁺.

Example 43

(R)-5-[2,4-Difluoro-5-(6-trifluoromethyl-benzooxazol-2-yl)-phenyl]-6,6-difluoro-5,7,7-trimethyl-2,5,6,7-tetrahydro-[1,4]oxazepin-3-ylamine a) (R)-5-[2,4-Difluoro-5-(6-trifluoromethyl-benzooxazol-2-yl)-phenyl]-6,6-difluoro-5,7,7-trimethyl-[1,4]oxazepan-3-one In a manner analogous to that described in Example 19a), the palladium-catalyzed coupling of (R)-5-[5-(5,5-dimethyl-[1,3,2]dioxaborinan-2-yl)-2,4-difluoro-phenyl]-6,6-difluoro-5,7,7-trimethyl-[1,4]oxazepan-3-one (intermediate D1.1) and 2-chloro-6-(trifluoromethyl)benzo[d]oxazole yielded the title compound (73% yield) as a white solid. MS (ISP): m/z=491.2 [M+H]⁺.

b) (R)-5-[2,4-Difluoro-5-(6-trifluoromethyl-benzooxazol-2-yl)-phenyl]-6,6-difluoro-5,7,7-trimethyl-[1,4]oxazepan-3-thione In a manner analogous to that described in Example 2b), the reaction of (R)-5-[2,4-difluoro-5-(6-trifluoromethyl-benzo oxazol-2-yl)-phenyl]-6,6-difluoro-5,7,7-trimethyl-[1,4]oxazepan-3-one (163 mg, 332 μmol) with Lawesson's reagent (145 mg, 359 μmol) yielded the title compound (113 mg, 67% yield as a white solid. MS (ISP): m/z=507.1 [M+H]⁺.

c) (R)-5-[2,4-Difluoro-5-(6-trifluoromethyl-benzooxazol-2-yl)-phenyl]-6,6-difluoro-5,7,7-trimethyl-2,5,6,7-tetrahydro-[1,4]oxazepin-3-ylamine In a manner analogous to that described in Example 2c), the ammonolysis of (R)-5-[2,4-difluoro-5-(6-trifluoromethyl-benzooxazol-2-yl)-phenyl]-6,6-difluoro-5,7,7-trimethyl-[1,4]oxazepan-3-thione (110 mg, 217 μmol) with ammonia (7M in methanol; 2.14 ml) and tert-butylhydroperoxide (70% in water; 260 μl) yielded the title compound (33 mg, 31% yield). MS (ISP): m/z=490.2 [M+H]⁺.

The invention claimed is:
1. A compound of formula I,

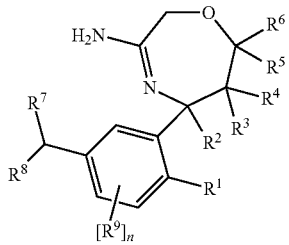

wherein
$R^1$ is selected from the groups consisting of
hydrogen and
halogen;
$R^2$ is selected from the groups consisting of
$C_{1-6}$-alkyl and
halogen-$C_{1-3}$-alkyl;

R³ is selected from the groups consisting of
hydrogen,
halogen, and
$C_{1-6}$-alkyl;
R⁴ is selected from the groups consisting of
hydrogen,
halogen, and
$C_{1-6}$-alkyl;
R⁵ is selected from the groups consisting of
hydrogen and
$C_{1-6}$-alkyl;
R⁶ is selected from the groups consisting of
hydrogen and
$C_{1-6}$-alkyl;
R⁷ and R⁸ together with the C atom to which they are attached form a group selected from the group consisting of
aryl,
aryl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{1-6}$-alkyl-NH—SO₂—, $C_{1-6}$-alkyl-SO₂—, $C_{1-6}$-alkoxy-SO₂— and $C_{1-6}$-alkyl,
heteroaryl,
heteroaryl substituted by 1-4 substituents individually selected from aryl, cyano, cyano-$C_{1-6}$-alkyl, halogen, halogen-$C_{1-6}$-alkoxy, halogen-$C_{1-6}$-alkyl, halogen-$C_{1-6}$-alkyl-heteroaryl, halogen-aryl, heteroaryl, $C_{1-6}$-alkoxy, $C_{1-6}$-alkoxy-$C_{1-6}$-alkyl, $C_{1-6}$-alkyl-NH—SO₂— and $C_{1-6}$-alkyl,
$C_{2-6}$-alkynyl,
$C_{2-6}$-alkynyl substituted by 1-5 substituents individually selected from aryl, cyano, halogen-aryl, halogen, $C_{1-6}$-alkyl, $C_{1-6}$-alkyl-aryl, cyano-heteroaryl, halogen-heteroaryl, $C_{1-6}$-alkyl-heteroaryl, heteroaryl, $C_{1-6}$-alkoxy-heteroaryl and $C_{1-6}$-alkoxy;
heterocyclyl, and
heterocyclyl substituted by 1-4 substituents individually selected from halogen, halogen-$C_{1-6}$-alkoxy, halogen-$C_{1-6}$-alkyl, $C_{1-6}$-alkoxy, $C_{1-6}$-alkoxy-$C_{1-6}$-alkyl and $C_{1-6}$-alkyl;
R⁹ is selected from the group consisting of
halogen and
$C_{1-6}$-alkyl; and
n is 0 or 1;
or a pharmaceutically acceptable salt thereof.

2. The compound according to claim 1, wherein
R¹ is selected from the groups consisting of
hydrogen and
halogen;
R² is selected from the groups consisting of
$C_{1-6}$-alkyl and
halogen-$C_{1-3}$-alkyl;
R³ is selected from the groups consisting of
hydrogen,
halogen, and
$C_{1-6}$-alkyl;
R⁴ is selected from the groups consisting of
hydrogen,
halogen, and
$C_{1-6}$-alkyl;
R⁵ is selected from the groups consisting of
hydrogen and
$C_{1-6}$-alkyl;
R⁶ is selected from the groups consisting of
hydrogen and
$C_{1-6}$-alkyl;
R⁷ and R⁸ together with the C atom to which they are attached form a group selected from the group consisting of
aryl,
aryl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{1-6}$-alkyl-NH—SO₂—, $C_{1-6}$-alkyl-SO₂—, $C_{1-6}$-alkoxy-SO₂— and $C_{1-6}$-alkyl,
heteroaryl,
heteroaryl substituted by 1-4 substituents individually selected from aryl, cyano, cyano-$C_{1-6}$-alkyl, halogen, halogen-$C_{1-6}$-alkoxy, halogen-$C_{1-6}$-alkyl, halogen-$C_{1-6}$-alkyl-heteroaryl, halogen-aryl, heteroaryl, $C_{1-6}$-alkoxy, $C_{1-6}$-alkoxy-$C_{1-6}$-alkyl, $C_{1-6}$-alkyl-NH—SO₂— and $C_{1-6}$-alkyl,
$C_{2-6}$-alkynyl,
$C_{2-6}$-alkynyl substituted by 1-5 substituents individually selected from aryl, cyano, halogen-aryl, halogen, $C_{1-6}$-alkyl, $C_{1-6}$-alkyl-aryl, $C_{1-6}$-alkyl-heteroaryl and $C_{1-6}$-alkoxy;
heterocyclyl, and
heterocyclyl substituted by 1-4 substituents individually selected from halogen, halogen-$C_{1-6}$-alkoxy, halogen-$C_{1-6}$-alkyl, $C_{1-6}$-alkoxy, $C_{1-6}$-alkoxy-$C_{1-6}$-alkyl and $C_{1-6}$-alkyl;
R⁹ is selected from the group consisting of
halogen and
$C_{1-6}$-alkyl; and
n is 0 or 1;
or a pharmaceutically acceptable salt thereof.

3. The compound according to claim 2, wherein
R¹ is halogen;
R² is $C_{1-6}$-alkyl;
R³ is halogen;
R⁴ is halogen;
R⁵ is selected from the groups consisting of
hydrogen and
$C_{1-6}$-alkyl;
R⁶ is selected from the groups consisting of
hydrogen and
$C_{1-6}$-alkyl;
R⁷ and R⁸ together with the C atom to which they are attached form a group selected from the group consisting of
aryl substituted by 1-2 substituents individually selected from cyano, halogen, $C_{1-6}$-alkyl-NH—SO₂—, and $C_{1-6}$-alkoxy-SO₂,
heteroaryl,
heteroaryl substituted by 1-2 substituents individually selected from halogen, halogen-$C_{1-6}$-alkyl-heteroaryl, halogen-aryl, heteroaryl, $C_{1-6}$-alkoxy and $C_{1-6}$-alkyl,
$C_{2-6}$-alkynyl substituted by 1-2 substituents individually selected from halogen-aryl and $C_{1-6}$-alkyl-heteroaryl, and
heterocyclyl;
R⁹ is halogen; and
n is 0 or 1.

4. The compound according to claim 1, wherein R¹ is halogen.

5. The compound according to claim 4, wherein R¹ is F.

6. The compound according to claim 1, wherein R² is $C_{1-6}$-alkyl.

7. The compound according to claim 6, wherein R² is methyl.

8. The compound according to claim 1, wherein R³ is halogen.

9. The compound according to claim 8, wherein $R^3$ is F.

10. The compound according to claim 1, wherein $R^4$ is halogen.

11. The compound according to claim 10, wherein $R^4$ is F.

12. The compound according to claim 1, wherein $R^5$ is $C_{1-6}$-alkyl.

13. The compound according to claim 12, wherein $R^5$ is methyl.

14. The compound according to claim 1, wherein $R^5$ is hydrogen.

15. The compound according to claim 1, wherein $R^6$ is $C_{1-6}$-alkyl.

16. The compound according to claim 15, wherein $R^6$ is methyl.

17. The compound according to claim 1, wherein $R^6$ is hydrogen.

18. The compound according to claim 1, wherein $R^9$ is halogen and n is 1.

19. The compound according to claim 18, wherein $R^9$ is F and n is 1.

20. The compound according to claim 1, wherein n is 0.

21. The compound according to claim 1, wherein $R^7$ and $R^8$ together with the C atom to which they are attached form a group selected from the group consisting of
   aryl substituted by 1-2 substituents individually selected from cyano and halogen,
   heteroaryl, and
   heteroaryl substituted by 1-2 substituents individually selected from halogen.

22. The compound according to claim 1, wherein $R^7$ and $R^8$ together with the C atom to which they are attached form a group selected from the groups consisting of phenyl substituted by halogen or cyano, pyrimidyl, and pyridinyl substituted by halogen.

23. The compound according to claim 1, selected from the group consisting of
   (R)-6,6-Difluoro-5-(2-fluoro-5-pyrimidin-5-yl-phenyl)-5-methyl-2,5,6,7-tetrahydro-[1,4]oxazepin-3-ylamine,
   (R)-5-{5-[1-(3-Chloro-phenyl)-1H-pyrazol-4-yl]-2-fluoro-phenyl}-6,6-difluoro-5,7,7-trimethyl-2,5,6,7-tetrahydro-[1,4]oxazepin-3-ylamine,
   3'-((R)-3-Amino-6,6-difluoro-5,7,7-trimethyl-2,5,6,7-tetrahydro-[1,4]oxazepin-5-yl)-4'-fluoro-biphenyl-3-sulfonic acid 2,2-dimethyl-propyl ester,
   3'-((R)-3-Amino-6,6-difluoro-5,7,7-trimethyl-2,5,6,7-tetrahydro-[1,4]oxazepin-5-yl)-6,4'-difluoro-biphenyl-3-carbonitrile,
   3'-((R)-3-Amino-6,6-difluoro-5,7,7-trimethyl-2,5,6,7-tetrahydro-[1,4]oxazepin-5-yl)-4'-fluoro-biphenyl-3-carbonitrile,
   3'-((R)-3-Amino-6,6-difluoro-5,7,7-trimethyl-2,5,6,7-tetrahydro-[1,4]oxazepin-5-yl)-4'-fluoro-biphenyl-3-sulfonic acid tert-butylamide,
   5-[3-((R)-3-Amino-6,6-difluoro-5,7,7-trimethyl-2,5,6,7-tetrahydro-[1,4]oxazepin-5-yl)-4-fluoro-phenyl]-pyridine-3-sulfonic acid tert-butylamide,
   3'-((R)-3-Amino-6,6-difluoro-5,7,7-trimethyl-2,5,6,7-tetrahydro-[1,4]oxazepin-5-yl)-4'-fluoro-biphenyl-4-carbonitrile,
   5'-((R)-3-Amino-6,6-difluoro-5,7,7-trimethyl-2,5,6,7-tetrahydro-[1,4]oxazepin-5-yl)-2',4'-difluoro-biphenyl-4-carbonitrile and,
   5'-((R)-3-Amino-6,6-difluoro-5,7,7-trimethyl-2,5,6,7-tetrahydro-[1,4]oxazepin-5-yl)-2',4'-difluoro-biphenyl-3-carbonitrile
   or a pharmaceutically acceptable salt thereof.

24. The compound according to claim 1, selected from the group consisting of
   6-[3-((R)-3-Amino-6,6-difluoro-5,7,7-trimethyl-2,5,6,7-tetrahydro-[1,4]oxazepin-5-yl)-4-fluoro-phenylethynyl]-nicotinonitrile,
   2-[3-((R)-3-Amino-6,6-difluoro-5,7,7-trimethyl-2,5,6,7-tetrahydro-[1,4]oxazepin-5-yl)-4-fluoro-phenylethynyl]-isonicotinonitrile,
   (R)-6,6-Difluoro-5-(2-fluoro-5-pyrimidin-5-yl-phenyl)-5,7,7-trimethyl-2,5,6,7-tetrahydro-[1,4]oxazepin-3-ylamine,
   (R)-5-(3',5'-Dichloro-4-fluoro-biphenyl-3-yl)-6,6-difluoro-5,7,7-trimethyl-2,5,6,7-tetrahydro-[1,4]oxazepin-3-ylamine,
   (R)-5-(5'-Chloro-4,3'-difluoro-biphenyl-3-yl)-6,6-difluoro-5,7,7-trimethyl-2,5,6,7-tetrahydro-[1,4]oxazepin-3-ylamine,
   (R)-5-(2,4-Difluoro-5-pyrimidin-5-yl-phenyl)-6,6-difluoro-5,7,7-trimethyl-2,5,6,7-tetrahydro-[1,4]oxazepin-3-ylamine,
   (R)-6,6-Difluoro-5-(2-fluoro-5-pyridin-2-ylethynyl-phenyl)-5,7,7-trimethyl-2,5,6,7-tetrahydro-[1,4]oxazepin-3-ylamine,
   (R)-6,6-Difluoro-5,7,7-trimethyl-5-(4,3',5'-trifluoro-biphenyl-3-yl)-2,5,6,7-tetrahydro-[1,4]oxazepin-3-ylamine,
   (R)-5-{2,4-Difluoro-5-[1-(4-fluoro-phenyl)-1H-pyrazol-4-yl]-phenyl}-6,6-difluoro-5,7,7-trimethyl-2,5,6,7-tetrahydro-[1,4]oxazepin-3-ylamine,
   (R)-5-[2,4-Difluoro-5-(6-trifluoromethyl-benzooxazol-2-yl)-phenyl]-6,6-difluoro-5,7,7-trimethyl-2,5,6,7-tetrahydro-[1,4]oxazepin-3-ylamine, and
   (R)-5-[5-(5-Chloro-pyridin-3-yl)-2-fluoro-phenyl]-6,6-difluoro-5,7,7-trimethyl-2,5,6,7-tetrahydro-[1,4]oxazepin-3-ylamine;
   or a pharmaceutically acceptable salt thereof.

25. The compound according to claim 1, selected from the group consisting of
   (R)-6,6-Difluoro-5-{2-fluoro-5-[1-(4-fluoro-phenyl)-1H-pyrazol-4-yl]-phenyl}-5,7,7-trimethyl-2,5,6,7-tetrahydro-[1,4]oxazepin-3-ylamine,
   (R)-6,6-Difluoro-5-[2-fluoro-5-(2-methyl-2H-pyrazol-3-yl)-phenyl]-5,7,7-trimethyl-2,5,6,7-tetrahydro-[1,4]oxazepin-3-ylamine,
   (R)-6,6-Difluoro-5-[2-fluoro-5-(tetrahydro-pyran-4-yl)-phenyl]-5,7,7-trimethyl-2,5,6,7-tetrahydro-[1,4]oxazepin-3-ylamine,
   (R)-5-[5-(3-Chloro-phenylethynyl)-2-fluoro-phenyl]-6,6-difluoro-5,7,7-trimethyl-2,5,6,7-tetrahydro-[1,4]oxazepin-3-ylamine,
   (R)-6,6-Difluoro-5-[2-fluoro-5-(2-methyl-thiazol-4-ylethynyl)-phenyl]-5,7,7-trimethyl-2,5,6,7-tetrahydro-[1,4]oxazepin-3-ylamine,
   (R)-5-[5-(6-Chloro-benzooxazol-2-yl)-2-fluoro-phenyl]-6,6-difluoro-5,7,7-trimethyl-2,5,6,7-tetrahydro-[1,4]oxazepin-3-ylamine,
   (R)-5-[5-(6-Chloro-benzothiazol-2-yl)-2-fluoro-phenyl]-6,6-difluoro-5,7,7-trimethyl-2,5,6,7-tetrahydro-[1,4]oxazepin-3-ylamine,
   (R)-6,6-Difluoro-5-[2-fluoro-5-(1-pyridin-2-yl-1H-imidazol-4-yl)-phenyl]-5,7,7-trimethyl-2,5,6,7-tetrahydro-[1,4]oxazepin-3-ylamine,
   (R)-6,6-Difluoro-5-{2-fluoro-5-[1-(5-trifluoromethyl-pyridin-2-yl)-1H-imidazol-4-yl]-phenyl}-5,7,7-trimethyl-2,5,6,7-tetrahydro-[1,4]oxazepin-3-ylamine, (R)-5-[5-(3-Chloro-phenylethynyl)-2,4-difluoro-phenyl]-6,6-difluoro-5,7,7-trimethyl-2,5,6,7-tetrahydro-[1,4]oxazepin-3-ylamine, and (R)-5-[5-(5-Chloro-pyridin-3-yl)-2,4-difluoro-phenyl]-6,6-difluoro-5,7,7-trimethyl-2,5,6,7-tetrahydro-[1,4]oxazepin-3-ylamine or a pharmaceutically acceptable salt thereof.

26. The compound according to claim 1, selected from the group consisting of (R)-5-[5-(6-Chloro-benzooxazol-2-yl)-2,4-difluoro-phenyl]-6,6-difluoro-5,7,7-trimethyl-2,5,6,7-tetrahydro-[1,4]oxazepin-3-ylamine, (R)-5-[5-(5-Chloro-pyrimidin-2-yl)-2,4-difluoro-phenyl]-6,6-difluoro-5,7,7-trimethyl-2,5,6,7-tetrahydro-[1,4]oxazepin-3-ylamine, (R)-5-[5-(5-Chloro-pyrimidin-2-ylethynyl)-2-fluoro-phenyl]-6,6-difluoro-5,7,7-trimethyl-2,5,6,7-tetrahydro-[1,4]oxazepin-3-ylamine, (R)-5-[5-(2-Chloro-pyridin-4-ylethynyl)-2-fluoro-phenyl]-6,6-difluoro-5,7,7-trimethyl-2,5,6,7-tetrahydro-[1,4]oxazepin-3-ylamine, (R)-5-[5-(6-Chloro-pyridazin-3-ylethynyl)-2-fluoro-phenyl]-6,6-difluoro-5,7,7-trimethyl-2,5,6,7-tetrahydro-[1,4]oxazepin-3-ylamine, (R)-5-[5-(5-Chloro-pyridin-3-ylethynyl)-2-fluoro-phenyl]-6,6-difluoro-5,7,7-trimethyl-2,5,6,7-tetrahydro-[1,4]oxazepin-3-ylamine, (R)-6,6-Difluoro-5-[2-fluoro-5-(5-methoxy-pyrazin-2-ylethynyl)-phenyl]-5,7,7-trimethyl-2,5,6,7-tetrahydro-[1,4]oxazepin-3-ylamine, (R)-5-[5-(5-Chloro-benzooxazol-2-yl)-2,4-difluoro-phenyl]-6,6-difluoro-5,7,7-trimethyl-2,5,6,7-tetrahydro-[1,4]oxazepin-3-ylamine, (R)-5-[2,4-Difluoro-5-(2-methoxy-pyrimidin-5-yl)-phenyl]-6,6-difluoro-5,7,7-trimethyl-2,5,6,7-tetrahydro-[1,4]oxazepin-3-ylamine, (R)-5-[5-(3,6-Dihydro-2H-pyran-4-yl)-2-fluoro-phenyl]-6,6-difluoro-5,7,7-trimethyl-2,5,6,7-tetrahydro-[1,4]oxazepin-3-ylamine, and (R)-5-[5-(5,6-Difluoro-benzooxazol-2-yl)-2,4-difluoro-phenyl]-6,6-difluoro-5,7,7-trimethyl-2,5,6,7-tetrahydro-[1,4]oxazepin-3-ylamine, or a pharmaceutically acceptable salt thereof.

27. The compound according to claim 1, selected from the group consisting of (R)-6,6-Difluoro-5-(2-fluoro-5-pyrimidin-5-yl-phenyl)-5-methyl-2,5,6,7-tetrahydro-[1,4]oxazepin-3-ylamine, (R)-5-(2,4-Difluoro-5-pyrimidin-5-yl-phenyl)-6,6-difluoro-5,7,7-trimethyl-2,5,6,7-tetrahydro-[1,4]oxazepin-3-ylamine, (R)-5-(3',5'-Dichloro-4-fluoro-biphenyl-3-yl)-6,6-difluoro-5,7,7-trimethyl-2,5,6,7-tetrahydro-[1,4]oxazepin-3-ylamine, (R)-5-(5'-Chloro-4,3'-difluoro-biphenyl-3-yl)-6,6-difluoro-5,7,7-trimethyl-2,5,6,7-tetrahydro-[1,4]oxazepin-3-ylamine, (R)-5-[2,4-Difluoro-5-(2-methoxy-pyrimidin-5-yl)-phenyl]-6,6-difluoro-5,7,7-trimethyl-2,5,6,7-tetrahydro-[1,4]oxazepin-3-ylamine, (R)-5-[5-(3,6-Dihydro-2H-pyran-4-yl)-2-fluoro-phenyl]-6,6-difluoro-5,7,7-trimethyl-2,5,6,7-tetrahydro-[1,4]oxazepin-3-ylamine, (R)-5-[5-(3-Chloro-phenylethynyl)-2,4-difluoro-phenyl]-6,6-difluoro-5,7,7-trimethyl-2,5,6,7-tetrahydro-[1,4]oxazepin-3-ylamine, (R)-5-[5-(3-Chloro-phenylethynyl)-2-fluoro-phenyl]-6,6-difluoro-5,7,7-trimethyl-2,5,6,7-tetrahydro-[1,4]oxazepin-3-ylamine, (R)-5-[5-(5-Chloro-pyridin-3-yl)-2,4-difluoro-phenyl]-6,6-difluoro-5,7,7-trimethyl-2,5,6,7-tetrahydro-[1,4]oxazepin-3-ylamine, and (R)-5-[5-(5-Chloro-pyridin-3-yl)-2-fluoro-phenyl]-6,6-difluoro-5,7,7-trimethyl-2,5,6,7-tetrahydro-[1,4]oxazepin-3-ylamine, or a pharmaceutically acceptable salt thereof.

28. The compound according to claim 1, selected from the group consisting of (R)-5-[5-(5-Chloro-pyrimidin-2-yl)-2,4-difluoro-phenyl]-6,6-difluoro-5,7,7-trimethyl-2,5,6,7-tetrahydro-[1,4]oxazepin-3-ylamine, (R)-5-[5-(6-Chloro-benzooxazol-2-yl)-2,4-difluoro-phenyl]-6,6-difluoro-5,7,7-trimethyl-2,5,6,7-tetrahydro-[1,4]oxazepin-3-ylamine, (R)-5-[5-(6-Chloro-benzooxazol-2-yl)-2-fluoro-phenyl]-6,6-difluoro-5,7,7-trimethyl-2,5,6,7-tetrahydro-[1,4]oxazepin-3-ylamine, (R)-5-[5-(6-Chloro-benzothiazol-2-yl)-2-fluoro-phenyl]-6,6-difluoro-5,7,7-trimethyl-2,5,6,7-tetrahydro-[1,4]oxazepin-3-ylamine, (R)-5-{2,4-Difluoro-5-[1-(4-fluoro-phenyl)-1H-pyrazol-4-yl]-phenyl}-6,6-difluoro-5,7,7-trimethyl-2,5,6,7-tetrahydro-[1,4]oxazepin-3-ylamine, (R)-5-{5-[1-(3-Chloro-phenyl)-1H-pyrazol-4-yl]-2-fluoro-phenyl}-6,6-difluoro-5,7,7-trimethyl-2,5,6,7-tetrahydro-[1,4]oxazepin-3-ylamine, (R)-6,6-Difluoro-5-(2-fluoro-5-pyrimidin-5-yl-phenyl)-5,7,7-trimethyl-2,5,6,7-tetrahydro-[1,4]oxazepin-3-ylamine, (R)-6,6-Difluoro-5,7,7-trimethyl-5-(4,3',5'-trifluoro-biphenyl-3-yl)-2,5,6,7-tetrahydro-[1,4]oxazepin-3-ylamine, (R)-6,6-Difluoro-5-[2-fluoro-5-(1-pyridin-2-yl-1H-imidazol-4-yl)-phenyl]-5,7,7-trimethyl-2,5,6,7-tetrahydro-[1,4]oxazepin-3-ylamine, and (R)-6,6-Difluoro-5-[2-fluoro-5-(2-methyl-2H-pyrazol-3-yl)-phenyl]-5,7,7-trimethyl-2,5,6,7-tetrahydro-[1,4]oxazepin-3-ylamine, (R)-6,6-Difluoro-5-[2-fluoro-5-(2-methyl-thiazol-4-ylethynyl)-phenyl]-5,7,7-trimethyl-2,5,6,7-tetrahydro-[1,4]oxazepin-3-ylamine, or a pharmaceutically acceptable salt thereof.

29. The compound according to claim 1, selected from the group consisting of (R)-6,6-Difluoro-5-[2-fluoro-5-(tetrahydro-pyran-4-yl)-phenyl]-5,7,7-trimethyl-2,5,6,7-tetrahydro-[1,4]oxazepin-3-ylamine, (R)-6,6-Difluoro-5-{2-fluoro-5-[1-(4-fluoro-phenyl)-1H-pyrazol-4-yl]-phenyl}-5,7,7-trimethyl-2,5,6,7-tetrahydro-[1,4]oxazepin-3-ylamine, (R)-6,6-Difluoro-5-{2-fluoro-5-[1-(5-trifluoromethyl-pyridin-2-yl)-1H-imidazol-4-yl]-phenyl}-5,7,7-trimethyl-2,5,6,7-tetrahydro-[1,4]oxazepin-3-ylamine, 3'-((R)-3-Amino-6,6-difluoro-5,7,7-trimethyl-2,5,6,7-tetrahydro-[1,4]oxazepin-5-yl)-4'-fluoro-biphenyl-3-sulfonic acid tert-butylamide, 3'-((R)-3-Amino-6,6-difluoro-5,7,7-trimethyl-2,5,6,7-tetrahydro-[1,4]oxazepin-5-yl)-4'-fluoro-biphenyl-3-sulfonic acid 2,2-dimethyl-propyl ester, 3'-((R)-3-Amino-6,6-difluoro-5,7,7-trimethyl-2,5,6,7-tetrahydro-[1,4]oxazepin-5-yl)-6,4'-difluoro-biphenyl-3-carbonitrile, 3'-((R)-3-Amino-6,6-difluoro-5,7,7-trimethyl-2,5,6,7-tetrahydro-[1,4]oxazepin-5-yl)-4'-fluoro-biphenyl-3-carbonitrile,
3'-((R)-3-Amino-6,6-difluoro-5,7,7-trimethyl-2,5,6,7-tetrahydro-[1,4]oxazepin-5-yl)-4'-fluoro-biphenyl-4-carbonitrile,
5'-((R)-3-Amino-6,6-difluoro-5,7,7-trimethyl-2,5,6,7-tetrahydro-[1,4]oxazepin-5-yl)-2',4'-difluoro-biphenyl-4-carbonitrile,
5'-((R)-3-Amino-6,6-difluoro-5,7,7-trimethyl-2,5,6,7-tetrahydro-[1,4]oxazepin-5-yl)-2',4'-difluoro-biphenyl-3-carbonitrile, and
5-[3-((R)-3-Amino-6,6-difluoro-5,7,7-trimethyl-2,5,6,7-tetrahydro-[1,4]oxazepin-5-yl)-4-fluoro-phenyl]-pyridine-3-sulfonic acid tert-butylamide,
or a pharmaceutically acceptable salt thereof.

30. The compound according to claim 1, selected from the group consisting of
(R)-6,6-Difluoro-5-(2-fluoro-5-pyrimidin-5-yl-phenyl)-5-methyl-2,5,6,7-tetrahydro-[1,4]oxazepin-3-ylamine formate,
(R)-5-(2,4-Difluoro-5-pyrimidin-5-yl-phenyl)-6,6-difluoro-5,7,7-trimethyl-2,5,6,7-tetrahydro-[1,4]oxazepin-3-ylamine,
(R)-5-[5-(5-Chloro-pyridin-3-yl)-2,4-difluoro-phenyl]-6,6-difluoro-5,7,7-trimethyl-2,5,6,7-tetrahydro-[1,4]oxazepin-3-ylamine,
(R)-6,6-Difluoro-5-(2-fluoro-5-pyrimidin-5-yl-phenyl)-5,7,7-trimethyl-2,5,6,7-tetrahydro-[1,4]oxazepin-3-ylamine, and
3'-((R)-3-Amino-6,6-difluoro-5,7,7-trimethyl-2,5,6,7-tetrahydro-[1,4]oxazepin-5-yl)-6,4'-difluoro-biphenyl-3-carbonitrile.

31. A pharmaceutical composition comprising a therapeutically effective amount of a compound of formula I

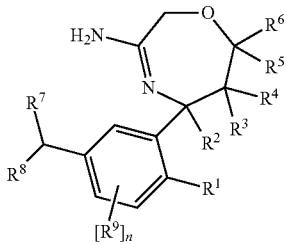

I wherein
$R^1$ is selected from the groups consisting of
hydrogen and
halogen;
$R^2$ is selected from the groups consisting of
$C_{1-6}$-alkyl and
halogen-$C_{1-3}$-alkyl;
$R^3$ is selected from the groups consisting of
hydrogen,
halogen, and
$C_{1-6}$-alkyl;
$R^4$ is selected from the groups consisting of
hydrogen,
halogen, and
$C_{1-6}$-alkyl;
$R^5$ is selected from the groups consisting of
hydrogen and
$C_{1-6}$-alkyl;
$R^6$ is selected from the groups consisting of
hydrogen and
$C_{1-6}$-alkyl;
$R^7$ and $R^8$ together with the C atom to which they are attached form a group selected from the group consisting of
aryl,
aryl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{1-6}$-alkyl-NH—$SO_2$—, $C_{1-6}$-alkyl-$SO_2$—, $C_{1-6}$-alkoxy-$SO_2$— and $C_{1-6}$-alkyl,
heteroaryl,
heteroaryl substituted by 1-4 substituents individually selected from aryl, cyano, cyano-$C_{1-6}$-alkyl, halogen, halogen-$C_{1-6}$-alkoxy, halogen-$C_{1-6}$-alkyl, halogen-$C_{1-6}$-alkyl-heteroaryl, halogen-aryl, heteroaryl, $C_{1-6}$-alkoxy, $C_{1-6}$-alkoxy-$C_{1-6}$-alkyl, $C_{1-6}$-alkyl-NH—$SO_2$— and $C_{1-6}$-alkyl,
$C_{2-6}$-alkynyl,
$C_{2-6}$-alkynyl substituted by 1-5 substituents individually selected from aryl, cyano, halogen-aryl, halogen, $C_{1-6}$-alkyl, $C_{1-6}$-alkyl-aryl, cyano-heteroaryl, halogen-heteroaryl, $C_{1-6}$-alkyl-heteroaryl, heteroaryl, $C_{1-6}$-alkoxy-heteroaryl and $C_{1-6}$-alkoxy;
heterocyclyl, and
heterocyclyl substituted by 1-4 substituents individually selected from halogen, halogen-$C_{1-6}$-alkoxy, halogen-$C_{1-6}$-alkyl, $C_{1-6}$-alkoxy, $C_{1-6}$-alkoxy-$C_{1-6}$-alkyl and $C_{1-6}$-alkyl;
$R^9$ is selected from the group consisting of
halogen and
$C_{1-6}$-alkyl; and
n is 0 or 1;
or a pharmaceutically acceptable salt thereof.

* * * * *